(12) United States Patent
Chopra et al.

(10) Patent No.: US 10,695,352 B2
(45) Date of Patent: Jun. 30, 2020

(54) COMBINATION THERAPY FOR TREATING MALIGNANCIES

(71) Applicants: Celgene Corporation, Summit, NJ (US); Agios Pharmaceuticals, Inc., Cambridge, MA (US)

(72) Inventors: Vivek Saroj Kumar Chopra, South San Francisco, CA (US); Jorge DiMartino, Belmont, CA (US); Laurie A. Kenvin, New Hope, PA (US); Robert Douglas Knight, Berkeley Heights, NJ (US); Kyle MacBeth, San Francisco, CA (US); Krishnan Viswanadhan, East Hanover, NJ (US); Qiang Xu, Basking Ridge, NJ (US); Samuel V. Agresta, Lexington, MA (US)

(73) Assignees: Celgene Corporation, Summit, NJ (US); Agios Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 15/768,462

(22) PCT Filed: Oct. 14, 2016

(86) PCT No.: PCT/US2016/057102
§ 371 (c)(1),
(2) Date: Apr. 13, 2018

(87) PCT Pub. No.: WO2017/066611
PCT Pub. Date: Apr. 20, 2017

(65) Prior Publication Data
US 2018/0303840 A1 Oct. 25, 2018

Related U.S. Application Data

(60) Provisional application No. 62/242,218, filed on Oct. 15, 2015.

(51) Int. Cl.
*A61K 31/53* (2006.01)
*A61K 31/7068* (2006.01)
*A61P 35/02* (2006.01)
*A61K 31/706* (2006.01)

(52) U.S. Cl.
CPC .......... *A61K 31/53* (2013.01); *A61K 31/7068* (2013.01); *A61P 35/02* (2018.01); *A61K 31/706* (2013.01); *A61K 2300/00* (2013.01)

(58) Field of Classification Search
CPC .. A61K 31/53; A61K 31/7068; A61K 31/706; A61K 2300/00; A61P 35/02; A61P 35/00
See application file for complete search history.

(56) References Cited

U.S. PATENT DOCUMENTS

| | | | |
|---|---|---|---|
| 6,887,855 B2 | 5/2005 | Ionescu et al. |
| 6,943,249 B2 | 9/2005 | Ionescu et al. |
| 7,038,038 B2 | 5/2006 | Ionescu et al. |
| 7,078,518 B2 | 7/2006 | Ionescu et al. |
| 7,192,781 B2 | 3/2007 | Luna et al. |
| 7,772,199 B2 | 8/2010 | Ionescu et al. |
| 9,512,107 B2 | 12/2016 | Cianchetta et al. |
| 9,656,999 B2 | 5/2017 | Cianchetta et al. |
| 9,694,013 B2 | 7/2017 | Agresta et al. |
| 9,724,350 B2 | 8/2017 | Travins et al. |
| 9,732,062 B2 | 8/2017 | Cianchetta et al. |
| 9,738,625 B2 | 8/2017 | Agresta et al. |
| 9,751,863 B2 | 9/2017 | Zhang |
| 2002/0051820 A1 | 5/2002 | Shell et al. |
| 2003/0039688 A1 | 2/2003 | Shell et al. |
| 2003/0104053 A1 | 6/2003 | Gusler et al. |
| 2003/0104062 A1 | 6/2003 | Berner et al. |
| 2012/0121515 A1 | 5/2012 | Dang et al. |
| 2013/0316385 A1 | 11/2013 | Cantley et al. |
| 2017/0298045 A1 | 7/2017 | Cianchetta et al. |
| 2017/0157132 A1 | 10/2017 | Wu et al. |
| 2017/0246174 A1 | 10/2017 | Amatangelo et al. |
| 2017/0266193 A1 | 10/2017 | Agresta |
| 2017/0305885 A1 | 10/2017 | Agresta |

FOREIGN PATENT DOCUMENTS

| | | |
|---|---|---|
| WO | WO 2015/006592 A1 | 1/2015 |
| WO | WO 2015/017821 A2 | 2/2015 |
| WO | WO 2015/018060 A1 | 2/2015 |
| WO | WO 2016/126798 A1 | 8/2016 |
| WO | WO 2017/066599 A1 | 4/2017 |

OTHER PUBLICATIONS

Ellwood-Yen et al., Proceedings of the 105th Annual Meeting of the American Association for Cancer Research; Apr. 5-9, 2014; San Diego, CA, abstract (Year: 2014).*
Entry for Enasidenib, PubChem website, https://pubchem.ncbi.nlm.nih.gov/compound/89683805, accessed online on Sep. 10, 2019. (Year: 2019).*
Chou et al., Leukemia, 2011, 25, p. 246-253. (Year: 2011).*
Pleyer et al., Journal of Hematology & Oncology, 2013, 6:32, 13 pages. (Year: 2013).*
Aghili et al., "Hydroxyglutaric aciduria and malignant brain tumor: a case report and literature review," *J. Neurooncol.*, 91:233-236 (2009).
Anonymous, "NCT02632708, ClinicalTrials.gov archive, updated on Dec. 16, 2015," ClinicalTrials.gov, Retrieved from the internet: URL:https://clinicaltrials.gov/archive/NCT02632708/2015_12_15, retrieved on Jan. 12, 2017, 6 pages.
Berge et al., "Pharmaceutical salts," *J. Pharm. Sci.*, 66(1):1-19 (1977).
Cheson et al., "Clinical application and proposal for modification of the International Working Group (IWG) response criteria in myelodysplasia," *Blood*, 108(2):419-425 (2006).

(Continued)

*Primary Examiner* — Jonathan S Lau
(74) *Attorney, Agent, or Firm* — Jones Day

(57) ABSTRACT

Provided are methods and compositions for treating cancers in patients carrying an IDH2 mutation using a combination of an inhibitor of a mutant IDH2 enzyme and a DNA demethylating agent.

15 Claims, 22 Drawing Sheets

(56) References Cited

OTHER PUBLICATIONS

Cheson et al., "Revised recommendations of the International Working Group for Diagnosis, Standardization of Response Criteria, Treatment Outcomes, and Reporting Standards for Therapeutic Trials in Acute Myeloid Leukemia," *J. Clin. Oncol.*, 21(24):4642-4649 (2003).
Dang et al., "Cancer-associated IDH1 mutations produce 2-hydroxyglutarate," *Nature* 462:739-744 (2009).
Foundation Medicine, FoundationOne® Heme,Technical Information and Test Overview, Retrieved on Apr. 6, 2017. Retrieved from the internet: URL: http://foundationone.com/learn.php.
Geisbrecht et al., "The human PICD gene encodes a cytoplasmic and peroxisomal NADP(+)-dependent isocitrate dehydrogenase," *J. Biol. Chem.*, 274(43):30527-30533 (1999).
Genbank Accession No. NM_002168.2 (Feb. 22, 2014).
Genbank Accession No. NM_005896.2 (Sep. 2, 2013).
Genbank Accession No. NP_002159.2 (Apr. 30, 2016).
Genbank Accession No. NP_005887.2 (Jan. 4, 2017).
Gerhard et al., "The status, quality, and expansion of the NIH full-length cDNA project: the Mammalian Gene Collection (MGC)," *Genome Res.*,14(10B):2121-2127 (2004).
IDHIFA label issued Aug. 2017, available at https://www.accessdatalda.gov/drugsatfda_docs/label/2017/209606s0001b1.pdf.
Kolker et al., "NMDA receptor activation and respiratory chain complex V inhibition contribute to neurogeneration in D-2-hydroxyglutaric aciduria," *Eur. J. Neurosci.*, 16:21-28 (2002).
Kolker et al., "White matter disease in cerebral organic acid disorders: clinical implications and suggested pathomechanisms," *Neuropediatrics*, 33:225-231 (2002).
Latini et al., "D-2-hydroxyglutaric acid induces oxidaitive stress in cerebral cortex of young rats," *Eur. J. Neurosci.*, 17:2017-2022 (2003).
Luo et al., "Simultaneous determination of multiple intracellular metabolites in glycolysis, pentose phosphate pathway and tricarboxylic acid cycle by liquid chromatography-mass spectrometry," *J. Chromatogr A.*, 1147:153 164(2007).
Miyawaki et al. "Long-term follow-up of the randomized JALSG AML 201 study comparing high dose Ara-C therapy with conventional consolidation therapy in adult acute myeloid leukemia (AML)," *Blood*, 112:135 (2008).

Munger et al., "Systems-level metabolic flux profiling identifies fatty acid synthesis as a target for antiviral therapy," *Nat. Biotechnol.*, 26(10):1179-1186 (2008).
Oken et al., "Toxicity and response criteria of the Eastern Cooperative Oncology Group," *Am. J. Clin. Oncol.*, 5(6):649-655 (1982).
Ravandi et al., "Prognostic significance of alterations in IDH enzyme isoforms in patients with AML treated with high-dose cytarabine and idarubicin," *Cancer*, 118(10):2665-2673 (2011).
Stein et al., "Abstract CT103: Clinical safety and activity in a phase I trial of AG-221, a first in class, potent inhibitor of the IDH2-mutant protein, in patients with IDH2 mutant positive advanced hematologic malignancies," in Proceedings: AACR Annual Meeting, Apr. 5-9, 2014, San Diego, CA, *Cancer Research*, Oct. 1, 2014, retrieved from the internet: URL:http://cancerres.aacrjournals.org/content/74/19_Supplement/CT103, retrieved on Jan. 12, 2017, 5 pages.
Stein, "AG-221 sparks durable remissions in IDH2-mutated AML," *Oncology Report*, Dec. 7, 2014, Retrieved from the Internet: URL:http://www.targetendonc.com/conference/ash-2014/ag-221-sparks-durable-remissions-in-idh2-mutated-aml, retrieved on Jan. 12, 2017, 3 pages.
Struys et al., "Mutations in the D-2-Hydroxyglutarate dehydrogenase gene cause D-2-hydroxyglutaric aciduria," *Am. J. Hum. Genet.*, 76:358-360 (2005).
Wajner et al., "The role of oxidative damage in the neuropathology of organic acidurias: insights from animal studies," *J. Inherit. Metab. Dis.*, 27:427-448 (2004).
Dinardo et al., "Mutant Isocitrate Dehydrogenase (mIDH) Inhibitors, Enasidenib or Ivosidenib, in Combination with Azacitidine (AZA): Preliminary Results of a Phase 1b/2 Study in Patients with Newly Diagnosed Acute Myeloid Leukemia (AML)", *Blood* 130:639 (2017).
Mani et al., "DNA Demethylating Agents and Epigenetic Therapy of Cancer," *Advances in Genetics*, 70:327-340 (2010).
Dinardo et al., "Enasidenib Plus Azacitidine Significantly Improves Complete Remission and Overall Response Compared with Azacitidine Alone in Patients with Newly Diagnosed Acute Myeloid Leukemia (AML) with Isocitrate Dehydrogenase 2 (IDH2) Mutations: Interim Phase II Results from an Ongoing, Randomized Study," Presented at 2019 ASH Annual Meeting, Dec. 7-10, 2019, Orlando, FL, Abstract 643, 15 pages.

\* cited by examiner

COMBINATION THERAPY FOR TREATING MALIGNANCIES

CROSS REFERENCE TO RELATED APPLICATIONS

This application is a U.S. National Stage filing under 35 U.S.C. § 371 of International Application No. PCT/US2016/057102, filed Oct. 14, 2016, which claims the benefit of the priority to U.S. Provisional Application No. 62/242,218, filed Oct. 15, 2015, the disclosure of each of which is incorporated herein by reference in its entirety.

FIELD

Provided herein are combination therapies for treating hematological malignancies and solid tumors. In one embodiment, the therapies involve treatment with an IDH2 inhibitor and a DNA demethylating agent.

BACKGROUND

Isocitrate dehydrogenases (IDHs) catalyze the oxidative decarboxylation of isocitrate to 2-oxoglutarate (i.e., α-ketoglutarate). These enzymes belong to two distinct subclasses, one of which utilizes NAD(+) as the electron acceptor and the other NADP(+). Five isocitrate dehydrogenases have been reported: three NAD(+)-dependent isocitrate dehydrogenases, which localize to the mitochondrial matrix, and two NADP(+)-dependent isocitrate dehydrogenases, one of which is mitochondrial and the other predominantly cytosolic. Each NADP(+)-dependent isozyme is a homodimer.

IDH2 (isocitrate dehydrogenase 2 (NADP+), mitochondrial) is also known as IDH; IDP; IDHM; IDPM; ICD-M; or mNADP-IDH. The protein encoded by this gene is the NADP(+)-dependent isocitrate dehydrogenase found in the mitochondria. It plays a role in intermediary metabolism and energy production. This protein may tightly associate or interact with the pyruvate dehydrogenase complex. Human IDH2 gene encodes a protein of 452 amino acids. The nucleotide and amino acid sequences for IDH2 can be found as GenBank entries NM_002168.2 and NP_002159.2 respectively. The nucleotide and amino acid sequence for human IDH2 are also described in, e.g., Huh et al., Submitted (November-1992) to the EMBL/GenBank/DDBJ databases; and The MGC Project Team, Genome Res. 14:2121-2127 (2004).

Non-mutant, e.g., wild type, IDH2 catalyzes the oxidative decarboxylation of isocitrate to α-ketoglutarate (α-KG) thereby reducing $NAD^+$ ($NADP^+$) to NADH (NADPH), e.g., in the forward reaction:

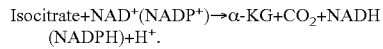

Isocitrate+$NAD^+$($NADP^+$)→α-KG+$CO_2$+NADH (NADPH)+$H^+$.

It has been discovered that mutations of IDH2 present in certain cancer cells result in a new ability of the enzyme to catalyze the NADPH-dependent reduction of α-ketoglutarate to R(−)-2-hydroxyglutarate (2HG). 2HG is not formed by wild-type IDH2. The production of 2HG is believed to contribute to the formation and progression of cancer (Dang, L. et al., Nature 462:739-44, 2009).

Somatic IDH2 mutations occur in a spectrum of solid and hematologic tumors and premalignant disorders, including acute myeloid leukemia (AML) and myelodysplastic syndrome (MDS). Around 15% of AML patient population contains the IDH2 gene mutation which leads to production of oncometabolite 2HG, the accumulation of 2HG inhibits the ten-eleven translocation (TET) group of DNA demethylases resulting in a DNA hypermethylation phenotype. The increased DNA methylation leads to differentiation block and propogation of AML (Wang et al., Science 340:622-626, 2013).

The development of selective inhibitors of an IDH2 mutant enzyme has provided the possibility of therapeutic benefit to AML patients carrying the IDH2 mutation. There have been successful responses in the clinic with decreased blast population and benefit of differentiated functional blood cells. However, the genetic load is present in the patients even with good overall response. Therefore, there is a need for improved therapies for treating cancers having IDH2 mutations.

SUMMARY

In one embodiment, provided herein are methods of treating hematologic malignancies by administering to a subject a combination of a mutant IDH2 inhibitor and a DNA demethylating agent.

In one embodiment, provided herein is a method of treating hematologic malignancies, such as acute myelogenous leukemia (AML), myelodysplastic syndrome (MDS), chronic myelomonocytic leukemia (CMML), myeloid sarcoma, multiple myeloma, lymphoma (e.g., T-cell lymphoma or B-cell lymphoma), angioimmunoblastic T-cell lymphoma (AITL) or blastic plasmacytoid dendritic cell neoplasm, each characterized by the presence of a mutant allele of IDH2, comprising administering to a subject a therapeutically effective amount of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol, or a pharmaceutically acceptable salt, solvate, tautomer, stereoisomer, isotopologue, prodrug, metabolite, or a polymorph thereof (COMPOUND 1) and a DNA demethylating agent.

In one embodiment, the DNA demethylating agent is a cytidine analog.

In one embodiment, cytidine analogs useful in the methods provided herein include, but are not limited to, 5-azacitidine (azacitidine), 5-azadeoxycytidine (decitabine), cytarabine, pseudoisocytidine, gemcitabine, zebularine, FCdR, Emtriva, 5,6-dihydro-5-azacitidine and procaine. In one embodiment, the cytidine analog is decitabine or azacitidine. In one embodiment, the cytidine analog is azacitidine.

In one embodiment, provided herein is a method of treating hematologic malignancies, such as acute myelogenous leukemia (AML), myelodysplastic syndrome (MDS), chronic myelomonocytic leukemia (CMML), myeloid sarcoma, multiple myeloma, lymphoma (e.g., T-cell lymphoma or B-cell lymphoma), angioimmunoblastic T-cell lymphoma (AITL) or blastic plasmacytoid dendritic cell neoplasm, each characterized by the presence of a mutant allele of IDH2, comprising administering to a subject a therapeutically effective amount of COMPOUND 1 and azacitidine.

In one embodiment, provided herein is a method of treating hematologic malignancies, such as acute myelogenous leukemia (AML), myelodysplastic syndrome (MDS), chronic myelomonocytic leukemia (CMML), myeloid sarcoma, multiple myeloma, lymphoma (e.g., T-cell lymphoma or B-cell lymphoma), angioimmunoblastic T-cell lymphoma (AITL) or blastic plasmacytoid dendritic cell neoplasm, each characterized by the presence of a mutant allele of IDH2, comprising administering to a subject a pharmaceutical composition comprising a therapeutically effective amount of COMPOUND 1 and a cytidine analog.

In one embodiment, provided herein is a method of treating hematologic malignancies, such as acute myelogenous leukemia (AML), myelodysplastic syndrome (MDS), chronic myelomonocytic leukemia (CMML), myeloid sarcoma, multiple myeloma, lymphoma (e.g., T-cell lymphoma or B-cell lymphoma), angioimmunoblastic T-cell lymphoma (AITL) or blastic plasmacytoid dendritic cell neoplasm, each characterized by the presence of a mutant allele of IDH2, comprising administering to a subject a pharmaceutical composition comprising a therapeutically effective amount of COMPOUND 1 and azacitidine.

In some embodiments, the hematological malignancy to be treated is an advanced hematological malignancy.

In some embodiments, the hematological malignancy to be treated is AML. In some embodiments, the hematological malignancy to be treated is newly diagnosed AML. In some embodiments, the hematological malignancy is relapsed and/or refractory AML.

In some embodiments, the hematological malignancy to be treated is MDS. In some embodiments, the hematological malignancy to be treated is high risk MDS.

In one embodiment, provided herein is a method of treating solid tumors, such as glioma, melanoma, chondrosarcoma, or cholangiocarcinoma, each characterized by the presence of a mutant allele of IDH2, comprising administering to a subject a therapeutically effective amount of COMPOUND 1 and a DNA demethylating agent.

In one embodiment, provided herein is a method of treating solid tumors, such as glioma, melanoma, chondrosarcoma, or cholangiocarcinoma, each characterized by the presence of a mutant allele of IDH2, comprising administering to a subject a therapeutically effective amount of COMPOUND 1 and azacitidine.

In one embodiment, provided herein is a method of treating solid tumors, such as glioma, melanoma, chondrosarcoma, or cholangiocarcinoma, each characterized by the presence of a mutant allele of IDH2, comprising administering to a subject a pharmaceutical composition comprising a therapeutically effective amount of COMPOUND 1 and a cytidine analog.

In one embodiment, provided herein is a method of treating solid tumors, such as glioma, melanoma, chondrosarcoma, or cholangiocarcinoma, each characterized by the presence of a mutant allele of IDH2, comprising administering to a subject a pharmaceutical composition comprising a therapeutically effective amount of COMPOUND 1 and azacitidine.

In one embodiment, provided herein is a pharmaceutical composition comprising a therapeutically effective amount of COMPOUND 1 and a cytidine analog.

In one embodiment, provided herein is a pharmaceutical composition comprising a therapeutically effective amount of COMPOUND 1 and azacitidine.

BRIEF DESCRIPTION OF THE DRAWINGS

FIG. 1, in section B depicts COMPOUND 1 and azacitidine combination schedule and dosing paradigms for concurrent treatment of: treatment for 7 days with the combination of azacitidine and COMPOUND 1 followed by 7 days of the treatment with azacitidine, COMPOUND 1 and EPO. The cells were harvested on Day 14 and subjected to various endpoint assays for monitoring differentiation and death.

DETAILED DESCRIPTION

Figure 1:
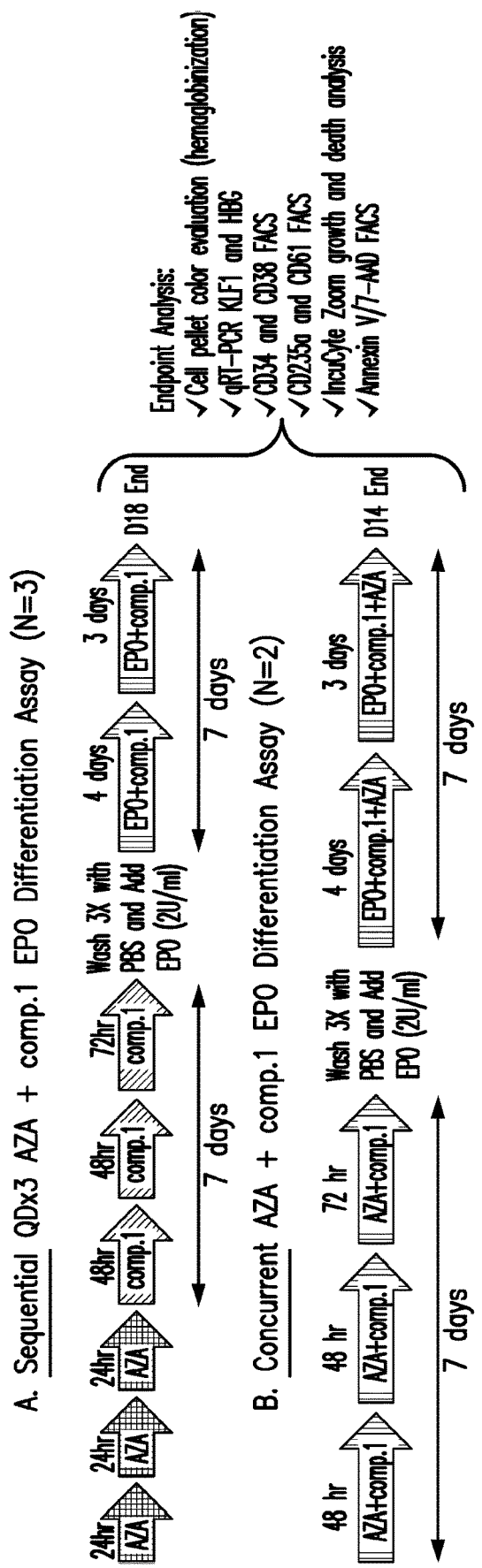
FIG. 1 in section A depicts COMPOUND 1 and azacitidine (AZA) combination schedule and dosing paradigms for sequential treatment of: 3 days (QDx3) of pre-treatment with azacitidine followed by treatment with the COMPOUND 1 for one week and erythropoietin (EPO)+COMPOUND 1 for another week. The cells were harvested on Day 18 and subjected to various endpoint assays for monitoring differentiation and death.

The details of construction and the arrangement of components set forth in the following description or illustrated in the drawings are not meant to be limiting. Other embodiments and different ways to practice the invention are expressly included. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

Definitions

The term a "mutant IDH2 inhibitor" or "inhibitor of IDH2 mutant(s)" means a molecule e.g., a polypeptide, peptide, or small molecule (e.g., a molecule of less than 1,000 daltons), or aptomer, that binds to an IDH2 mutant subunit and inhibits neoactivity, e.g., by inhibiting formation of a dimer, e.g., a homodimer of mutant IDH2 subunits or a heterodimer of a mutant and a wildype subunit. In some embodiments, the neoactivity inhibition is at least about 60%, 70%, 80%, 90%, 95% or 99% as compared to the activity in the absence of the mutant IDH2 inhibitor. In one embodiment, the mutant IDH2 inhibitor is COMPOUND 1.

The term "elevated levels of 2HG" means 10%, 20% 30%, 50%, 75%, 100%, 200%, 500% or more 2HG is present in a subject that carries a mutant IDH2 allele than is present in a subject that does not carry a mutant IDH2 allele. The term "elevated levels of 2HG" may refer to the amount of 2HG within a cell, within a tumor, within an organ comprising a tumor, or within a bodily fluid.

The term "bodily fluid" includes one or more of amniotic fluid surrounding a fetus, aqueous humour, blood (e.g., blood plasma), serum, Cerebrospinal fluid, cerumen, chyme, Cowper's fluid, female ejaculate, interstitial fluid, lymph, breast milk, mucus (e.g., nasal drainage or phlegm), pleural fluid, pus, saliva, sebum, semen, serum, sweat, tears, urine, vaginal secretion, or vomit.

The terms "inhibit" or "prevent" include both complete and partial inhibition and prevention. An inhibitor may completely or partially inhibit the intended target.

The term "subject" is intended to include human and non-human animals. Exemplary human subjects include a human patient (referred to as a patient) having a disorder, e.g., a disorder described herein or a normal subject. The term "non-human animals" of one aspect of the invention includes all vertebrates, e.g., non-mammals (such as chickens, amphibians, reptiles) and mammals, such as non-human primates, domesticated and/or agriculturally useful animals, e.g., sheep, dog, cat, cow, pig, etc.

The term "treat" means decrease, suppress, attenuate, diminish, arrest, or stabilize the development or progression of a disease/disorder (e.g., an advanced hematologic malignancy, such as acute myelogenous leukemia (AML), myelodysplastic syndrome (MDS), chronic myelomonocytic leukemia (CMML), myeloid sarcoma, multiple myeloma, or lymphoma (e.g., T-cell lymphoma), each characterized by the presence of a mutant allele of IDH2), lessen the severity of the disease/disorder or improve the symptoms associated with the disease/disorder.

The term "myelodysplastic syndrome" refers to hematological conditions characterized by abnormalities in the production of one or more of the cellular components of blood (red cells, white cells (other than lymphocytes) and platelets (or their progenitor cells, megakaryocytes.

The term "relapsed" refers to a situation where, after therapy, patients who have had a remission of cancer, including AML, have a return of cancer cells.

The term "refractory or resistant" refers to a circumstance where patients, even after intensive treatment, have residual cancer cells in their body.

An amount of a compound, including a pharmaceutically acceptable salt, solvate, tautomer, stereoisomer, isotopologue, prodrug, metabolite, or a polymorph thereof, effective to treat a disorder, or a "therapeutically effective amount" or "therapeutically effective dose" refers to an amount of the compound, including a pharmaceutically acceptable salt, solvate, tautomer, stereoisomer, isotopologue, prodrug, metabolite, or a polymorph thereof, which is effective, upon single or multiple dose administration to a subject, in treating a cell, or in curing, alleviating, relieving or improving a subject with a disorder beyond that expected in the absence of such treatment.

Leukemia, in particular AML, response to treatment can be assessed based on the International Working Group Response Criteria in AML (Cheson et al. Revised recommendations of the International Working Group for diagnosis, standardization of response criteria, treatment outcomes, and reporting standards for therapeutic trials in acute myeloid leukemia. *J Clin Oncol* 2003; 21(24):4642-9).

| Response Criterion | Time of Assessment | Neutrophils (μL) | Platelets (μL) | Bone Marrow Blasts (%) | Other |
|---|---|---|---|---|---|
| Early Treatment assessment | 7-10 days after therapy | NA | NA | <5 | |
| Morphologic Leukemia-free State | Varies by protocol | NA | NA | <5 | Flow cytometry EMD |
| Morphologic CR | Varies by protocol | ≥1,000 | ≥100,000 | <5 | Transfusion EMD |
| Cytogenetic CR (CRc) | Varies by protocol | ≥1,000 | ≥100,000 | <5 | Cytogenetics - normal, EMD |

-continued

| Response Criterion | Time of Assessment | Neutrophils (μL) | Platelets (μL) | Bone Marrow Blasts (%) | Other |
|---|---|---|---|---|---|
| Molecular CR (CRm) | Varies by protocol | ≥1,000 | ≥100,000 | <5 | Molecular - negative, EMD |
| Morphologic CR with incomplete blood recovery (CRi) | Varies by protocol | Fulfill all criteria for CR except for residual neutropenia (<1,000/μL) or thrombocytopenia (<100,000/μL). | | | |
| Partial Remission | Varies by protocol | ≥1,000 | ≥100,000 | Decrease ≥50 resulting in 5 to 25 | Blasts ≤5% if Auer rod positive |
| Relapse after CR | Varies by protocol | Reappearance of leukemic blasts in the peripheral blood or ≥5% blasts in the bone marrow not attributable to any other cause (eg, bone marrow regeneration after consolidation therapy). | | | |

Key:
AML = acute myelogenous leukemia;
CR = complete remission;
EMD = extramedullary disease;
IWG = International Working Group;
NA = not applicable.

For MDS, response to treatment can be assessed based on the modified International Working Group (IWG) response criteria in myelodysplasia (Cheson, et al., *Blood* 2006; 108:419-425)

Modified International Working Group Response Criteria for Altering Natural History of MDS

| Category | Response criteria (responses must last at least 4 wk) |
|---|---|
| Complete remission | Bone marrow: ≤5% myeloblasts with normal maturation of all cell lines* |
| | Persistent dysplasia will be noted*† |
| | Peripheral blood† |
| | Hgb ≥11 g/dL |
| | Platelets ≥100 × 10⁹/L |
| | Neutrophils ≥1.0 × 10⁹/L† |
| | Blasts 0% |
| Partial remission | All CR criteria if abnormal before treatment except: |
| | Bone marrow blasts decreased by ≥50% over pretreatment but still >5% |
| | Cellularity and morphology not relevant |
| Marrow CR† | Bone marrow: ≤5% myeloblasts and decrease by ≥50% over pretreatment† |
| | Peripheral blood: if HI responses, they will be noted in addition to marrow CR† |
| Stable disease | Failure to achieve at least PR, but no evidence of progression for >8 wks |
| Failure | Death during treatment or disease progression characterized by worsening of cytopenias, increase in percentage of bone marrow blasts, or progression to a more advanced MDS FAB subtype than pretreatment |
| Relapse after CR or PR | At least 1 of the following: |
| | Return to pretreatment bone marrow blast percentage |
| | Decrement of ≥50% from maximum remission/response levels in granulocytes or platelets |
| | Reduction in Hgb concentration by ≥1.5 g/dL or transfusion dependence |
| Cytogenetic response | Complete |
| | Disappearance of the chromosomal abnormality without appearance of new ones |
| | Partial |
| | At least 50% reduction of the chromosomal abnormality |
| Disease progression | For patients with: |
| | Less than 5% blasts: ≥50% increase in blasts to >5% blasts |
| | 5%-10% blasts: ≥50% increase to >10% blasts |
| | 10%-20% blasts: ≥50% increase to >20% blasts |
| | 20%-30% blasts: ≥50% increase to >30% blasts |
| | Any of the following: |
| | At least 50% decrement from maximum remission/response in granulocytes or platelets |
| | Reduction in Hgb by ≥2 g/dL |
| | Transfusion dependence |
| Survival | Endpoints: |
| | Overall: death from any cause |
| | Event free: failure or death from any cause |
| | PFS: disease progression or death from MDS |
| | DFS: time to relapse |
| | Cause-specific death: death related to MDS |

Deletions to IWG response criteria are not shown.
To convert hemoglobin from grams per deciliter to grams per liter, multiply grams per deciliter by 10.
MDS indicates myelodysplastic syndromes;
Hgb, hemoglobin;
CR, complete remission;
HI, hematologic improvement;
PR, partial remission;
FAB, French-American-British;
AML, acute myeloid leukemia;
PFS, progression-free survival;
DFS, disease-free survival.
*Dysplastic changes should consider the normal range of dysplastic changes (modification). 41
†Modification to IWG response criteria.
‡In some circumstances, protocol therapy may require the initiation of further treatment (eg, consolidation, maintenance) before the 4-week period. Such patients can be included in the response category into which they fit at the time the therapy is started. Transient cytopenias during repeated chemotherapy courses should not be considered as interrupting durability of response, as long as they recover to the improved counts of the previous course.

Modified International Working Group Response Criteria for Hematologic Improvement

| Hematologic improvement* | Response criteria (responses must last at least 8 wk)† |
|---|---|
| Erythroid response (pretreatment, <11 g/dL) | Hgb increase by ≥1.5 g/dL |
| | Relevant reduction of units of RBC transfusions by an absolute number of at least 4 RBC transfusions/8 wk compared with the pretreatment transfusion number in the previous 8 wk. Only RBC transfusions given for a Hgb of ≤9.0 g/dL pretreatment will count in the RBC transfusion response evaluation† |
| Platelet response (pretreatment, <100 × 10⁹/L) | Absolute increase of ≥30 × 10⁹/L for patients starting with >20 × 10⁹/L platelets |
| | Increase from <20 × 10⁹/L to >20 × 10⁹/L and by at least 100%† |
| Neutrophil response (pretreatment, <1.0 × 10⁹/L) | At least 100% increase and an absolute increase >0.5 × 10⁹/L† |
| Progression or relapse after HI† | At least 1 of the following: |
| | At least 50% decrement from maximum response levels in granulocytes or platelets |
| | Reduction in Hgb by ≥1.5 g/dL |
| | Transfusion dependence |

Deletions to the IWG response criteria are not shown.

To convert hemoglobin levels from grams per deciliter to grams per liter, multiply grams per deciliter by 10.

Hgb indicates hemoglobin; RBC: red blood cell; HI: hematologic improvement.

\* Pretreatment counts averages of at least 2 measurements (not influenced by transfusions)≥1 week apart (modification).

† Modification to IWG response criteria.

‡ In the absence of another explanation, such as acute infection, repeated courses of chemotherapy (modification), gastrointestinal bleeding, hemolysis, and so forth. It is recommended that the 2 kinds of erythroid and platelet responses be reported overall as well as by the individual response pattern.

As used herein, ECOG status refers to Eastern Cooperative Oncology Group (ECOG) Performance Status (Oken M, et al Toxicity and response criteria of the Eastern Cooperative Oncology Group. *Am J Clin Oncol* 1982; 5(6):649-655), as shown below:

| Score | Description |
|---|---|
| 0 | Fully active, able to carry on all pre-disease performance without restriction |
| 1 | Restricted in physically strenuous activity but ambulatory and able to carry out work of a light or sedentary nature, eg, light housework, office work. |
| 2 | Ambulatory and capable of all self-care but unable to carry out any work activities. Up and about more than 50% of waking hours. |
| 3 | Capable of only limited self-care, confined to bed or chair more than 50% of waking hours. |
| 4 | Completely disabled. Cannot carry on any self-care. Totally confined to bed or chair |
| 5 | Dead |

In one embodiment, provided herein are methods for improving the Eastern Cooperative Oncology Group Performance Status (ECOG) of a patient, comprising administering an effective amount of a compound described herein.

The term "co-administering" as used herein with respect to additional cancer therapeutic agents means that the additional cancer therapeutic agent may be administered together with a compound provided herein as part of a single dosage form (such as a composition comprising a compound and a second therapeutic agent as described above) or as separate, multiple dosage forms. Alternatively, the additional cancer therapeutic agent may be administered prior to, consecutively with, or following the administration of a compound provided herein. In such combination therapy treatment, both the compounds provided herein and the second therapeutic agent(s) are administered by conventional methods. The administration of a composition comprising both a compound provided herein and a second therapeutic agent, to a subject does not preclude the separate administration of that same therapeutic agent, any other second therapeutic agent or any compound provided herein to said subject at another time during a course of treatment. The term "co-administering" as used herein with respect to an additional cancer treatment means that the additional cancer treatment may occur prior to, consecutively with, concurrently with or following the administration of a compound provided herein.

The term "DNA demethylating agent" refers to an agent that inhibits the transfer of a methyl group to DNA. In one embodiment, the DNA demethylating agent is a cytidine analog.

The term "a cytidine analog" referred to herein is intended to encompass the free base of the cytidine analog, or a salt, solvate, hydrate, cocrystal, complex, prodrug, precursor, metabolite, and/or derivative thereof. In certain embodiments, a cytidine analog referred to herein encompasses the free base of the cytidine analog, or a salt, solvate, hydrate, cocrystal or complex thereof. In certain embodiments, a cytidine analog referred to herein encompasses the free base of the cytidine analog, or a pharmaceutically acceptable salt, solvate, or hydrate thereof.

The term "substantially free of other stereoisomers" as used herein means a preparation enriched in a compound having a selected stereochemistry at one or more selected stereocenters by at least about 60%, 65%, 70%, 75%, 80%, 85%, 90%, 95%, 96%, 97%, 98%, or 99%.

The term "enriched" means that at least the designated percentage of a preparation is the compound having a selected stereochemistry at one or more selected stereocenters.

The term "crystalline" refers to a solid having a highly regular chemical structure. In particular, a crystalline COMPOUND 1 may be produced as one or more single crystalline forms of COMPOUND 1. For the purposes of this application, the terms "crystalline form", "single crystalline form" and "polymorph" are synonymous; the terms distinguish between crystals that have different properties (e.g., different XRPD patterns and/or different DSC scan results). The term "polymorph" includes pseudopolymorphs, which are typically different solvates of a material, and thus their properties differ from one another. Thus, each distinct polymorph and pseudopolymorph of COMPOUND 1 is considered to be a distinct single crystalline form herein.

The term "substantially crystalline" refers to forms that may be at least a particular weight percent crystalline. Particular weight percentages are 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 10% and 100%. In some embodiments, substantially crystalline refers to a COMPOUND 1 that is at least 70% crystalline. In other embodiments, substantially crystalline refers to a COMPOUND 1 that is at least 90% crystalline.

The term "isolated" refers to forms that may be at least a particular weight percent of a particular crystalline form of compound. Particular weight percentages are 90%, 91%, 92%, 93%, 94%, 95%, 96%, 97%, 98%, 99%, 99.5%, 99.9%, or any percentage between 90% and 100%.

The term "solvate or solvated" means a physical association of a compound, including a crystalline form thereof, of this invention with one or more solvent molecules. This physical association includes hydrogen bonding. In certain instances the solvate will be capable of isolation, for example when one or more solvent molecules are incorporated in the crystal lattice of the crystalline solid. "Solvate or solvated" encompasses both solution-phase and isolable solvates. Representative solvates include, for example, a hydrate, ethanolates or a methanolate.

The term "hydrate" is a solvate wherein the solvent molecule is $H_2O$ that is present in a defined stoichiometric amount, and may, for example, include hemihydrate, monohydrate, dihydrate, or trihydrate.

The term "mixture" is used to refer to the combined elements of the mixture regardless of the phase-state of the combination (e.g., liquid or liquid/crystalline).

The term "seeding" is used to refer to the addition of a crystalline material to initiate recrystallization or crystallization.

The term "antisolvent" is used to refer to a solvent in which compounds, including crystalline forms thereof, are poorly soluble.

The term "pharmaceutically acceptable carrier or adjuvant" refers to a carrier or adjuvant that may be administered to a subject, together with a compound of one aspect of this invention, and which does not destroy the pharmacological activity thereof and is nontoxic when administered in doses sufficient to deliver a therapeutic amount of the compound.

The term "a pharmaceutically-acceptable salt" as used herein refers to non-toxic acid or base addition salts of the compound to which the term refers. Examples of pharmaceutically acceptable salts are discussed in Berge et al., 1977, "Pharmaceutically Acceptable Salts." *J. Pharm. Sci.* Vol. 66, pp. 1-19.

The term "about" means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

Compounds

In one embodiment, COMPOUND 1 is 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol, or a pharmaceutically acceptable salt, solvate, tautomer, stereoisomer, isotopologue, prodrug, metabolite, or a polymorph thereof, having the following formula:

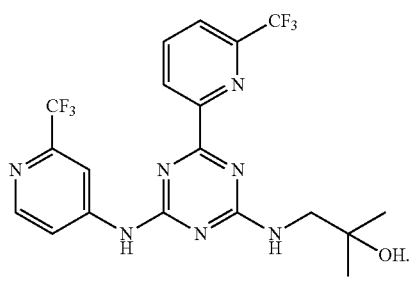 [SMILES: CC(C)(O)CNc1nc(Nc2ccnc(C(F)(F)F)c2)nc(-c2cccc(C(F)(F)F)n2)n1]

COMPOUND 1 may also comprise one or more isotopic substitutions ("Isotopologues"). For example, H may be in any isotopic form, including $^1H$, $^2H$ (D or deuterium), and $^3H$ (T or tritium); C may be in any isotopic form, including $^{12}C$, $^{13}C$, and $^{14}C$; O may be in any isotopic form, including $^{16}O$ and $^{18}O$; and the like. For example, COMPOUND 1 is enriched in a specific isotopic form of H, C and/or O by at least about 60%, 65%, 70%, 75%, 80%, 85%, 90%, 95%, 96%, 97%, 98%, or 99%.

COMPOUND 1 in certain embodiments may also be represented in multiple tautomeric forms, in such instances, one aspect of the invention expressly includes all tautomeric forms of COMPOUND 1 described herein, even though only a single tautomeric form may be represented (e.g., keto-enol tautomers). All such isomeric forms of COMPOUND 1 are expressly included herein. Synthesis of COMPOUND 1 is described in US published application US-2013-0190287-A1 published Jul. 25, 2013, which is incorporated by reference in its entirety.

It may be convenient or desirable to prepare, purify, and/or handle a corresponding salt of COMPOUND 1, for example, a pharmaceutically-acceptable salt. Examples of pharmaceutically acceptable salts are discussed in Berge et al., 1977, "Pharmaceutically Acceptable Salts." *J. Pharm. Sci.* Vol. 66, pp. 1-19.

For example, if COMPOUND 1 is anionic, or has a functional group which may be anionic (e.g., —NH— may be —N—), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{3+}$. Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If COMPOUND is cationic, or has a functional group that may be cationic (e.g., —NHR may be —$NH_2R^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. In one embodiment, COMPOUND 1 comprises the mesylate salt of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol. Examples of suitable polymeric organic anions include, but are not limited to, those derived from the following polymeric acids: tannic acid, carboxymethyl cellulose.

COMPOUND 1 for use in the methods and pharmaceutical compositions provided herein therefore includes the COMPOUND 1 itself, as well as its pharmaceutically acceptable salts, solvates, tautomers, stereoisomers, isotopologues, prodrugs, metabolites, or polymorphs. Metabolites of COMPOUND 1 are disclosed in patent application publication WO2015/006592, which is incorporated herein by reference in its entirety. COMPOUND 1 provided herein may be modified and converted to a prodrug by appending appropriate functionalities to enhance selected biological properties, e.g., targeting to a particular tissue. Such modifications (i.e., prodrugs) are known in the art and include those which increase biological penetration into a given biological compartment (e.g., blood, lymphatic system, central nervous system), increase oral availability, increase solubility to allow administration by injection, alter metabolism and alter rate of excretion. Examples of prodrugs include esters (e.g., phosphates, amino acid (e.g., valine) esters), carbamates and other pharmaceutically acceptable derivatives, which, upon administration to a subject, are capable of providing active compounds.

It has been found that COMPOUND 1 can exist in a variety of solid forms. In one embodiment, provided herein are solid forms that include neat crystal forms. In another embodiment, provided herein are solid forms that include solvated forms and amorphous forms. The present disclosure provides certain solid forms of COMPOUND 1. In certain embodiments, the present disclosure provides compositions comprising COMPOUND 1 in a form described herein. In some embodiments of provided compositions, COMPOUND 1 is present as a mixture of one or more solid forms; in some embodiments of provided compositions, COMPOUND 1 is present in a single form.

In one embodiment, COMPOUND 1 is a single crystalline form, or any one of the single crystalline forms described herein. Synthesis of crystalline forms of COMPOUND 1 is described in the international application publication WO 2015/017821 published Feb. 5, 2015 and the U.S. provisional application Ser. No. 61/112,127, filed Feb. 4, 2015, both incorporated by reference herein in their entireties. Also provided are pharmaceutical compositions comprising at least one pharmaceutically acceptable carrier or diluent; and COMPOUND 1, wherein COMPOUND 1 is a single crystalline form, or any one of the crystalline forms being described herein. Also provided are uses of COMPOUND 1, wherein COMPOUND 1 is a single crystalline form, or any one of the single crystalline forms described herein, to prepare a pharmaceutical composition.

Provided herein is an assortment of characterizing information to describe the crystalline forms of COMPOUND 1. It should be understood, however, that not all such information is required for one skilled in the art to determine that such particular form is present in a given composition, but that the determination of a particular form can be achieved using any portion of the characterizing information that one skilled in the art would recognize as sufficient for establishing the presence of a particular form, e.g., even a single distinguishing peak can be sufficient for one skilled in the art to appreciate that such particular form is present.

In one embodiment, at least a particular percentage by weight of COMPOUND 1 is crystalline. Particular weight percentages may be 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 10% and 100%. When a particular percentage by weight of COMPOUND 1 is crystalline, the remainder of COMPOUND 1 is the amorphous form of COMPOUND 1. Non-limiting examples of crystalline COMPOUND 1 include a single crystalline form of compound 1 or a mixture of different single crystalline forms. In some embodiments, COMPOUND 1 is at least 75% by weight crystalline. In some embodiments, COMPOUND 1 is at least 80% by weight crystalline. In some embodiments, COMPOUND 1 is at least 83% by weight crystalline. In some embodiments, COMPOUND 1 is at least 85% by weight crystalline. In some embodiments, COMPOUND 1 is at least 87% by weight crystalline. In some embodiments, COMPOUND 1 is at least 90% by weight crystalline. In some embodiments, COMPOUND 1 is at least 93% by weight crystalline. In some other embodiments, COMPOUND 1 is at least 95% by weight crystalline. In some embodiments, COMPOUND 1 is at least 97% by weight crystalline. In some embodiments, COMPOUND 1 is at least 99% by weight crystalline.

In another embodiment, a particular percentage by weight of the crystalline COMPOUND 1 is a specific single crystalline form or a combination of single crystalline forms. Particular weight percentages may be 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 10% and 100%. In some embodiments, COMPOUND 1 is at least 75% by weight crystalline. In some embodiments, COMPOUND 1 is at least 80% by weight crystalline. In some embodiments, COMPOUND 1 is at least 83% by weight of a single crystalline form. In some embodiments, COMPOUND 1 is at least 85% by weight of a single crystalline form. In some embodiments, COMPOUND 1 is at least 87% by weight of a single crystalline form. In some embodiments, COMPOUND 1 is at least 90% by weight of a single crystalline form. In some embodiments, COMPOUND 1 is at least 93% by weight of a single crystalline form. In some other embodiments, COMPOUND 1 is at least 95% by weight of a single crystalline form. In some embodiments, COMPOUND 1 is at least 97% by weight of a single crystalline form. In some embodiments, COMPOUND 1 is at least 99% by weight of a single crystalline form.

In the following description of COMPOUND 1, embodiments of the invention may be described with reference to a particular crystalline form of COMPOUND 1, as characterized by one or more properties as discussed herein. The descriptions characterizing the crystalline forms may also be used to describe the mixture of different crystalline forms that may be present in a crystalline COMPOUND 1. However, the particular crystalline forms of COMPOUND 1 may also be characterized by one or more of the characteristics of the crystalline form as described herein, with or without regard to referencing a particular crystalline form.

The crystalline forms are further illustrated by the detailed descriptions and illustrative examples given below. The XRPD peaks described in Tables 1 to 6 may vary by ±0.2° depending upon the instrument used to obtain the data. The intensity of the XRPD peaks described in Tables 1 to 6 may vary by 10%.

Form 1

Figure 10:
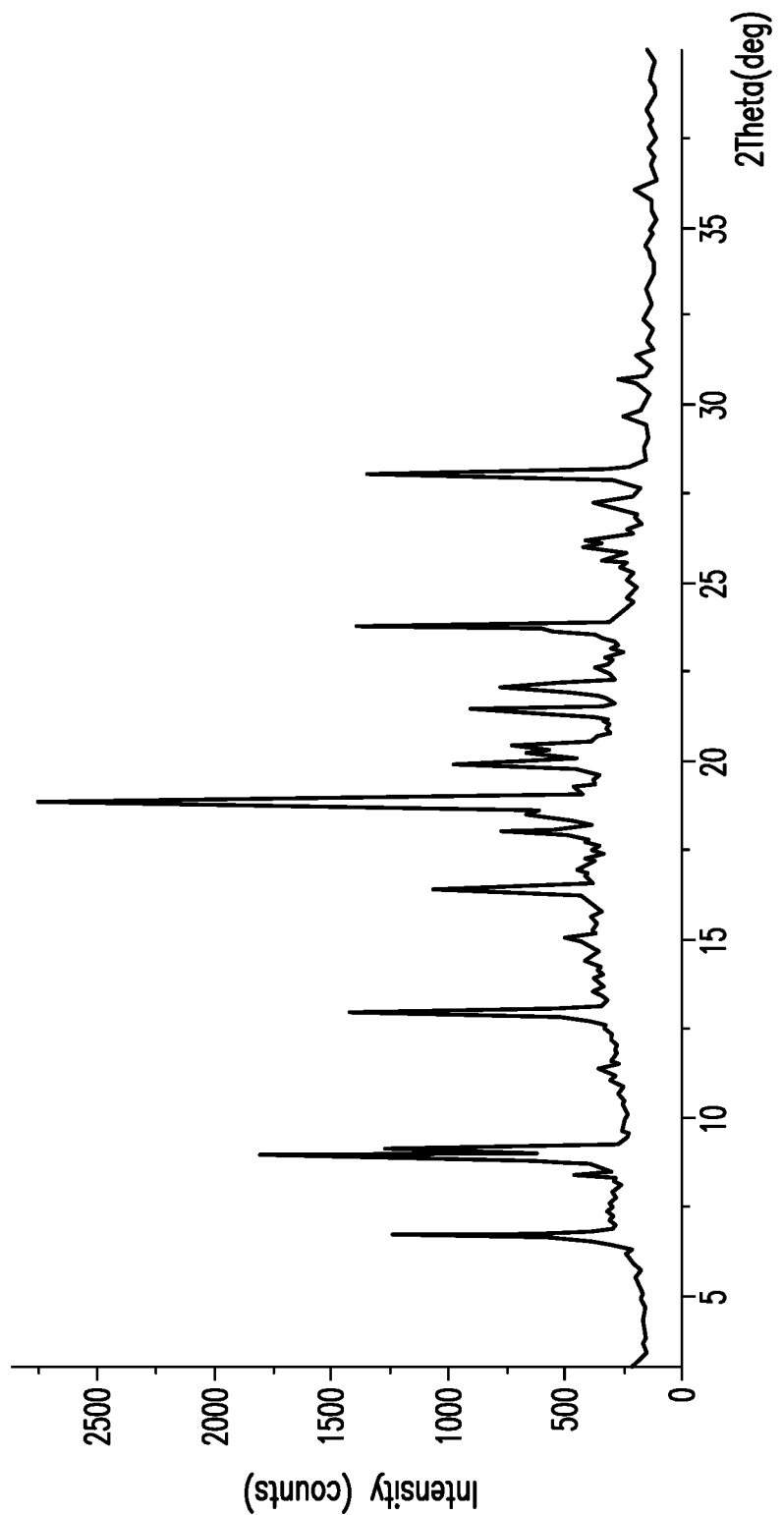
FIG. 10 is an X-ray powder diffractogram (XPRD) of COMPOUND 1 form 1.

In one embodiment, a single crystalline form, Form 1, of COMPOUND 1 is characterized by the X-ray powder diffraction (XRPD) pattern shown in FIG. 10, and data shown in Table 1 obtained using CuKα radiation. In a particular embodiment, the polymorph can be characterized by one or more of the peaks taken from FIG. 10, as shown in Table 1. For example, the polymorph can be characterized by one or two or three or four or five or six or seven or eight or nine of the peaks shown in Table 1.

TABLE 1

| Angle 2- | Intensity % |
| --- | --- |
| 6.7 | 42.2 |
| 8.9 | 61.8 |
| 9.1 | 41.9 |
| 13.0 | 46.7 |
| 16.4 | 33.2 |
| 18.9 | 100.0 |
| 21.4 | 27.3 |
| 23.8 | 49.2 |
| 28.1 | 47.5 |

In another embodiment, Form 1 can be characterized by the peaks identified at 2θ angles of 8.9, 13.0, 18.9, 23.8, and 28.10. In another embodiment, Form 1 can be characterized by the peaks identified at 2θ angles of 8.9, 18.9, and 23.8°.

Form 2

Figure 11:
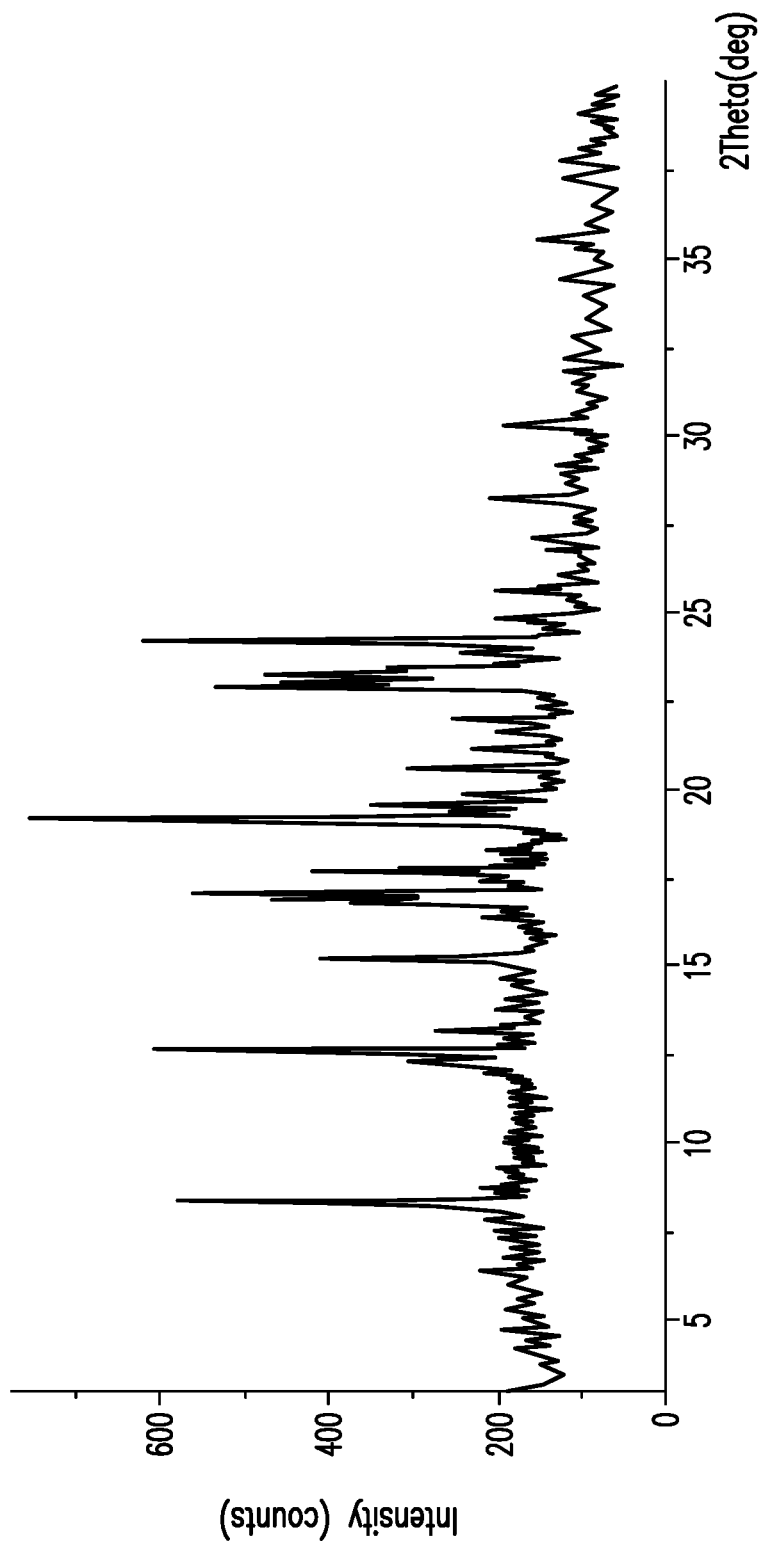
FIG. 11 is an X-ray powder diffractogram (XPRD) of COMPOUND 1 form 2.

In one embodiment, a single crystalline form, Form 2, of COMPOUND 1 is characterized by the X-ray powder diffraction (XRPD) pattern shown in FIG. 11, and data shown in Table 2, obtained using CuKα radiation. In a particular embodiment, the polymorph can be characterized by one or more of the peaks taken from FIG. 11, as shown in Table 2. For example, the polymorph can be characterized by one or two or three or four or five or six or seven or eight or nine of the peaks shown in Table 2.

TABLE 2

| Angle 2- | Intensity % |
| --- | --- |
| 8.4 | 65.2 |
| 12.7 | 75.5 |
| 16.9 | 57.9 |
| 17.1 | 69.4 |
| 17.7 | 48.6 |
| 19.2 | 100.0 |
| 23.0 | 69.7 |
| 23.3 | 61.1 |
| 24.2 | 87.3 |

In another embodiment, Form 2 can be characterized by the peaks identified at 2θ angles of 12.7, 17.1, 19.2, 23.0, and 24.2°. In another embodiment, Form 2 can be characterized by the peaks identified at 2θ angles of 12.7, 19.2, and 24.2°.

Form 3

Figure 12:
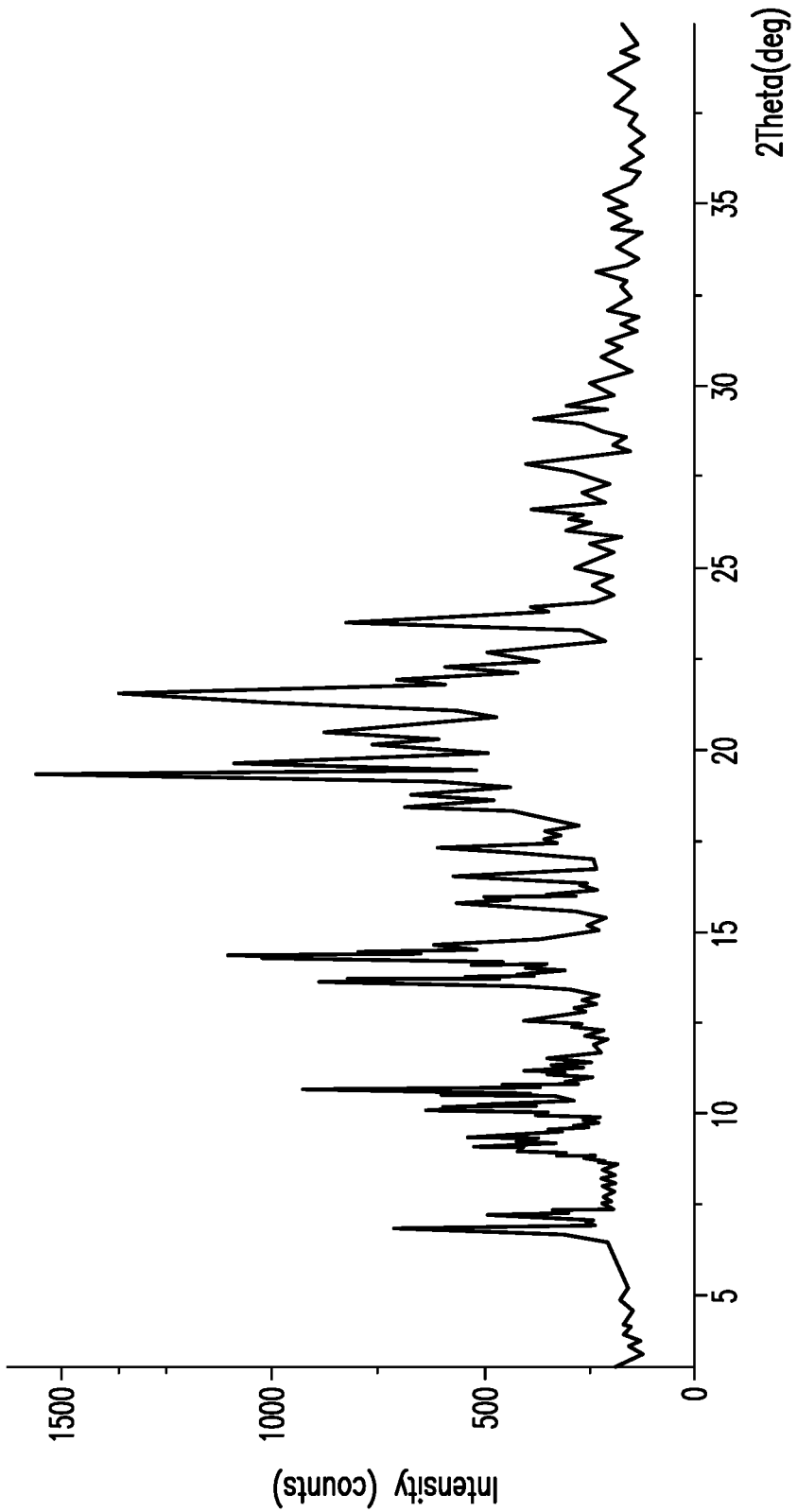
FIG. 12 is an X-ray powder diffractogram (XPRD) of COMPOUND 1 form 3.

In one embodiment, a single crystalline form, Form 3, of COMPOUND 1 is characterized by the X-ray powder diffraction (XRPD) pattern shown in FIG. 12, and data shown in Table 3, obtained using CuKα radiation. In a particular embodiment, the polymorph can be characterized by one or more of the peaks taken from FIG. 12, as shown in Table 3. For example, the polymorph can be characterized by one or two or three or four or five or six or seven or eight or nine of the peaks shown in Table 3.

TABLE 3

| Angle 2- | Intensity % |
| --- | --- |
| 6.8 | 35.5 |
| 10.1 | 30.7 |
| 10.6 | 53.1 |
| 13.6 | 46.0 |
| 14.2 | 63.8 |
| 17.2 | 26.4 |
| 18.4 | 34.0 |
| 19.2 | 100.0 |
| 23.5 | 3.8 |

In another embodiment, Form 3 can be characterized by the peaks identified at 2θ angles of 6.8, 10.6, 13.6, 14.2, and 19.2°. In another embodiment, Form 3 can be characterized by the peaks identified at 2θ angles of 10.6, 14.2, and 19.2°.

Form 4

Figure 13:
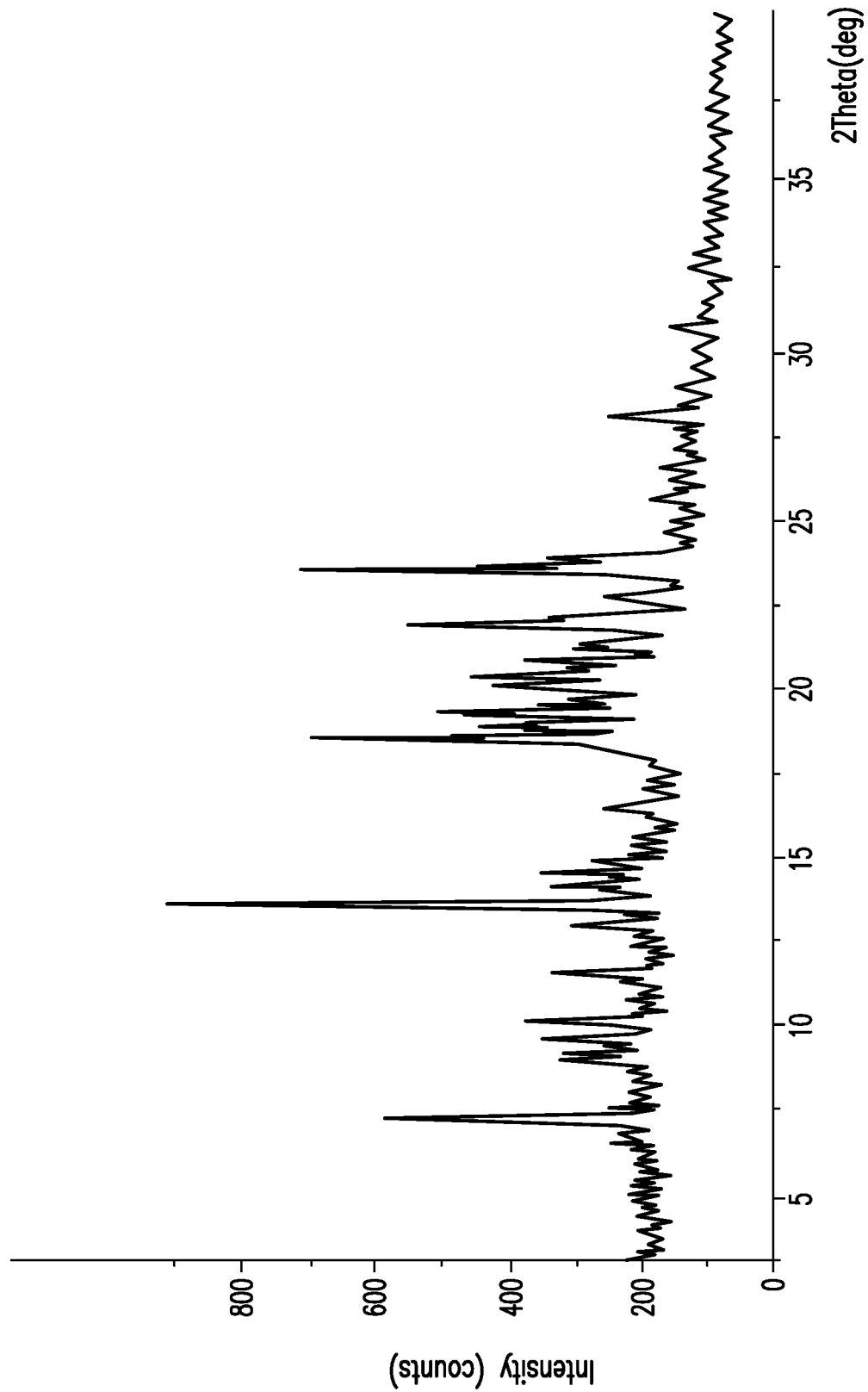
FIG. 13 is an X-ray powder diffractogram (XPRD) of COMPOUND 1 form 4.

In one embodiment, a single crystalline form, Form 4, of COMPOUND 1 is characterized by the X-ray powder diffraction (XRPD) pattern shown in FIG. 13, and data shown in Table 4, obtained using CuKα radiation. In a particular embodiment, the polymorph can be characterized by one or more of the peaks taken from FIG. 13, as shown in Table 4. For example, the polymorph can be characterized by one or two or three or four or five or six or seven or eight or nine of the peaks shown in Table 4.

TABLE 4

| Angle 2- | Intensity % |
| --- | --- |
| 7.2 | 53.3 |
| 10.1 | 26.7 |
| 11.5 | 20.5 |
| 13.6 | 100.0 |
| 18.5 | 72.0 |
| 19.3 | 46.9 |
| 20.3 | 39.4 |
| 21.9 | 55.4 |
| 23.5 | 77.5 |

In another embodiment, Form 4 can be characterized by the peaks identified at 2θ angles of 7.2, 13.6, 18.5, 19.3, 21.9, and 23.5°. In another embodiment, Form 4 can be characterized by the peaks identified at 2θ angles of 13.6, 18.5, and 23.5°.

Form 5

Figure 14:
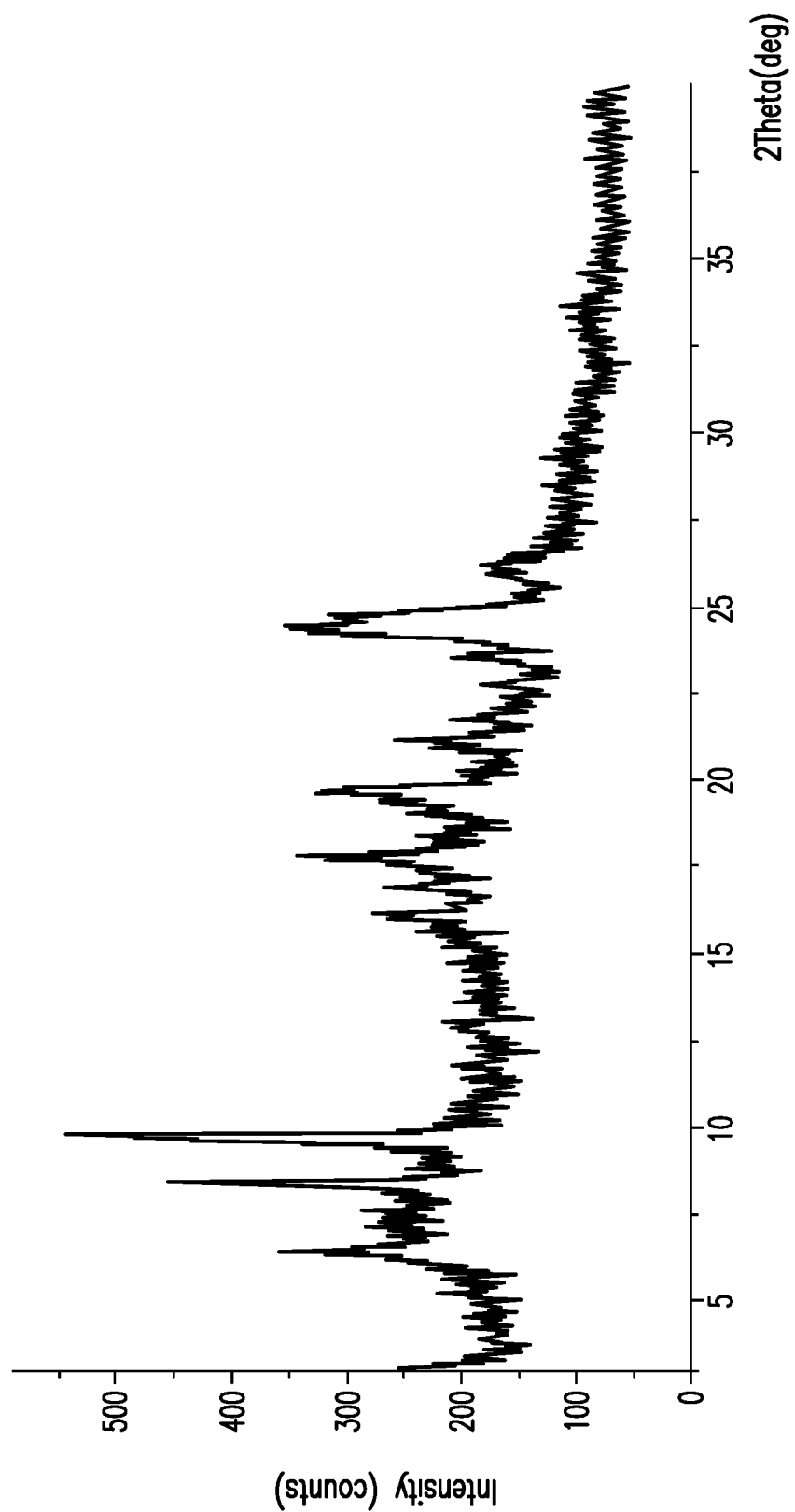
FIG. 14 is an X-ray powder diffractogram (XPRD) of COMPOUND 1 form 5.

In one embodiment, a single crystalline form, Form 5, of COMPOUND 1 is characterized by the X-ray powder diffraction (XRPD) pattern shown in FIG. 14, and data shown in Table 5, obtained using CuKα radiation. In a particular embodiment, the polymorph can be characterized by one or more of the peaks taken from FIG. 14, as shown in Table 5. For example, the polymorph can be characterized by one or two or three or four or five or six or seven or eight or nine of the peaks shown in Table 5.

TABLE 5

| Angle 2- | Intensity % |
| --- | --- |
| 6.4 | 45.4 |
| 8.4 | 84.0 |
| 9.8 | 100.0 |
| 16.1 | 26.0 |
| 16.9 | 22.7 |

TABLE 5-continued

| Angle 2- | Intensity % |
|---|---|
| 17.8 | 43.6 |
| 19.7 | 40.4 |
| 21.1 | 20.5 |
| 26.1 | 15.9 |

In another embodiment, Form 5 can be characterized by the peaks identified at 2θ angles of 6.4, 8.4, 9.8, 17.8, and 19.7°. In another embodiment, Form 5 can be characterized by the peaks identified at 2θ angles of 8.4 and 9.8°.

Form 6

Figure 15:
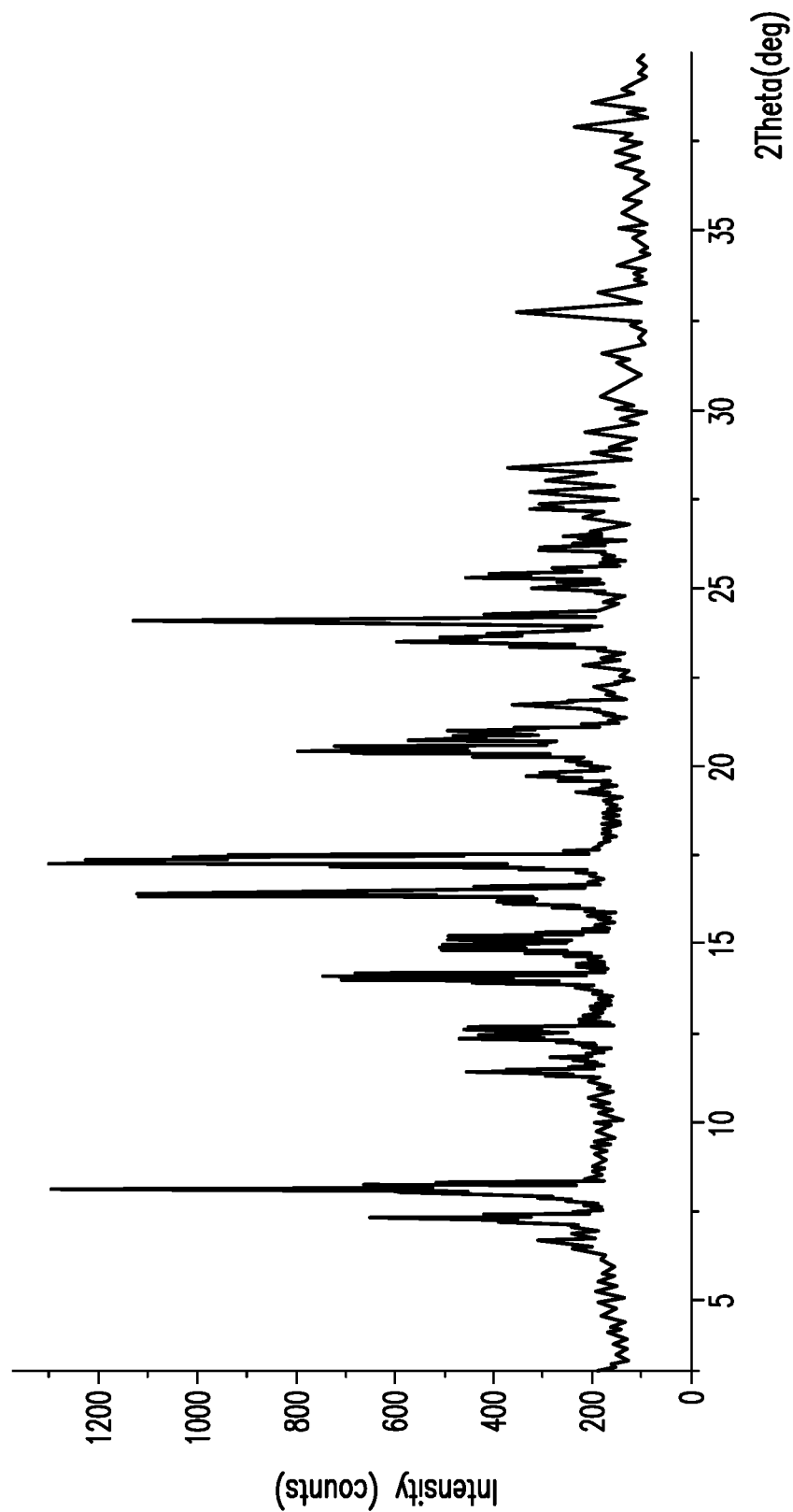
FIG. 15 is an X-ray powder diffractogram (XPRD) of COMPOUND 1 form 6.

In one embodiment, a single crystalline form, Form 6, of COMPOUND 1 is characterized by the X-ray powder diffraction (XRPD) pattern shown in FIG. 15, and data shown in Table 6, obtained using CuKα radiation. In a particular embodiment, the polymorph can be characterized by one or more of the peaks taken from FIG. 15, as shown in Table 6. For example, the polymorph can be characterized by one or two or three or four or five or six or seven or eight of the peaks shown in Table 6.

TABLE 6

| Angle 2- | Intensity % |
|---|---|
| 8.1 | 97.9 |
| 11.4 | 24.9 |
| 14.1 | 51.5 |
| 15.2 | 28.4 |
| 16.4 | 85.0 |
| 17.3 | 100.0 |
| 20.5 | 54.7 |
| 24.1 | 88.7 |

In another embodiment, Form 6 can be characterized by the peaks identified at 2θ angles of 8.1, 14.1, 16.4, 17.3, 20.5, and 24.1°. In another embodiment, Form 6 can be characterized by the peaks identified at 2θ angles of 8.1, 16.4, 17.3, and 24.10.

DNA Demethylating Agents

In one embodiment, the methods provided herein comprise administration or co-administration of one or more DNA demethylating agents. In one embodiment, the DNA demethylating agents are cytidine analogs. In certain embodiments, the cytidine analog is azacitidine) or 5-aza-2'-deoxycytidine (decitabine). In certain embodiments, the cytidine analog is azacitidine. In certain embodiments, the cytidine analog is 5-aza-2'-deoxycytidine (decitabine). In certain embodiments, the cytidine analog is, for example: 1-β-D-arabinofuranosylcytosine (Cytarabine or ara-C); pseudoiso-cytidine (psi ICR); 5-fluoro-2'-deoxycytidine (FCdR); 2'-deoxy-2',2'-difluorocytidine (Gemcitabine); 5-aza-2'-deoxy-2',2'-difluorocytidine; 5-aza-2'-deoxy-2'-fluorocytidine; 1-β-D-ribofuranosyl-2(1H)-pyrimidinone (Zebularine); 2',3'-dideoxy-5-fluoro-3'-thiacytidine (Emtriva); 2'-cyclocytidine (Ancitabine); 1-3-D-arabinofuranosyl-5-azacytosine (Fazarabine or ara-AC); 6-azacitidine (6-aza-CR); 5,6-dihydro-5-azacitidine (dH-aza-CR); $N^4$-pentyloxy-carbonyl-5'-deoxy-5-fluorocytidine (Capecitabine); $N^4$-octadecyl-cytarabine; or elaidic acid cytarabine. In certain embodiments, the cytidine analogs include any compound which is structurally related to cytidine or deoxycytidine and functionally mimics and/or antagonizes the action of cytidine or deoxycytidine.

In certain embodiments, exemplary cytidine analogs have the structures provided below:

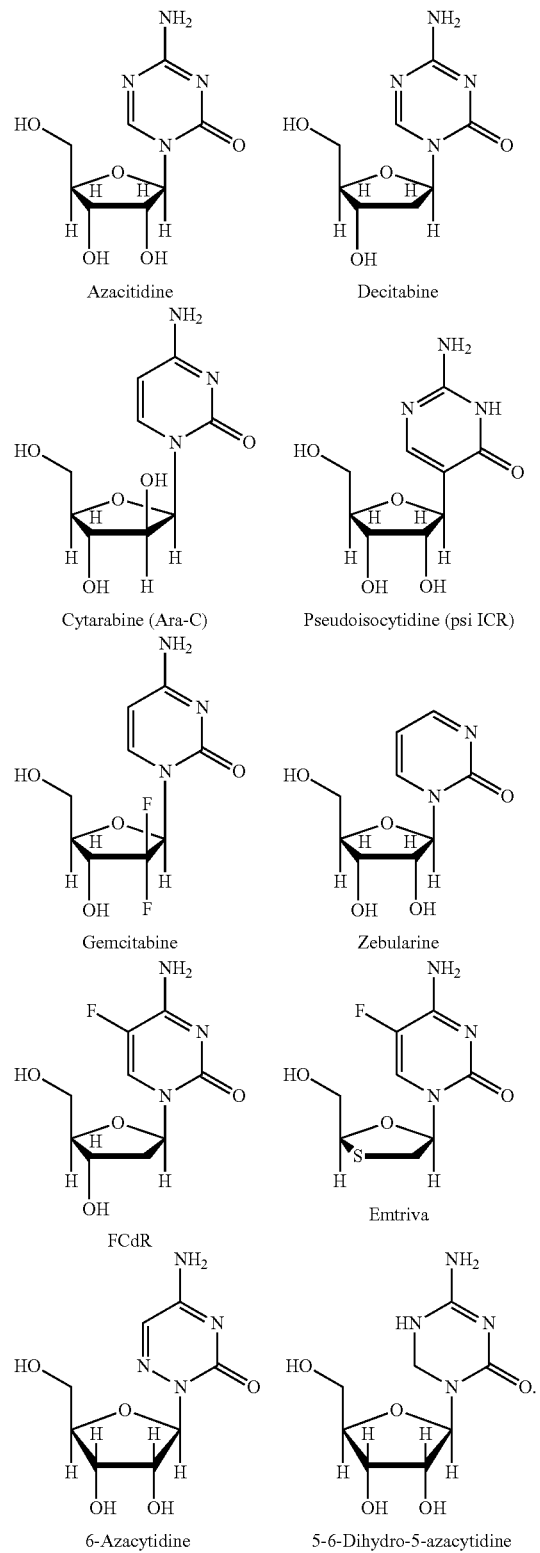

Cytidine analogs for use in the methods provided herein may be prepared using synthetic methods and procedures referenced herein or otherwise available in the literature. For example, particular methods for synthesizing azacitidine and decitabine are disclosed, e.g., in U.S. Pat. No. 7,038,038 and references discussed therein, each of which is incorporated herein by reference. Other cytidine analogs for use in the methods provided herein may be prepared, e.g., using procedures known in the art, or may be purchased from a commercial source. In one embodiment, the cytidine analogs for use in the methods provided herein may be prepared in a particular solid form (e.g., amorphous or crystalline form). See, e.g., U.S. Pat. No. 6,887,855, issued May 8, 2005 and U.S. Pat. No. 6,943,249, issued Sep. 13, 2005, both of which are incorporated herein by reference in their entireties.

In one embodiment, the cytidine analogs used in the methods provided herein is a free base, or a pharmaceutically acceptable salt or solvate thereof. In one embodiment, the free base or the pharmaceutically acceptable salt or solvate is a solid. In another embodiment, the free base or the pharmaceutically acceptable salt or solvate is a solid in an amorphous form. In yet another embodiment, the free base or the pharmaceutically acceptable salt or solvate is a solid in a crystalline form. For example, particular embodiments provide azacitidine and decitabine in solid forms, which can be prepared, for example, according to the methods described in U.S. Pat. Nos. 6,887,855; 6,943,249; 7,038,038; 7,078,518; 7,192,781; 7,772,199 and U.S. Patent Application Publication Nos. 2005/027675, each of which is incorporated by reference herein in their entireties. In other embodiments, azacitidine and decitabine in solid forms can be prepared using other methods known in the art.

In one embodiment, cytidine analogs used in the methods provided herein is a pharmaceutically acceptable salt of the cytidine analog, which includes, but is not limited to, acetate, adipate, alginate, aspartate, benzoate, benzenesulfonate (besylate), bisulfate, butyrate, citrate, camphorate, camphorsulfonate, cyclopentanepropionate, digluconate, dodecylsulfate, 1,2-ethanedisulfonate (edisylate), ethanesulfonate (esylate), formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate (mesylate), 2-naphthalenesulfonate (napsylate), nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate, or undecanoate salts.

Azacitidine is 4-amino-1-O-D-ribofuranozyl-s-triazin-2 (1H)-one, also known as VIDAZA® (Celgene Corporation). Its empirical formula is $C_8H_{12}N_4O_5$, the molecular weight is 244. Azacitidine is a white to off-white solid that is insoluble in acetone, ethanol and methyl ketone; slightly soluble in ethanol/water (50/50), propylene glycol and polyethylene glycol; sparingly soluble in water, water-saturated octanol, 5% dextrose in water, N-methyl-2-pyrrolidone, normal saline and 5% Tween 80 in water, and soluble in dimethylsulfoxide (DMSO).

VIDAZA® is approved for treatment in patients with higher-risk MDS. It is supplied in a sterile form for reconstitution as a suspension for subcutaneous injection or reconstitution as a solution with further dilution for intravenous infusion. Vials of VIDAZA® contain 100 mg of azacitidine and 100 mg of mannitol as a sterile lyophilized powder. The approved dosing schedule is a twice-daily subcutaneous injection or a single daily intravenous infusion on seven consecutive days of a 28-day treatment cycle.

Oral azacitidine is effective and safe in lower-risk myelodysplastic syndrome (MDS) and acute myeloid leukemia (AML) patients. In one embodiment, the dose used in MDS and AML patients is 300 mg once daily based on extended dosing (14 or 21 days of the 28-day treatment cycle). In one embodiment, the starting dose for oral azacitidine is 120 mg and the maximum tolerated dose is 480 mg.

Decitabine is 4-amino-1-(2-deoxy-β-D-erythro-pentofuranosyl)-1,3,5-triazin-2(1H)one, also known as DACOGEN®. Its empirical formula is $C_8H_{12}N_4O_4$, the molecular weight is 228.21. Decitabine is a fine, white to almost white powder that is slightly soluble in ethanol/water (50/50), methanol/water (50/50) and methanol; sparingly soluble in water, and soluble in dimethylsulfoxide (DMSO).

DACOGEN™ is approved for treatment in patients with myelodysplastic syndromes. It is supplied in a clear colorless glass vial as white sterile lyophilized powder for injection. Each 20 mL, as a single dose, glass vial contains 50 mg decitabine, 68 mg monobasic potassium phosphate (potassium dihydrogen phosphate) and 11.6 mg sodium hydrochloride.

Compositions and Routes of Administration

In one embodiment, provided herein is a pharmaceutical composition comprising a therapeutically effective amount of a mutant IDH2 inhibitor and a DNA demethylating agent. In one embodiment, the mutant IDH2 inhibitor is COMPOUND 1.

In one embodiment, provided herein is a pharmaceutical composition comprising a therapeutically effective amount of COMPOUND 1 and azacitidine.

In one embodiment, COMPOUND 1 and azacitidine are formulated as one composition. In another embodiment, COMPOUND 1 and azacitidine are formulated as separate compositions.

In one embodiment, the compounds utilized in the methods provided herein may be formulated together with a pharmaceutically acceptable carrier or adjuvant into pharmaceutically acceptable compositions prior to be administered to a subject. In another embodiment, such pharmaceutically acceptable compositions further comprise additional therapeutic agents in amounts effective for achieving a modulation of disease or disease symptoms, including those described herein.

Pharmaceutically acceptable carriers, adjuvants and vehicles that may be used in the pharmaceutical compositions of one aspect of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of COMPOUND 1 described herein.

In one embodiment, the pharmaceutical composition comprises COMPOUND 1 and an excipient. In one embodiment, the pharmaceutical composition that comprises COMPOUND 1 and an excipient, is for oral administration. In one embodiment, the excipient is a diluent, a binder, a disintegrant, a wetting agent, a stabilizer, a glidant, and/or a lubricant. In one embodiment, the excipient is a diluent. In one embodiment, the excipient is a binder. In one embodiment, the excipient is a disintegrant. In one embodiment, the excipient is a wetting agent. In one embodiment, the excipient is a stabilizer. In one embodiment, the excipient is a glidant. In one embodiment, the excipient is a lubricant.

In one embodiment, the diluent is a microcrystalline cellulose.

In one embodiment, the binder is a hydroxypropyl cellulose.

In one embodiment, the disintegrant is sodium starch glycolate.

In one embodiment, the wetting agent is sodium lauryl sulfate.

In one embodiment, the stabilizer is hypromellose acetate succinate.

In one embodiment, the glidant is colloidal silicon dioxide.

In one embodiment, the lubricant is magnesium stearate.

In one embodiment, the pharmaceutical composition comprises COMPOUND 1 and/or azacitidine and an excipient. In one embodiment, the pharmaceutical composition that comprises COMPOUND 1 and/or azacitidine and an excipient, is for oral administration.

Oral delivery formats for COMPOUND 1 and/or azacitidine include, but are not limited to, tablets, capsules, caplets, solutions, suspensions, and syrups, and may also comprise a plurality of granules, beads, powders or pellets that may or may not be encapsulated. Such formats may also be referred to herein as the "drug core" which contains COMPOUND 1 and/or azacitidine.

Particular embodiments herein provide solid oral dosage forms that are tablets or capsules. In certain embodiments, the formulation is a tablet comprising COMPOUND 1 and/or azacitidine. In certain embodiments, the formulation is a capsule comprising COMPOUND 1 and/or azacitidine. In certain embodiments, the tablets or capsules provided herein optionally comprise one or more excipients, such as, for example, glidants, diluents, lubricants, colorants, disintegrants, granulating agents, binding agents, polymers, and coating agents. In certain embodiments, the formulation is an immediate release tablet. In certain embodiments, the formulation is a controlled release tablet releasing the active pharmaceutical ingredient (API), e.g., substantially in the stomach. In certain embodiments, the formulation is a hard gelatin capsule. In certain embodiments, the formulation is a soft gelatin capsule. In certain embodiments, the capsule is a hydroxypropyl methylcellulose (HPMC) capsule. In certain embodiments, the formulation is an immediate release capsule. In certain embodiments, the formulation is an immediate or controlled release capsule releasing the API, e.g., substantially in the stomach. In certain embodiments, the formulation is a rapidly disintegrating tablet that dissolves substantially in the mouth following administration. In certain embodiments, embodiments herein encompass the use of COMPOUND 1 and/or azacitidine for the preparation of a pharmaceutical composition for treating a malignancy, characterized by the presence of a mutant allele of IDH2, wherein the composition is prepared for oral administration.

Particular embodiments herein provide pharmaceutical formulations (e.g., immediate release oral formulations and/or formulations that release the API substantially in the stomach) comprising COMPOUND 1 and/or azacitidine that achieve a particular AUC value (e.g., AUC(0-t) or AUC(0-∞)) in the subject (e.g., human) to which the formulation is orally administered. Particular embodiments provide oral formulations that achieve an AUC value of at least about 25 ng-hr/mL, at least about 50 ng-hr/mL, at least about 75 ng-hr/mL, at least about 100 ng-hr/mL, at least about 150 ng-hr/mL, at least about 200 ng-hr/mL, at least about 250 ng-hr/mL, at least about 300 ng-hr/mL, at least about 350 ng-hr/mL, at least about 400 ng-hr/mL, at least about 450 ng-hr/mL, at least about 500 ng-hr/mL, at least about 550 ng-hr/mL, at least about 600 ng-hr/mL, at least about 650 ng-hr/mL, at least about 700 ng-hr/mL, at least about 750 ng-hr/mL, at least about 800 ng-hr/mL, at least about 850 ng-hr/mL, at least about 900 ng-hr/mL, at least about 950 ng-hr/mL, at least about 1000 ng-hr/mL, at least about 1100 ng-hr/mL, at least about 1200 ng-hr/mL, at least about 1300 ng-hr/mL, at least about 1400 ng-hr/mL, at least about 1500 ng-hr/mL, at least about 1600 ng-hr/mL, at least about 1700 ng-hr/mL, at least about 1800 ng-hr/mL, at least about 1900 ng-hr/mL, at least about 2000 ng-hr/mL, at least about 2250 ng-hr/mL, or at least about 2500 ng-hr/mL. In particular embodiments, the AUC determination is obtained from a time-concentration pharmacokinetic profile obtained from the blood samples of animals or human volunteers following dosing.

Particular embodiments herein provide pharmaceutical formulations (e.g., immediate release oral formulations and/or formulations that release the API substantially in the stomach) comprising COMPOUND 1 and/or azacitidine that achieve a particular maximum plasma concentration ("Cmax") in the subject to which the formulation is orally administered. Particular embodiments provide oral formulations that achieve a Cmax of the COMPOUND 1 and/or citidine analog of at least about 25 ng/mL, at least about 50 ng/mL, at least about 75 ng/mL, at least about 100 ng/mL, at least about 150 ng/mL, at least about 200 ng/mL, at least about 250 ng/mL, at least about 300 ng/mL, at least about 350 ng/mL, at least about 400 ng/mL, at least about 450 ng/mL, at least about 500 ng/mL, at least about 550 ng/mL, at least about 600 ng/mL, at least about 650 ng/mL, at least about 700 ng/mL, at least about 750 ng/mL, at least about 800 ng/mL, at least about 850 ng/mL, at least about 900 ng/mL, at least about 950 ng/mL, at least about 1000 ng/mL, at least about 1100 ng/mL, at least about 1200 ng/mL, at least about 1300 ng/mL, at least about 1400 ng/mL, at least about 1500 ng/mL, at least about 1600 ng/mL, at least about 1700 ng/mL, at least about 1800 ng/mL, at least about 1900 ng/mL, at least about 2000 ng/mL, at least about 2250 ng/mL, or at least about 2500 ng/mL.

Particular embodiments herein provide pharmaceutical formulations (e.g., immediate release oral formulations and/or formulations that release the API substantially in the stomach) comprising COMPOUND 1 and/or azacitidine that achieve a particular time to maximum plasma concentration ("Tmax") in the subject to which the formulation is orally administered. Particular embodiments provide oral formulations that achieve a Tmax of the cytidine analog of less than about 10 min., less than about 15 min., less than about 20 min., less than about 25 min., less than about 30 min., less than about 35 min., less than about 40 min., less than about 45 min., less than about 50 min., less than about 55 min., less than about 60 min., less than about 65 min., less than about 70 min., less than about 75 min., less than about 80 min., less than about 85 min., less than about 90 min., less than about 95 min., less than about 100 min., less than about 105 min., less than about 110 min., less than about 115 min., less than about 120 min., less than about 130 min., less than about 140 min., less than about 150 min., less than about 160 min., less than about 170 min., less than about 180 min., less than about 190 min., less than about 200 min., less than about 210 min., less than about 220 min., less than about 230 min., or less than about 240 min. In particular embodiments, the Tmax value is measured from the time at which the formulation is orally administered.

Particular embodiments herein provide oral dosage forms comprising COMPOUND 1 and/or azacitidine wherein the oral dosage forms have an enteric coating. Particular embodiments provide a permeable or partly permeable (e.g., "leaky") enteric coating with pores. In particular embodiments, the permeable or partly permeable enteric-coated tablet releases the COMPOUND 1 and/or azacitidine in an immediate release manner substantially in the stomach.

Provided herein are dosage forms designed to maximize the absorption and/or efficacious delivery of COMPOUND 1 and/or azacytidine, upon oral administration, e.g., for release substantially in the stomach. Accordingly, certain embodiments herein provide a solid oral dosage form of COMPOUND 1 and/or azacitidine using pharmaceutical excipients designed for immediate release of the API upon oral administration, e.g., substantially in the stomach. Particular immediate release formulations comprise a specific amount of COMPOUND 1 and/or azacitidine and optionally one or more excipients. In certain embodiments, the formulation may be an immediate release tablet or an immediate release capsule (such as, e.g., an HPMC capsule).

Provided herein are methods of making the formulations provided herein comprising COMPOUND 1 and/or azacitidine provided herein (e.g., immediate release oral formulations and/or formulations that release the API substantially in the stomach). In particular embodiments, the formulations provided herein may be prepared using conventional methods known to those skilled in the field of pharmaceutical formulation, as described, e.g., in pertinent textbooks. See, e.g., REMINGTON, THE SCIENCE AND PRACTICE OF PHARMACY, 20th Edition, Lippincott Williams & Wilkins, (2000); ANSEL et al., PHARMACEUTICAL DOSAGE FORMS AND DRUG DELIVERY SYSTEMS, 7th Edition, Lippincott Williams & Wilkins, (1999); GIBSON, PHARMACEUTICAL PREFORMULATION AND FORMULATION, CRC Press (2001).

In particular embodiments, formulations provided herein (e.g., immediate release oral formulations, formulations that release the API substantially in the stomach, or rapidly disintegrating formulations that dissolve substantially in the mouth) comprise COMPOUND 1 and/or azacitidine in a specific amount. In particular embodiments, the specific amount of COMPOUND 1 and/or azacitidine in the formulation is, e.g., about 10 mg. In one embodiment, the specific amount is about 20 mg. In one embodiment, the specific amount is about 40 mg. In one embodiment, the specific amount is about 60 mg. In one embodiment, the specific amount is about 80 mg. In one embodiment, the specific amount is about 100 mg. In one embodiment, the specific amount is about 120 mg. In one embodiment, the specific amount is about 140 mg. In one embodiment, the specific amount is about 160 mg. In one embodiment, the specific amount is about 180 mg. In one embodiment, the specific amount is about 200 mg. In one embodiment, the specific amount is about 220 mg. In one embodiment, the specific amount is about 240 mg. In one embodiment, the specific amount is about 260 mg. In one embodiment, the specific amount is about 280 mg. In one embodiment, the specific amount is about 300 mg. In one embodiment, the specific amount is about 320 mg. In one embodiment, the specific amount is about 340 mg. In one embodiment, the specific amount is about 360 mg. In one embodiment, the specific amount is about 380 mg. In one embodiment, the specific amount is about 400 mg. In one embodiment, the specific amount is about 420 mg. In one embodiment, the specific amount is about 440 mg. In one embodiment, the specific amount is about 460 mg. In one embodiment, the specific amount is about 480 mg. In one embodiment, the specific amount is about 500 mg. In one embodiment, the specific amount is about 600 mg. In one embodiment, the specific amount is about 700 mg. In one embodiment, the specific amount is about 800 mg. In one embodiment, the specific amount is about 900 mg. In one embodiment, the specific amount is about 1000 mg. In one embodiment, the specific amount is about 1100 mg. In one embodiment, the specific amount is about 1200 mg. In one embodiment, the specific amount is about 1300 mg. In one embodiment, the specific amount is about 1400 mg. In one embodiment, the specific amount is about 1500 mg. In one embodiment, the specific amount is about 1600 mg. In one embodiment, the specific amount is about 1700 mg. In one embodiment, the specific amount is about 1800 mg. In one embodiment, the specific amount is about 1900 mg. In one embodiment, the specific amount is about 2000 mg. In one embodiment, the specific amount is about 2100 mg. In one embodiment, the specific amount is about 2200 mg. In one embodiment, the specific amount is about 2300 mg. In one embodiment, the specific amount is about 2400 mg. In one embodiment, the specific amount is about 2500 mg. In one embodiment, the specific amount is about 3000 mg. In one embodiment, the specific amount is about 4000 mg. In one embodiment, the specific amount is about 5000 mg.

In certain embodiments, the formulation is a tablet, wherein the tablet is manufactured using standard, art-recognized tablet processing procedures and equipment. In certain embodiments, the method for forming the tablets is direct compression of a powdered, crystalline and/or granular composition comprising COMPOUND 1 and/or azacitidine alone or in combination with one or more excipients, such as, for example, carriers, additives, polymers, or the like. In certain embodiments, as an alternative to direct compression, the tablets may be prepared using wet granulation or dry granulation processes. In certain embodiments, the tablets are molded rather than compressed, starting with a moist or otherwise tractable material. In certain embodiments, compression and granulation techniques are used.

In certain embodiments, the formulation is a capsule, wherein the capsules may be manufactured using standard, art-recognized capsule processing procedures and equipments. In certain embodiments, soft gelatin capsules may be prepared in which the capsules contain a mixture of COMPOUND 1 and/or the cytidine analog and vegetable oil or non-aqueous, water miscible materials such as, for example, polyethylene glycol and the like. In certain embodiments, hard gelatin capsules may be prepared containing granules of COMPOUND 1 and/or the cytidine analog in combination with a solid pulverulent carrier, such as, for example, lactose, saccharose, sorbitol, mannitol, potato starch, corn starch, amylopectin, cellulose derivatives, or gelatin. In certain embodiments, a hard gelatin capsule shell may be prepared from a capsule composition comprising gelatin and a small amount of plasticizer such as glycerol. In certain embodiments, as an alternative to gelatin, the capsule shell may be made of a carbohydrate material. In certain embodiments, the capsule composition may additionally include polymers, colorings, flavorings and opacifiers as required. In certain embodiments, the capsule comprises HPMC.

In certain embodiments, the formulation of COMPOUND 1 and/or azacitidine is prepared using aqueous solvents without causing significant hydrolytic degradation of azacitidine. In particular embodiments, the formulation of COMPOUND 1 and/or azacitidine is a tablet which contains a coating applied to the drug core using aqueous solvents without causing significant hydrolytic degradation of azacitidine in the formulation. In certain embodiments, water is employed as the solvent for coating the drug core. In certain embodiments, the oral dosage form of COMPOUND 1 and/or azacitidine is a tablet containing a film coat applied to the drug core using aqueous solvents. In particular embodiments, water is employed as the solvent for film-coating. In particular embodiments, the tablet containing COMPOUND 1 and/or azacitidine is film-coated using aqueous solvents without effecting degradation of the pharmaceutical composition. In particular embodiments, water is used as the film coating solvent without effecting degradation of the pharmaceutical composition. In certain embodiments, an oral dosage form comprising COMPOUND 1 and/or azacitidine and an aqueous film coating effects immediate drug release upon oral delivery. In certain embodiments, the oral dosage form comprising COMPOUND 1 and/or azacitidine and an aqueous film coating effects controlled drug release to the upper gastrointestinal tract, e.g., the stomach, upon oral administration. In particular embodiments, a tablet with an aqueous-based film coating comprises COMPOUND 1 and/or azacytidine as the API.

In certain embodiments, provided herein is a controlled release pharmaceutical formulation for oral administration of azacitidine that releases COMPOUND 1 and/or azacitidine substantially in the stomach, comprising: a) a specific amount of COMPOUND 1 and/or azacitidine; b) a drug release controlling component for controlling the release of COMPOUND 1 and/or azacitidine substantially in the upper gastrointestinal tract, e.g., the stomach; and c) optionally one or more excipients. In certain embodiments, the oral dosage form comprising COMPOUND 1 and/or azacitidine is prepared as a controlled release tablet or capsule which includes a drug core comprising the pharmaceutical composition and optional excipients. Optionally, a "seal coat" or "shell" is applied. In certain embodiments, a formulation provided herein comprising COMPOUND 1 and/or azacitidine provided herein is a controlled release tablet or capsule, which comprises a therapeutically effective amount of COMPOUND 1 and/or azacitidine, a drug release controlling component that controls the release of COMPOUND 1 and/or azacitidine substantially in the stomach upon oral administration, and optionally, one or more excipients.

Particular embodiments provide a drug release controlling component that is a polymer matrix, which swells upon exposure to gastric fluid to effect the gastric retention of the formulation and the sustained release of COMPOUND 1 and/or azacitidine from the polymer matrix substantially in the stomach. In certain embodiments, such formulations may be prepared by incorporating COMPOUND 1 and/or azacitidine into a suitable polymeric matrix during formulation. Examples of such formulations are known in the art. See, e.g., Shell et al., U.S. Patent Publication No. 2002/0051820 (application Ser. No. 09/990,061); Shell et al., U.S. Patent Publication No. 2003/0039688 (application Ser. No. 10/045,823); Gusler et al., U.S. Patent Publication No. 2003/0104053 (application Ser. No. 10/029,134), each of which is incorporated herein by reference in its entirety.

In certain embodiments, the drug release controlling component may comprise a shell surrounding the drug-containing core, wherein the shell releases COMPOUND 1 and/or azacitidine from the core by, e.g., permitting diffusion of COMPOUND 1 and/or azacitidine from the core and promoting gastric retention of the formulation by swelling upon exposure to gastric fluids to a size that is retained in the stomach. In certain embodiments, such formulations may be prepared by first compressing a mixture of COMPOUND 1 and/or azacitidine and one or more excipients to form a drug core, and compressing another powdered mixture over the drug core to form the shell, or enclosing the drug core with a capsule shell made of suitable materials. Examples of such formulations are known in the art. See, e.g., Berner et al., U.S. Patent Publication No. 2003/0104062 application Ser. No. 10/213,823), incorporated herein by reference in its entirety.

In certain embodiments, the pharmaceutical formulations provided herein contain COMPOUND 1 and/or azacitidine and, optionally, one or more excipients to form a "drug core." Optional excipients include, e.g., diluents (bulking agents), lubricants, disintegrants, fillers, stabilizers, surfactants, preservatives, coloring agents, flavoring agents, binding agents, excipient supports, glidants, permeation enhancement excipients, plasticizers and the like, e.g., as known in the art. It will be understood by those in the art that some substances serve more than one purpose in a pharmaceutical composition. For instance, some substances are binders that help hold a tablet together after compression, yet are also disintegrants that help break the tablet apart once it reaches the target delivery site. Selection of excipients and amounts to use may be readily determined by the formulation scientist based upon experience and consideration of standard procedures and reference works available in the art.

In certain embodiments, formulations provided herein comprise one or more binders. Binders may be used, e.g., to impart cohesive qualities to a tablet, and thus ensure that the tablet remains intact after compression. Suitable binders include, but are not limited to, starch (including corn starch and pregelatinized starch), gelatin, sugars (including sucrose, glucose, dextrose and lactose), polyethylene glycol, propylene glycol, waxes, and natural and synthetic gums, e.g., acacia sodium alginate, polyvinylpyrrolidone, cellulosic polymers (including hydroxypropyl cellulose, hydroxypropylmethylcellulose, methyl cellulose, ethyl cellulose, hydroxyethyl cellulose, carboxymethyl cellulose and the like), veegum, carbomer (e.g., carbopol), sodium, dextrin, guar gum, hydrogenated vegetable oil, magnesium aluminum silicate, maltodextrin, polymethacrylates, povidone (e.g., KOLLIDON, PLASDONE), microcrystalline cellulose, among others. Binding agents also include, e.g., acacia, agar, alginic acid, cabomers, carrageenan, cellulose acetate phthalate, ceratonia, chitosan, confectioner's sugar, copovidone, dextrates, dextrin, dextrose, ethylcellulose, gelatin, glyceryl behenate, guar gum, hydroxyethyl cellulose, hydroxyethylmethyl cellulose, hydroxypropyl cellulose, hydroxypropyl starch, hypromellose, inulin, lactose, magnesium aluminum silicate, maltodextrin, maltose, methylcellulose, poloxamer, polycarbophil, polydextrose, polyethylene oxide, polymethylacrylates, povidone, sodium alginate, sodium carboxymethylcellulose, starch, pregelatinized starch, stearic acid, sucrose, and zein. The binding agent can be, relative to the drug core, in the amount of about 2% w/w of the drug core; about 4% w/w of the drug core, about 6% w/w of the drug core, about 8% w/w of the drug core, about 10% w/w of the drug core, about 12% w/w of the drug core, about 14% w/w of the drug core, about 16% w/w of the drug core, about 18% w/w of the drug core, about 20% w/w of the drug core, about 22% w/w of the drug core, about 24% w/w of the drug core, about 26% w/w of the drug core, about 28% w/w of the drug core, about 30% w/w of the drug core, about 32% w/w of the drug core, about 34% w/w of the drug core, about 36% w/w of the drug core, about 38% w/w of the drug core, about 40% w/w of the drug core, about 42% w/w of the drug core, about 44% w/w of the drug core, about 46% w/w of the drug core, about 48% w/w of the drug core, about 50% w/w of the drug core, about 52% w/w of the drug core, about 54% w/w of the drug core, about 56% w/w of the drug core, about 58% w/w of the drug core, about 60% w/w of the drug core, about 62% w/w of the drug core, about 64% w/w of the drug core, about 66% w/w of the drug core; about 68% w/w of the drug core, about 70% w/w of the drug core, about 72% w/w of the drug core, about 74% w/w of the drug core, about 76% w/w of the drug core, about 78% w/w of the drug core, about 80% w/w of the drug core, about 82% w/w of the drug core, about 84% w/w of the drug core, about 86% w/w of the drug core, about 88% w/w of the drug core, about 90% w/w of the drug core, about 92% w/w of the drug core, about 94% w/w of the drug core, about 96% w/w of the drug core, about 98% w/w of the drug core, or more, if determined to be appropriate. In certain embodiments, a suitable amount of a particular binder is determined by one of ordinary skill in the art.

In certain embodiments, formulations provided herein comprise one or more diluents. Diluents may be used, e.g., to increase bulk so that a practical size tablet is ultimately provided. Suitable diluents include dicalcium phosphate, calcium sulfate, lactose, cellulose, kaolin, mannitol, sodium chloride, dry starch, microcrystalline cellulose (e.g., AVICEL), microfine cellulose, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT), potassium chloride, sodium chloride, sorbitol and talc, among others. Diluents also include, e.g., ammonium alginate, calcium carbonate, calcium phosphate, calcium sulfate, cellulose acetate, compressible sugar, confectioner's sugar, dextrates, dextrin, dextrose, erythritol, ethylcellulose, fructose, fumaric acid, glyceryl palmitostearate, isomalt, kaolin, lacitol, lactose, mannitol, magnesium carbonate, magnesium oxide, maltodextrin, maltose, medium-chain triglycerides, microcrystalline cellulose, microcrystalline silicified cellulose, powered cellulose, polydextrose, polymethylacrylates, simethicone, sodium alginate, sodium chloride, sorbitol, starch, pregelatinized starch, sucrose, sulfobutylether-β-cyclodextrin, talc, tragacanth, trehalose, and xylitol. Diluents may be used in amounts calculated to obtain a desired volume for a tablet or capsule; in certain embodiments, a diluent is used in an amount of about 5% or more, about 10% or more, about 15% or more, about 20% or more, about 22% or more, about 24% or more, about 26% or more, about 28% or more, about 30% or more, about 32% or more, about 34% or more, about 36% or more, about 38% or more, about 40% or more, about 42% or more, about 44% or more, about 46% or more, about 48% or more, about 50% or more, about 52% or more, about 54% or more, about 56% or more, about 58% or more, about 60% or more, about 62% or more, about 64% or more, about 68% or more, about 70% ore more, about 72% or more, about 74% or more, about 76% or more, about 78% or more, about 80% or more, about 85% or more, about 90% or more, or about 95% or more, weight/weight, of a drug core; between about 10% and about 90% w/w of the drug core; between about 20% and about 80% w/w of the drug core; between about 30% and about 70% w/w of the drug core; between about 40% and about 60% w/w of the drug core. In certain embodiments, a suitable amount of a particular diluent is determined by one of ordinary skill in the art.

In certain embodiments, formulations provided herein comprise one or more lubricants. Lubricants may be used, e.g., to facilitate tablet manufacture; examples of suitable lubricants include, for example, vegetable oils such as peanut oil, cottonseed oil, sesame oil, olive oil, corn oil, and oil of theobroma, glycerin, magnesium stearate, calcium stearate, and stearic acid. In certain embodiments, stearates, if present, represent no more than approximately 2 weight % of the drug-containing core. Further examples of lubricants include, e.g., calcium stearate, glycerin monostearate, glyceryl behenate, glyceryl palmitostearate, magnesium lauryl sulfate, magnesium stearate, myristic acid, palmitic acid, poloxamer, polyethylene glycol, potassium benzoate, sodium benzoate, sodium chloride, sodium lauryl sulfate, sodium stearyl fumarate, stearic acid, talc, and zinc stearate. In particular embodiments, the lubricant is magnesium stearate. In certain embodiments, the lubricant is present, relative to the drug core, in an amount of about 0.2% w/w of the drug core, about 0.4% w/w of the drug core, about 0.6% w/w of the drug core, about 0.8% w/w of the drug core, about 1.0% w/w of the drug core, about 1.2% w/w of the drug core, about 1.4% w/w of the drug core, about 1.6% w/w of the drug core, about 1.8% w/w of the drug core, about 2.0% w/w of the drug core, about 2.2% w/w of the drug core, about 2.4% w/w of the drug core, about 2.6% w/w of the drug core, about 2.8% w/w of the drug core, about 3.0% w/w of the drug core, about 3.5% w/w of the drug core, about 4% w/w of the drug core, about 4.5% w/w of the drug core, about 5% w/w of the drug core, about 6% w/w of the drug core, about 7% w/w of the drug core, about 8% w/w of the drug core, about 10% w/w of the drug core, about 12% w/w of the drug core, about 14% w/w of the drug core, about 16% w/w of the drug core, about 18% w/w of the drug core, about 20% w/w of the drug core, about 25% w/w of the drug core, about 30% w/w of the drug core, about 35% w/w of the drug core, about 40% w/w of the drug core, between about 0.2% and about 10% w/w of the drug core, between about 0.5% and about 5% w/w of the drug core, or between about 1% and about 3% w/w of the drug core. In certain embodiments, a suitable amount of a particular lubricant is determined by one of ordinary skill in the art.

In certain embodiments, formulations provided herein comprise one or more disintegrants. Disintegrants may be used, e.g., to facilitate disintegration of the tablet, and may be, e.g., starches, clays, celluloses, algins, gums or crosslinked polymers. Disintegrants also include, e.g., alginic acid, carboxymethylcellulose calcium, carboxymethylcellulose sodium (e.g., AC-DI-SOL, PRIMELLOSE), colloidal silicon dioxide, croscarmellose sodium, crospovidone (e.g., KOLLIDON, POLYPLASDONE), guar gum, magnesium aluminum silicate, methyl cellulose, microcrystalline cellulose, polacrilin potassium, powdered cellulose, pregelatinized starch, sodium alginate, sodium starch glycolate (e.g., EXPLOTAB) and starch. Additional disintegrants include, e.g., calcium alginate, chitosan, sodium docusate, hydroxypropyl cellulose, and povidone. In certain embodiments, the disintegrant is, relative to the drug core, present in the amount of about 1% w/w of the drug core, about 2% w/w of the drug core, about 3% w/w of the drug core, about 4% w/w of the drug core, about 5% w/w of the drug core, about 6% w/w of the drug core, about 7% w/w of the drug core, about 8% w/w of the drug core, about 9% w/w of the drug core, about 10% w/w of the drug core, about 12% w/w of the drug core, about 14% w/w of the drug core, about 16% w/w of the drug core, about 18% w/w of the drug core, about 20% w/w of the drug core, about 22% w/w of the drug core, about 24% w/w of the drug core, about 26% w/w of the drug core, about 28% w/w of the drug core, about 30% w/w of the drug core, about 32% w/w of the drug core, greater than about 32% w/w of the drug core, between about 1% and about 10% w/w of the drug core, between about 2% and about 8% w/w of the drug core, between about 3% and about 7% w/w of the drug core, or between about 4% and about 6% w/w of the drug core. In certain embodiments, a suitable amount of a particular disintegrant is determined by one of ordinary skill in the art.

In certain embodiments, formulations provided herein comprise one or more stabilizers. Stabilizers (also called absorption enhancers) may be used, e.g., to inhibit or retard drug decomposition reactions that include, by way of example, oxidative reactions. Stabilizing agents include, e.g., d-Alpha-tocopheryl polyethylene glycol 1000 succinate (Vitamin E TPGS), acacia, albumin, alginic acid, aluminum stearate, ammonium alginate, ascorbic acid, ascorbyl palmitate, bentonite, butylated hydroxytoluene, calcium alginate, calcium stearate, calcium carboxymethylcellulose, carrageenan, ceratonia, colloidal silicon dioxide, cyclodextrins, diethanolamine, edetates, ethylcellulose, ethyleneglycol palmitostearate, glycerin monostearate, guar gum, hydroxypropyl cellulose, hypromellose, invert sugar, lecithin, magnesium aluminum silicate, monoethanolamine, pectin, poloxamer, polyvinyl alcohol, potassium alginate, potassium polacrilin, povidone, propyl gallate, propylene glycol, propylene glycol alginate, raffinose, sodium acetate, sodium alginate, sodium borate, sodium carboxymethyl cellulose, sodium stearyl fumarate, sorbitol, stearyl alcohol, sufobutyl-b-cyclodextrin, trehalose, white wax, xanthan gum, xylitol, yellow wax, and zinc acetate. In certain embodiments, the stabilizer is, relative to the drug core, present in the amount of about 1% w/w of the drug core, about 2% w/w of the drug core, about 3% w/w of the drug core, about 4% w/w of the drug core, about 5% w/w of the drug core, about 6% w/w of the drug core, about 7% w/w of the drug core, about 8% w/w of the drug core, about 9% w/w of the drug core, about 10% w/w of the drug core, about 12% w/w of the drug core, about 14% w/w of the drug core, about 16% w/w of the drug core, about 18% w/w of the drug core, about 20% w/w of the drug core, about 22% w/w of the drug core, about 24% w/w of the drug core, about 26% w/w of the drug core, about 28% w/w of the drug core, about 30% w/w of the drug core, about 32% w/w of the drug core, between about 1% and about 10% w/w of the drug core, between about 2% and about 8% w/w of the drug core, between about 3% and about 7% w/w of the drug core, or between about 4% and about 6% w/w of the drug core. In certain embodiments, a suitable amount of a particular stabilizer is determined by one of ordinary skill in the art.

In certain embodiments, formulations provided herein comprise one or more glidants. Glidants may be used, e.g., to improve the flow properties of a powder composition or granulate or to improve the accuracy of dosing. Excipients that may function as glidants include, e.g., colloidal silicon dioxide, magnesium trisilicate, powdered cellulose, starch, tribasic calcium phosphate, calcium silicate, powdered cellulose, colloidal silicon dioxide, magnesium silicate, magnesium trisilicate, silicon dioxide, starch, tribasic calcium phosphate, and talc. In certain embodiments, the glidant is, relative to the drug core, present in the amount of less than about 1% w/w of the drug core, about 1% w/w of the drug core, about 2% w/w of the drug core, about 3% w/w of the drug core, about 4% w/w of the drug core, about 5% w/w of the drug core, about 6% w/w of the drug core, about 7% w/w of the drug core, about 8% w/w of the drug core, about 9% w/w of the drug core, about 10% w/w of the drug core, about 12% w/w of the drug core, about 14% w/w of the drug core, about 16% w/w of the drug core, about 18% w/w of the drug core, about 20% w/w of the drug core, about 22% w/w of the drug core, about 24% w/w of the drug core, about 26% w/w of the drug core, about 28% w/w of the drug core, about 30% w/w of the drug core, about 32% w/w of the drug core, between about 1% and about 10% w/w of the drug core, between about 2% and about 8% w/w of the drug core, between about 3% and about 7% w/w of the drug core, or between about 4% and about 6% w/w of the drug core. In certain embodiments, a suitable amount of a particular glidant is determined by one of ordinary skill in the art.

In certain embodiments, formulations provided herein comprise one or more permeation enhancers (also called, e.g., permeability enhancers). In certain embodiments, the permeation enhancer enhances the uptake of azacitidine through the gastrointestinal wall (e.g., the stomach). In certain embodiments, the permeation enhancer alters the rate and/or amount of azacitidine that enters the bloodstream. In particular embodiments, d-alpha-tocopheryl polyethylene glycol-1000 succinate (Vitamin E TPGS) is used as a permeation enhancer. In particular embodiments, one or more other suitable permeation enhancers are used, including, e.g., any permeation enhancer known in the art.

In one embodiment, the pharmaceutical compositions provided herein may be administered orally, parenterally, by inhalation spray, topically, rectally, nasally, buccally, vaginally or via an implanted reservoir, preferably by oral administration or administration by injection. In one embodiment, the pharmaceutical compositions may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

In one embodiment, the pharmaceutical compositions provided herein may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

In one embodiment, the pharmaceutical compositions provided herein may also be administered in the form of suppositories for rectal administration. These compositions can be prepared by mixing a compound of one aspect of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions provided herein is useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of one aspect of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions provided herein may also be topically applied to the lower intestinal tract by rectal suppository formulation or in a suitable enema formulation. Topically-transdermal patches are also included herein.

In one embodiment, the pharmaceutical compositions provided herein may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions provided herein comprise a combination of COMPOUND 1 and azacitidine, both the COMPOUND 1 and azacitidine should be present at dosage levels of between about 1 to 100%, and more preferably between about 5 to 95% of the dosage normally administered in a monotherapy regimen. Azacitidine may be administered separately, as part of a multiple dose regimen, from the compounds of one aspect of this invention. Alternatively, azacitidine may be part of a single dosage form, mixed together with COMPOUND 1 in a single composition.

In one embodiment, the compositions provided herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. In one embodiment, the pharmaceutical compositions are administered from about 1 to about 6 times per day or alternatively, as a continuous infusion. Such administration can be used as a chronic or acute therapy. The amount of active ingredient that may be combined with the carrier materials to produce a single dosage form varies depending upon the host treated and the particular mode of administration. A typical preparation contains from about 5% to about 95% active compound (w/w). Alternatively, such preparations contain from about 20% to about 80% active compound.

Lower or higher doses than those recited above may be required. Specific dosage and treatment regimens for any particular subject depends upon a variety of factors, including the activity of the specific compound employed, the age, body weight, general health status, sex, diet, time of administration, rate of excretion, drug combination, the severity and course of the disease, condition or symptoms, the subject's disposition to the disease, condition or symptoms, and the judgment of the treating physician.

Upon improvement of a subject's condition, a maintenance dose of a compound, composition or combination provided herein may be administered, if necessary. Subsequently, the dosage or frequency of administration, or both, may be reduced, as a function of the symptoms, to a level at which the improved condition is retained when the symptoms have been alleviated to the desired level. Subjects may, however, require intermittent treatment on a long-term basis upon any recurrence of disease symptoms.

Methods of Use

In one embodiment, provided herein is a method of treating hematological malignancies by administering to a subject a combination of a mutant IDH2 inhibitor and a DNA demethylating agent. In some such embodiments, the hematological malignancy is an advanced hematological malignancy.

In some embodiments, the hematological malignancy to be treated is AML. In some embodiments, the hematological malignancy to be treated is newly diagnosed AML.

In one embodiment, provided herein are methods for treating relapsed or refractory AML by administering to a subject a combination of a mutant IDH2 inhibitor and a DNA demethylating agent. In one embodiment, provided herein are methods for treating relapsed AML by administering to a subject a combination of a mutant IDH2 inhibitor and a DNA demethylating agent. In one embodiment, provided herein are methods for treating refractory AML by administering to a subject a combination of a mutant IDH2 inhibitor and a DNA demethylating agent.

In some embodiments, the hematological malignancy to be treated is MDS. In one embodiment, MDS is selected from the following disorders: refractory anemia (RA); RA with ringed sideroblasts (RARS); RA with excess of blasts (RAEB); refractory cytopenia with multilineage dysplasia (RCMD), refractory cytopenia with unilineage dysplasia (RCUD); unclassifiable myelodysplastic syndrome (MDS-U), myelodysplastic syndrome associated with an isolated del(5q) chromosome abnormality, therapy-related myeloid neoplasms and chronic myelomonocytic leukemia (CMML).

In one embodiment, provided herein are methods for treating MDS by administering to a subject a combination of a mutant IDH2 inhibitor and a DNA demethylating agent.

In one embodiment, the hematological malignancy is refractory anemia (RA).

In one embodiment, the hematological malignancy is RA with ringed sideroblasts (RARS).

In one embodiment, the hematological malignancy is RA with excess of blasts (RAEB).

In one embodiment, the hematological malignancy is refractory cytopenia with multilineage dysplasia (RCMD).

In one embodiment, the hematological malignancy is refractory cytopenia with unilineage dysplasia (RCUD).

In one embodiment, the hematological malignancy is unclassifiable myelodysplastic syndrome (MDS-U).

In one embodiment, the hematological malignancy is myelodysplastic syndrome associated with an isolated del (5q) chromosome abnormality.

In one embodiment, the hematological malignancy is therapy-related myeloid neoplasms.

In one embodiment, the hematological malignancy is chronic myelomonocytic leukemia (CMML).

In one embodiment, MDS is selected from lower-risk MDS and higher-risk MDS.

In certain embodiment, the lower-risk MDS and higher-risk MDS, are determined by prognostic systems that are based most commonly on blast percentage, cytogenetic risk groups, and cytopenias, but which may also include age, performance status, transfusion needs, and other clinical (and increasingly molecular) factors.

In certain embodiments, patients with higher-risk MDS fall into International Prognostic Scoring System (IPSS) categories of Intermediate-2 and High groups, corresponding largely to IPSS-R groups Very High, High, and, sometimes, Intermediate, and which often correspond to World Health Organization (WHO) histologic subtypes of refractory anemia with excess blasts (RAEB)-1 and RAEB-2, with an expected median overall survival of <2 years. Patients with high risk MDS (INT-2/High IPSS or High/Very high IPSS-R scores) have a 33% to 45% chance, respectively, of progression to AML and a median survival of around 12 months without intervention (Greenberg et al. Clinical application and proposal for modification of the International Working Group (IWG) response criteria in myelodysplasia. *Blood* 2006; 108(2):419-25 1997).

In some embodiments, the hematological malignancy to be treated is high risk MDS.

In one embodiment, provided herein is a method of treating solid tumors by administering to a subject a combination of a mutant IDH2 inhibitor and a DNA demethylating agent.

In one embodiment, the mutant IDH2 inhibitor is COMPOUND 1. In one embodiment, COMPOUND 1 encompasses a pharmaceutically acceptable salt, solvate, tautomer, stereoisomer, isotopologue, prodrug, metabolite, or a polymorph thereof.

In one embodiment, the DNA demethylating agent is azacitidine.

In one embodiment, provided herein is a method of treating advanced hematologic malignancies, such as acute myelogenous leukemia (AML), myelodysplastic syndrome (MDS), chronic myelomonocytic leukemia (CMML), myeloid sarcoma, multiple myeloma, lymphoma (e.g., T-cell lymphoma or B-cell lymphoma), angioimmunoblastic T-cell lymphoma (AITL) or blastic plasmacytoid dendritic cell neoplasm, each characterized by the presence of a mutant allele of IDH2, comprising administering to a subject a therapeutically effective amount of COMPOUND 1 and azacitidine.

In one embodiment, provided herein is a method of treating AML characterized by the presence of a mutant allele of IDH2, comprising administering to a subject a therapeutically effective amount of COMPOUND 1 and azacitidine.

In one embodiment, provided herein is a method of treating newly diagnosed AML characterized by the presence of a mutant allele of IDH2, comprising administering to a subject a therapeutically effective amount of COMPOUND 1 and azacitidine.

In one embodiment, provided herein is a method of treating relapsed or refractory AML characterized by the presence of a mutant allele of IDH2, comprising administering to a subject a therapeutically effective amount of COMPOUND 1 and azacitidine.

In one embodiment, provided herein is a method of treating MDS characterized by the presence of a mutant allele of IDH2, comprising administering to a subject a therapeutically effective amount of COMPOUND 1 and azacitidine.

In one embodiment, provided herein is a method of treating high risk MDS characterized by the presence of a mutant allele of IDH2, comprising administering to a subject a therapeutically effective amount of COMPOUND 1 and azacitidine.

In one embodiment, provided herein is a methods of treating advanced hematologic malignancies, such as acute myelogenous leukemia (AML), myelodysplastic syndrome (MDS), chronic myelomonocytic leukemia (CMML), myeloid sarcoma, multiple myeloma, lymphoma (e.g., T-cell lymphoma or B-cell lymphoma), angioimmunoblastic T-cell lymphoma (AITL) or blastic plasmacytoid dendritic cell neoplasm, each characterized by the presence of a mutant allele of IDH2, comprising administering to a subject a therapeutically effective amount of a single crystalline form of COMPOUND 1 and azacitidine. In one embodiment, the single crystalline form of COMPOUND 1 is any percentage between 90% and 100% pure.

In one embodiment, provided herein is a method of treating AML characterized by the presence of a mutant allele of IDH2, comprising administering to a subject a therapeutically effective amount of a single crystalline form of COMPOUND 1 and azacitidine.

In one embodiment, provided herein is a method of treating newly diagnosed AML characterized by the presence of a mutant allele of IDH2, comprising administering to a subject a therapeutically effective amount of a single crystalline form of COMPOUND 1 and azacitidine.

In one embodiment, provided herein is a method of treating relapsed or refractory AML characterized by the presence of a mutant allele of IDH2, comprising administering to a subject a therapeutically effective amount of a single crystalline form of COMPOUND 1 and azacitidine.

In one embodiment, provided herein is a method of treating MDS characterized by the presence of a mutant allele of IDH2, comprising administering to a subject a therapeutically effective amount of a single crystalline form of COMPOUND 1and azacitidine.

In one embodiment, provided herein is a method of treating high risk MDS characterized by the presence of a mutant allele of IDH2, comprising administering to a subject a therapeutically effective amount of a single crystalline form of COMPOUND 1 and azacitidine.

In one embodiment, provided herein is a method of treating advanced hematologic malignancies, such as acute myelogenous leukemia (AML), myelodysplastic syndrome (MDS), chronic myelomonocytic leukemia (CMML), myeloid sarcoma, multiple myeloma, lymphoma (e.g., T-cell lymphoma or B-cell lymphoma), angioimmunoblastic T-cell lymphoma (AITL) or blastic plasmacytoid dendritic cell neoplasm, each characterized by the presence of a mutant allele of IDH2, comprising administering to a subject a pharmaceutical composition comprising a therapeutically effective amount of COMPOUND 1 and azacitidine.

In one embodiment, provided herein is a method of treating AML characterized by the presence of a mutant allele of IDH2, comprising administering to a subject a pharmaceutical composition comprising a therapeutically effective amount of COMPOUND 1 and azacitidine.

In one embodiment, provided herein is a method of treating newly diagnosed AML characterized by the presence of a mutant allele of IDH2, comprising administering to a subject a pharmaceutical composition comprising a therapeutically effective amount of COMPOUND 1 and azacitidine.

In one embodiment, provided herein is a method of treating relapsed or refractory AML characterized by the presence of a mutant allele of IDH2, comprising administering to a subject a pharmaceutical composition comprising a therapeutically effective amount of COMPOUND 1 and azacitidine.

In one embodiment, provided herein is a method of treating MDS characterized by the presence of a mutant allele of IDH2, comprising administering to a subject a pharmaceutical composition comprising a therapeutically effective amount of COMPOUND 1 and azacitidine.

In one embodiment, provided herein is a method of treating high risk MDS characterized by the presence of a mutant allele of IDH2, comprising administering to a subject a pharmaceutical composition comprising a therapeutically effective amount of COMPOUND 1 and azacitidine.

In one embodiment, provided herein is a method of treating an advanced hematologic malignancy, such as acute myelogenous leukemia (AML), myelodysplastic syndrome (MDS), chronic myelomonocytic leukemia (CMML), myeloid sarcoma, multiple myeloma, lymphoma (e.g., T-cell lymphoma or B-cell lymphoma), angioimmunoblastic T-cell lymphoma (AITL) or blastic plasmacytoid dendritic cell neoplasm, each characterized by the presence of a mutant allele of IDH2, comprising administering to a subject a pharmaceutical composition comprising a therapeutically effective amount of a single crystalline form of COMPOUND 1 and azacitidine. In one embodiment, the single crystalline form of COMPOUND 1 is any percentage between 90% and 100% pure.

In one embodiment, provided herein is a method of treating AML characterized by the presence of a mutant allele of IDH2, comprising administering to a subject a pharmaceutical composition comprising a therapeutically effective amount of a single crystalline form of COMPOUND 1 and azacitidine.

In one embodiment, provided herein is a method of treating relapsed or refractory AML characterized by the presence of a mutant allele of IDH2, comprising administering to a subject a pharmaceutical composition comprising a therapeutically effective amount of a single crystalline form of COMPOUND 1 and azacitidine.

In one embodiment, provided herein is a method of treating newly diagnosed AML characterized by the presence of a mutant allele of IDH2, comprising administering to a subject a pharmaceutical composition comprising a therapeutically effective amount of a single crystalline form of COMPOUND 1 and azacitidine.

In one embodiment, provided herein is a method of treating MDS characterized by the presence of a mutant allele of IDH2, comprising administering to a subject a pharmaceutical composition comprising a therapeutically effective amount of a single crystalline form of COMPOUND 1 and azacitidine.

In one embodiment, provided herein is a method of treating high risk MDS characterized by the presence of a mutant allele of IDH2, comprising administering to a subject a pharmaceutical composition comprising a therapeutically effective amount of a single crystalline form of COMPOUND 1 and azacitidine.

In one embodiment, provided herein is a method of treating a solid tumor, such as glioma, melanoma, chondrosarcoma, cholangiocarcinoma, sarcoma, or non-small cell lung cancer, each characterized by the presence of a mutant allele of IDH2, comprising administering to a subject a therapeutically effective amount of COMPOUND 1 and azacitidine.

In one embodiment, provided herein is a methods of treating a solid tumor, such as glioma, melanoma, chondrosarcoma, cholangiocarcinoma, sarcoma, or non-small cell lung cancer, each characterized by the presence of a mutant allele of IDH2, comprising administering to a subject a therapeutically effective amount of a single crystalline form of COMPOUND 1 and azacitidine. In one embodiment, the single crystalline form of COMPOUND 1 is any percentage between 90% and 100% pure.

In one embodiment, provided herein is a method of treating a solid tumor, such as glioma, melanoma, chondrosarcoma, cholangiocarcinoma, sarcoma, or non-small cell lung cancer, each characterized by the presence of a mutant allele of IDH2, comprising administering to a subject a pharmaceutical composition comprising a therapeutically effective amount of COMPOUND 1 and azacitidine.

In one embodiment, provided herein is a method of treating a solid tumor, such as glioma, melanoma, chondrosarcoma, cholangiocarcinoma, sarcoma, or non-small cell lung cancer, each characterized by the presence of a mutant allele of IDH2, comprising administering to a subject a pharmaceutical composition comprising a therapeutically effective amount of a single crystalline form of COMPOUND 1 and azacitidine. In one embodiment, the single crystalline form of COMPOUND 1 is any percentage between 90% and 100% pure.

In one embodiment, the malignancy to be treated is characterized by a mutant allele of IDH2 wherein the IDH2 mutation results in a new ability of the enzyme to catalyze the NADPH-dependent reduction of α-ketoglutarate to R(−)-2-hydroxyglutarate in a subject. In one aspect of this embodiment, the mutant IDH2 has an R140X mutation. In another aspect of this embodiment, the R140X mutation is a R140Q mutation. In another aspect of this embodiment, the R140X mutation is a R140W mutation. In another aspect of this embodiment, the R140X mutation is a R140L mutation. In another aspect of this embodiment, the mutant IDH2 has an R172X mutation. In another aspect of this embodiment, the R172X mutation is a R172K mutation. In another aspect of this embodiment, the R172X mutation is a R172G mutation.

A malignancy can be analyzed by sequencing cell samples to determine the presence and specific nature of (e.g., the changed amino acid present at) a mutation at amino acid 140 and/or 172 of IDH2.

Without being bound by theory, applicants have found that mutant alleles of IDH2, wherein the IDH2 mutation results in a new ability of the enzyme to catalyze the NADPH-dependent reduction of α ketoglutarate to R( ) 2 hydroxyglutarate, and in particular R140Q and/or R172K mutations of IDH2, characterize a subset of all types of cancers, without regard to their cellular nature or location in the body. Thus, the compounds, compositions and methods provided herein are useful to treat any type of cancer that is characterized by the presence of a mutant allele of IDH2 imparting such activity and in particular an IDH2 R140Q and/or R172K mutation.

In one embodiment the malignancy is a tumor wherein at least 30, 40, 50, 60, 70, 80 or 90% of the tumor cells carry an IDH2 mutation, and in particular an IDH2 R140Q, R140W, or R140L and/or R172K or R172G mutation, at the time of diagnosis or treatment.

In one embodiment, the efficacy of treatment of malignancy is monitored by measuring the levels of 2HG in the subject. Typically levels of 2HG are measured prior to treatment, wherein an elevated level is indicated for the use of COMPOUND 1. Once the elevated levels are established, the level of 2HG is determined during the course of and/or following termination of treatment to establish efficacy. In certain embodiments, the level of 2HG is only determined during the course of and/or following termination of treatment. A reduction of 2HG levels during the course of treatment and following treatment is indicative of efficacy. Similarly, a determination that 2HG levels are not elevated during the course of or following treatment is also indicative of efficacy. Typically, 2HG measurements are utilized together with other well-known determinations of efficacy of malignancy treatment, such as reduction in number and size of tumors and/or other cancer-associated lesions, improvement in the general health of the subject, and alterations in other biomarkers that are associated with malignancy treatment efficacy.

2HG can be detected in a sample by LC/MS. The sample is mixed 80:20 with methanol, and centrifuged at 3,000 rpm for 20 minutes at 4 degrees Celsius. The resulting supernatant can be collected and stored at −80 degrees Celsius prior to LC-MS/MS to assess 2-hydroxyglutarate levels. A variety of different liquid chromatography (LC) separation methods can be used. Each method can be coupled by negative electrospray ionization (ESI, −3.0 kV) to triple-quadrupole mass spectrometers operating in multiple reaction monitoring (MRM) mode, with MS parameters optimized on infused metabolite standard solutions. Metabolites can be separated by reversed phase chromatography using 10 mM tributyl-amine as an ion pairing agent in the aqueous mobile phase, according to a variant of a previously reported method (Luo et al. *J Chromatogr A* 1147, 153-64, 2007). One method allows resolution of TCA metabolites: t=0, 50% B; t=5, 95% B; t=7, 95% B; t=8, 0% B, where B refers to an organic mobile phase of 100% methanol. Another method is specific for 2-hydroxyglutarate, running a fast linear gradient from 50%-95% B (buffers as defined above) over 5 minutes. A Synergi Hydro-RP, 100 mm×2 mm, 2.1 m particle size (Phenomonex) can be used as the column, as described above. Metabolites can be quantified by comparison of peak areas with pure metabolite standards at known concentration. Metabolite flux studies from $^{13}$C-glutamine can be performed as described, e.g., in Munger et al. Nat Biotechnol 26, 1179-86, 2008.

In one embodiment 2HG is directly evaluated.

In another embodiment a derivative of 2HG formed in process of performing the analytic method is evaluated. By way of example such a derivative can be a derivative formed in MS analysis. Derivatives can include a salt adduct, e.g., a Na adduct, a hydration variant, or a hydration variant which is also a salt adduct, e.g., a Na adduct, e.g., as formed in MS analysis.

In another embodiment a metabolic derivative of 2HG is evaluated. Examples include species that build up or are elevated, or reduced, as a result of the presence of 2HG, such as glutarate or glutamate that will be correlated to 2HG, e.g., R-2HG.

Exemplary 2HG derivatives include dehydrated derivatives such as the compounds provided below or a salt adduct thereof:

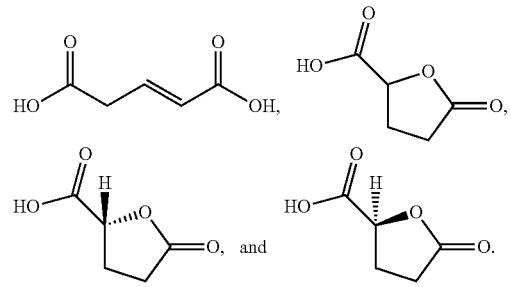

2HG is known to accumulate in the inherited metabolic disorder 2-hydroxyglutaric aciduria. This disease is caused by deficiency in the enzyme 2-hydroxyglutarate dehydrogenase, which converts 2HG to α-KG (Struys, E. A. et al. Am J Hum Genet 76, 358-60 (2005)). Patients with 2-hydroxyglutarate dehydrogenase deficiencies accumulate 2HG in the brain as assessed by MRI and CSF analysis, develop leukoencephalopathy, and have an increased risk of developing brain tumors (Aghili, M., Zahedi, F. & Rafiee, *J Neurooncol* 91, 233-6 (2009); Kolker, S., Mayatepek, E. & Hoffmann, G. F. *Neuropediatrics* 33, 225-31 (2002); Wajner, M., Latini, A., Wyse, A. T. & Dutra-Filho, C. S. *J Inherit Metab Dis* 27, 427-48 (2004)). Furthermore, elevated brain levels of 2HG result in increased ROS levels (Kolker, S. et al. *Eur J Neurosci* 16, 21-8 (2002); Latini, A. et al. *Eur J Neurosci* 17, 2017-22 (2003)), potentially contributing to an increased risk of cancer. The ability of 2HG to act as an NMDA receptor agonist may contribute to this effect (Kolker, S. et al. *Eur J Neurosci* 16, 21-8 (2002)). 2HG may also be toxic to cells by competitively inhibiting glutamate and/or αKG utilizing enzymes. These include transaminases which allow utilization of glutamate nitrogen for amino and nucleic acid biosynthesis, and αKG-dependent prolyl hydroxylases such as those which regulate Hifl-alpha levels.

Thus, according to another embodiment, provided herein is a method of treating 2-hydroxyglutaric aciduria, particularly D-2-hydroxyglutaric aciduria, in a subject by administering to the subject COMPOUND 1 and azacitidine.

Treatment methods described herein can additionally comprise various evaluation steps prior to and/or following treatment with COMPOUND 1 and azacitidine.

In one embodiment, prior to and/or after treatment with COMPOUND 1 and azacitidine, the method further comprises the step of evaluating the growth, size, weight, invasiveness, stage and/or other phenotype of the malignancy.

In one embodiment, prior to and/or after treatment with COMPOUND 1 and azacitidine, the method further comprises the step of evaluating the IDH2 genotype of the malignancy. This may be achieved by ordinary methods in the art, such as DNA sequencing, immuno analysis, and/or evaluation of the presence, distribution or level of 2HG.

In one embodiment, prior to and/or after treatment with COMPOUND 1 and azacitidine, the method further comprises the step of determining the 2HG level in the subject. This may be achieved by spectroscopic analysis, e.g., magnetic resonance-based analysis, e.g., MRI and/or MRS measurement, sample analysis of bodily fluid, such as serum or spinal cord fluid analysis, or by analysis of surgical material, e.g., by mass-spectroscopy.

In one embodiment, COMPOUND 1 and azacitidine are administered concurrently. In one embodiment, COMPOUND 1 and azacitidine are administered sequentially.

In one embodiment, depending on the disease to be treated and the subject's condition, COMPOUND 1 may be administered by oral, parenteral (e.g., intramuscular, intraperitoneal, intravenous, CIV, intracistemal injection or infusion, subcutaneous injection, or implant), inhalation, nasal, vaginal, rectal, sublingual, or topical (e.g., transdermal or local) routes of administration. COMPOUND 1 may be formulated alone or together with one or more active agent (s), in suitable dosage unit with pharmaceutically acceptable excipients, carriers, adjuvants and vehicles, appropriate for each route of administration.

In one embodiment, the amount of COMPOUND 1 administered in the methods provided herein may range, e.g., between about 5 mg/day and about 2,000 mg/day. In one embodiment, the range is between about 10 mg/day and about 2,000 mg/day. In one embodiment, the range is between about 20 mg/day and about 2,000 mg/day. In one embodiment, the range is between about 50 mg/day and about 1,000 mg/day. In one embodiment, the range is between about 100 mg/day and about 1,000 mg/day. In one embodiment, the range is between about 100 mg/day and about 500 mg/day. In one embodiment, the range is between about 150 mg/day and about 500 mg/day. In one embodiment, the range is or between about 150 mg/day and about 250 mg/day. In certain embodiments, particular dosages are, e.g., about 10 mg/day. In one embodiment, the dose is about 20 mg/day. In one embodiment, the dose is about 50 mg/day. In one embodiment, the dose is about 75 mg/day. In one embodiment, the dose is about 100 mg/day. In one embodiment, the dose is about 120 mg/day. In one embodiment, the dose is about 150 mg/day. In one embodiment, the dose is about 200 mg/day. In one embodiment, the dose is about 250 mg/day. In one embodiment, the dose is about 300 mg/day. In one embodiment, the dose is about 350 mg/day. In one embodiment, the dose is about 400 mg/day. In one embodiment, the dose is about 450 mg/day. In one embodiment, the dose is about 500 mg/day. In one embodiment, the dose is about 600 mg/day. In one embodiment, the dose is about 700 mg/day. In one embodiment, the dose is about 800 mg/day. In one embodiment, the dose is about 900 mg/day. In one embodiment, the dose is about 1,000 mg/day. In one embodiment, the dose is about 1,200 mg/day. In one embodiment, the dose is or about 1,500 mg/day. In certain embodiments, particular dosages are, e.g., up to about 10 mg/day. In one embodiment, the particular dose is up to about 20 mg/day. In one embodiment, the particular dose is up to about 50 mg/day. In one embodiment, the particular dose is up to about 75 mg/day. In one embodiment, the particular dose is up to about 100 mg/day. In one embodiment, the particular dose is up to about 120 mg/day. In one embodiment, the particular dose is up to about 150 mg/day. In one embodiment, the particular dose is up to about 200 mg/day. In one embodiment, the particular dose is up to about 250 mg/day. In one embodiment, the particular dose is up to about 300 mg/day. In one embodiment, the particular dose is up to about 350 mg/day. In one embodiment, the particular dose is up to about 400 mg/day. In one embodiment, the particular dose is up to about 450 mg/day. In one embodiment, the particular dose is up to about 500 mg/day. In one embodiment, the particular dose is up to about 600 mg/day. In one embodiment, the particular dose is up to about 700 mg/day. In one embodiment, the particular dose is up to about 800 mg/day. In one embodiment, the particular dose is up to about 900 mg/day. In one embodiment, the particular dose is up to about 1,000 mg/day. In one embodiment, the particular dose is up to about 1,200 mg/day. In one embodiment, the particular dose is up to about 1,500 mg/day.

In one embodiment, the amount of COMPOUND 1 in the pharmaceutical composition or dosage form provided herein may range, e.g., between about 5 mg and about 2,000 mg. In one embodiment, the range is between about 10 mg and about 2,000 mg. In one embodiment, the range is between about 20 mg and about 2,000 mg. In one embodiment, the range is between about 50 mg and about 1,000 mg. In one embodiment, the range is between about 50 mg and about 500 mg. In one embodiment, the range is between about 50 mg and about 250 mg. In one embodiment, the range is between about 100 mg and about 500 mg. In one embodiment, the range is between about 150 mg and about 500 mg. In one embodiment, the range is between about 150 mg and about 250 mg. In certain embodiments, particular amounts are, e.g., about 10 mg. In one embodiment, the particular amount is about 20 mg. In one embodiment, the particular amount is about 50 mg. In one embodiment, the particular amount is about 75 mg. In one embodiment, the particular amount is about 100 mg. In one embodiment, the particular amount is about 120 mg. In one embodiment, the particular amount is about 150 mg. In one embodiment, the particular amount is about 200 mg. In one embodiment, the particular amount is about 250 mg. In one embodiment, the particular amount is about 300 mg. In one embodiment, the particular amount is about 350 mg. In one embodiment, the particular amount is about 400 mg. In one embodiment, the particular amount is about 450 mg. In one embodiment, the particular amount is about 500 mg. In one embodiment, the particular amount is about 600 mg. In one embodiment, the particular amount is about 700 mg. In one embodiment, the particular amount is about 800 mg. In one embodiment, the particular amount is about 900 mg. In one embodiment, the particular amount is about 1,000 mg. In one embodiment, the particular amount is about 1,200 mg. In one embodiment, the particular amount is or about 1,500 mg. In certain embodiments, particular amounts are, e.g., up to about 10 mg. In one embodiment, the particular amount is up to about 20 mg. In one embodiment, the particular amount is up to about 50 mg. In one embodiment, the particular amount is up to about 75 mg. In one embodiment, the particular amount is up to about 100 mg. In one embodiment, the particular amount is up to about 120 mg. In one embodiment, the particular amount is up to about 150 mg. In one embodiment, the particular amount is up to about 200 mg. In one embodiment, the particular amount is up to about 250 mg. In one embodiment, the particular amount is up to about 300 mg. In one embodiment, the particular amount is up to about 350 mg. In one embodiment, the particular amount is up to about 400 mg. In one embodiment, the particular amount is up to about 450 mg. In one embodiment, the particular amount is up to about 500 mg. In one embodiment, the particular amount is up to about 600 mg. In one embodiment, the particular amount is up to about 700 mg. In one embodiment, the particular amount is up to about 800 mg. In one embodiment, the particular amount is up to about 900 mg. In one embodiment, the particular amount is up to about 1,000 mg. In one embodiment, the particular amount is up to about 1,200 mg. In one embodiment, the particular amount is up to about 1,500 mg.

In one embodiment, COMPOUND 1 can be delivered as a single dose such as, e.g., a single bolus injection, or oral tablets or pills; or over time such as, e.g., continuous infusion over time or divided bolus doses over time. In one embodiment, compound 1 can be administered repetitively if necessary, for example, until the patient experiences stable disease or regression, or until the patient experiences disease progression or unacceptable toxicity. Stable disease or lack thereof is determined by methods known in the art such as evaluation of patient's symptoms, physical examination, visualization of the tumor that has been imaged using X-ray, CAT, PET, or MRI scan and other commonly accepted evaluation modalities.

In certain embodiments, COMPOUND 1 is administered to a patient in cycles (e.g., daily administration for one week, then a rest period with no administration for up to three weeks). Cycling therapy involves the administration of an active agent for a period of time, followed by a rest for a period of time, and repeating this sequential administration. Cycling therapy can reduce the development of resistance, avoid or reduce the side effects, and/or improves the efficacy of the treatment.

In one embodiment, a method provided herein comprises administering COMPOUND 1 in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or greater than 40 cycles. In one embodiment, the median number of cycles administered in a group of patients is about 1. In one embodiment, the median number of cycles administered in a group of patients is about 2. In one embodiment, the median number of cycles administered in a group of patients is about 3. In one embodiment, the median number of cycles administered in a group of patients is about 4. In one embodiment, the median number of cycles administered in a group of patients is about 5. In one embodiment, the median number of cycles administered in a group of patients is about 6. In one embodiment, the median number of cycles administered in a group of patients is about 7. In one embodiment, the median number of cycles administered in a group of patients is about 8. In one embodiment, the median number of cycles administered in a group of patients is about 9. In one embodiment, the median number of cycles administered in a group of patients is about 10. In one embodiment, the median number of cycles administered in a group of patients is about 11. In one embodiment, the median number of cycles administered in a group of patients is about 12. In one embodiment, the median number of cycles administered in a group of patients is about 13. In one embodiment, the median number of cycles administered in a group of patients is about 14. In one embodiment, the median number of cycles administered in a group of patients is about 15. In one embodiment, the median number of cycles administered in a group of patients is about 16. In one embodiment, the median number of cycles administered in a group of patients is about 17. In one embodiment, the median number of cycles administered in a group of patients is about 18. In one embodiment, the median number of cycles administered in a group of patients is about 19. In one embodiment, the median number of cycles administered in a group of patients is about 20. In one embodiment, the median number of cycles administered in a group of patients is about 21. In one embodiment, the median number of cycles administered in a group of patients is about 22. In one embodiment, the median number of cycles administered in a group of patients is about 23. In one embodiment, the median number of cycles administered in a group of patients is about 24. In one embodiment, the median number of cycles administered in a group of patients is about 25. In one embodiment, the median number of cycles administered in a group of patients is about 26. In one embodiment, the median number of cycles administered in a group of patients is about 27. In one embodiment, the median number of cycles administered in a group of patients is about 28. In one embodiment, the median number of cycles administered in a group of patients is about 29. In one embodiment, the median number of cycles administered in a group of patients is about 30. In one embodiment, the median number of cycles administered in a group of patients is greater than about 30 cycles.

In certain embodiments, treatment cycles comprise multiple doses of COMPOUND 1 administered to a subject in need thereof over multiple days (e.g., 1, 2, 3, 4, 5, 6, 7, 8, 9, 10, 11, 12, 13, 14, or greater than 14 days), optionally followed by treatment dosing holidays (e.g., 1, 2, 3, 4, 5, 6, 7, 8, 9, 10, 11, 12, 13, 14, 15, 16, 17, 18, 19, 20, 21, 22, 23, 24, 25, 26, 27, 28, or greater than 28 days).

In one embodiment, depending on the disease to be treated and the subject's condition, azacitidine may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. Azacitidine may be formulated, alone or together with COMPOUND 1 and/or one or more active agent(s), in suitable dosage unit with pharmaceutically acceptable excipients, carriers, adjuvants and vehicles, appropriate for each route of administration.

In one embodiment, azacitidine is administered by, e.g., intravenous (IV), subcutaneous (SC) or oral routes. Certain embodiments herein provide co-administration of azacitidine with COMPOUND 1 and/or one or more additional active agents to provide a synergistic therapeutic effect in subjects in need thereof. The co-administered active agent(s) may be cancer therapeutic agents, as described herein. In certain embodiments, the co-administered active agent(s) may be inhibitors of IDH2. In certain embodiments, the co-administered agent(s) may be dosed, e.g., orally or by injection (e.g., IV or SC).

In certain embodiments, treatment cycles comprise multiple doses of azacitidine administered to a subject in need thereof over multiple days (e.g., 1, 2, 3, 4, 5, 6, 7, 8, 9, 10, 11, 12, 13, 14, or greater than 14 days), optionally followed by treatment dosing holidays (e.g., 1, 2, 3, 4, 5, 6, 7, 8, 9, 10, 11, 12, 13, 14, 15, 16, 17, 18, 19, 20, 21, 22, 23, 24, 25, 26, 27, 28, or greater than 28 days). Suitable dosage amounts for the methods provided herein include, e.g., therapeutically effective amounts and prophylactically effective amounts. For example, in certain embodiments, the amount of azacitidine administered in the methods provided herein may range, e.g., between about 50 $mg/m^2/day$ and about 2,000 $mg/m^2/day$. In certain embodiments, the amount of azacitidine is between about 100 $mg/m^2/day$ and about 1,000 $mg/m^2/day$. In certain embodiments, the amount of azacitidine is between about 100 $mg/m^2/day$ and about 500 $mg/m^2/day$. In certain embodiments, the amount of azacitidine is between about 50 $mg/m^2/day$ and about 500 $mg/m^2/day$. In certain embodiments, the amount of azacitidine is between about 50 $mg/m^2/day$ and about 200 $mg/m^2/day$. In certain embodiments, the amount of azacitidine is between about 50 $mg/m^2/day$ and about 100 $mg/m^2/day$. In certain embodiments, the amount of azacitidine is between about 50 $mg/m^2/day$ and about 75 $mg/m^2/day$. In certain embodiments, the amount of azacitidine is between about 120 $mg/m^2/day$ and about 250 $mg/m^2/day$. In certain embodiments, the particular dosage is about 50 mg/m²/day. In one embodiment, the particular dosage is about 60 mg/m²/day. In one embodiment, the particular dosage is about 75 mg/m²/day. In one embodiment, the particular dosage is about 80 mg/m²/day. In one embodiment, the particular dosage is about 100 mg/m²/day. In one embodiment, the particular dosage is about 120 mg/m²/day. In one embodiment, the particular dosage is about 140 mg/m²/day. In one embodiment, the particular dosage is about 150 mg/m²/day. In one embodiment, the particular dosage is about 180 mg/m²/day. In one embodiment, the particular dosage is about 200 mg/m²/day. In one embodiment, the particular dosage is about 220 mg/m²/day. In one embodiment, the particular dosage is about 240 mg/m²/day. In one embodiment, the particular dosage is about 250 mg/m²/day. In one embodiment, the particular dosage is about 260 mg/m²/day. In one embodiment, the particular dosage is about 280 mg/m²/day. In one embodiment, the particular dosage is about 300 mg/m²/day. In one embodiment, the particular dosage is about 320 mg/m²/day. In one embodiment, the particular dosage is about 350 mg/m²/day. In one embodiment, the particular dosage is about 380 mg/m²/day. In one embodiment, the particular dosage is about 400 mg/m²/day. In one embodiment, the particular dosage is about 450 mg/m²/day. In one embodiment, the particular dosage is about 500 mg/m²/day. In certain embodiments, the particular dosage is up to about 100 mg/m²/day. In one embodiment, the particular dosage is up to about 120 mg/m²/day. In one embodiment, the particular dosage is up to about 140 mg/m²/day. In one embodiment, the particular dosage is up to about 150 mg/m²/day. In one embodiment, the particular dosage is up to about 180 mg/m²/day. In one embodiment, the particular dosage is up to about 200 mg/m²/day. In one embodiment, the particular dosage is up to about 220 mg/m²/day. In one embodiment, the particular dosage is up to about 240 mg/m²/day. In one embodiment, the particular dosage is up to about 250 mg/m²/day. In one embodiment, the particular dosage is up to about 260 mg/m²/day. In one embodiment, the particular dosage is up to about 280 mg/m²/day. In one embodiment, the particular dosage is up to about 300 mg/m²/day. In one embodiment, the particular dosage is up to about 320 mg/m²/day. In one embodiment, the particular dosage is up to about 350 mg/m²/day. In one embodiment, the particular dosage is up to about 380 mg/m²/day. In one embodiment, the particular dosage is up to about 400 mg/m²/day. In one embodiment, the particular dosage is up to about 450 mg/m²/day. In one embodiment, the particular dosage is up to about 500 mg/m²/day. In one embodiment, the particular dosage is up to about 750 mg/m²/day. In one embodiment, the particular dosage is up to about 1000 mg/m²/day.

In one embodiment, the amount of azacitidine administered in the methods provided herein may range, e.g., between about 5 mg/day and about 2,000 mg/day. In one embodiment, the range is between about 10 mg/day and about 2,000 mg/day. In one embodiment, the range is between about 20 mg/day and about 2,000 mg/day. In one embodiment, the range is between about 50 mg/day and about 1,000 mg/day. In one embodiment, the range is between about 100 mg/day and about 1,000 mg/day. In one embodiment, the range is between about 100 mg/day and about 500 mg/day. In one embodiment, the range is between about 150 mg/day and about 500 mg/day. In one embodiment, the range is between about 150 mg/day and about 250 mg/day. In certain embodiments, the particular dosage is about 10 mg/day. In one embodiment, the particular dosage is about 20 mg/day. In one embodiment, the particular dosage is about 50 mg/day. In one embodiment, the particular dosage is about 75 mg/day. In one embodiment, the particular dosage is about 100 mg/day. In one embodiment, the particular dosage is about 120 mg/day. In one embodiment, the particular dosage is about 150 mg/day. In one embodiment, the particular dosage is about 200 mg/day. In one embodiment, the particular dosage is about 250 mg/day. In one embodiment, the particular dosage is about 300 mg/day. In one embodiment, the particular dosage is about 350 mg/day. In one embodiment, the particular dosage is about 400 mg/day. In one embodiment, the particular dosage is about 450 mg/day. In one embodiment, the particular dosage is about 500 mg/day. In one embodiment, the particular dosage is about 600 mg/day. In one embodiment, the particular dosage is about 700 mg/day. In one embodiment, the particular dosage is about 800 mg/day. In one embodiment, the particular dosage is about 900 mg/day. In one embodiment, the particular dosage is about 1,000 mg/day. In one embodiment, the particular dosage is about 1,200 mg/day. In one embodiment, the particular dosage is about 1,500 mg/day. In certain embodiments, the particular dosage is up to about 10 mg/day. In one embodiment, the particular dosage is up to about 20 mg/day. In one embodiment, the particular dosage is up to about 50 mg/day. In one embodiment, the particular dosage is up to about 75 mg/day. In one embodiment, the particular dosage is up to about 100 mg/day. In one embodiment, the particular dosage is up to about 120 mg/day. In one embodiment, the particular dosage is up to about 150 mg/day. In one embodiment, the particular dosage is up to about 200 mg/day. In one embodiment, the particular dosage is up to about 250 mg/day. In one embodiment, the particular dosage is up to about 300 mg/day. In one embodiment, the particular dosage is up to about 350 mg/day. In one embodiment, the particular dosage is up to about 400 mg/day. In one embodiment, the particular dosage is up to about 450 mg/day. In one embodiment, the particular dosage is up to about 500 mg/day. In one embodiment, the particular dosage is up to about 600 mg/day. In one embodiment, the particular dosage is up to about 700 mg/day. In one embodiment, the particular dosage is up to about 800 mg/day. In one embodiment, the particular dosage is up to about 900 mg/day. In one embodiment, the particular dosage is up to about 1,000 mg/day. In one embodiment, the particular dosage is up to about 1,200 mg/day. In one embodiment, the particular dosage is up to about 1,500 mg/day.

In one embodiment, the amount of azacitidine in the pharmaceutical composition or dosage form provided herein may range, e.g., between about 5 mg and about 2,000 mg. In one embodiment, the range is between about 10 mg and about 2,000 mg. In one embodiment, the range is between about 20 mg and about 2,000 mg. In one embodiment, the range is between about 50 mg and about 1,000 mg. In one embodiment, the range is between about 50 mg and about 500 mg. In one embodiment, the range is between about 50 mg and about 250 mg. In one embodiment, the range is between about 100 mg and about 500 mg. In one embodiment, the range is between about 150 mg and about 500 mg. In one embodiment, the range is between about 150 mg and about 250 mg. In certain embodiments, the particular amount is about 10 mg. In one embodiment, the particular amount is about 20 mg. In one embodiment, the particular amount is about 50 mg. In one embodiment, the particular amount is about 75 mg. In one embodiment, the particular amount is about 100 mg. In one embodiment, the particular amount is about 120 mg. In one embodiment, the particular amount is about 150 mg. In one embodiment, the particular amount is about 200 mg. In one embodiment, the particular amount is about 250 mg. In one embodiment, the particular amount is about 300 mg. In one embodiment, the particular amount is about 350 mg. In one embodiment, the particular amount is about 400 mg. In one embodiment, the particular amount is about 450 mg. In one embodiment, the particular amount is about 500 mg. In one embodiment, the particular amount is about 600 mg. In one embodiment, the particular amount is about 700 mg. In one embodiment, the particular amount is about 800 mg. In one embodiment, the particular amount is about 900 mg. In one embodiment, the particular amount is about 1,000 mg. In one embodiment, the particular amount is about 1,200 mg. In one embodiment, the particular amount is about 1,500 mg. In certain embodiments, the particular amount is up to about 10 mg. In one embodiment, the particular amount is up to about 20 mg. In one embodiment, the particular amount is up to about 50 mg. In one embodiment, the particular amount is up to about 75 mg. In one embodiment, the particular amount is up to about 100 mg. In one embodiment, the particular amount is up to about 120 mg. In one embodiment, the particular amount is up to about 150 mg. In one embodiment, the particular amount is up to about 200 mg. In one embodiment, the particular amount is up to about 250 mg. In one embodiment, the particular amount is up to about 300 mg. In one embodiment, the particular amount is up to about 350 mg. In one embodiment, the particular amount is up to about 400 mg. In one embodiment, the particular amount is up to about 450 mg. In one embodiment, the particular amount is up to about 500 mg. In one embodiment, the particular amount is up to about 600 mg. In one embodiment, the particular amount is up to about 700 mg. In one embodiment, the particular amount is up to about 800 mg. In one embodiment, the particular amount is up to about 900 mg. In one embodiment, the particular amount is up to about 1,000 mg. In one embodiment, the particular amount is up to about 1,200 mg. In one embodiment, the particular amount is up to about 1,500 mg.

In one embodiment, azacitidine can be delivered as a single dose such as, e.g., a single bolus injection, or oral tablets or pills; or over time such as, e.g., continuous infusion over time or divided bolus doses over time. In one embodiment, azacitidine can be administered repetitively if necessary, for example, until the patient experiences stable disease or regression, or until the patient experiences disease progression or unacceptable toxicity. Stable disease or lack thereof is determined by methods known in the art such as evaluation of patient's symptoms, physical examination, visualization of the tumor that has been imaged using X-ray, CAT, PET, or MRI scan and other commonly accepted evaluation modalities.

In one embodiment, azacitidine can be administered once daily or divided into multiple daily doses such as twice daily, three times daily, and four times daily. In one embodiment, the administration can be continuous (i.e., daily for consecutive days or every day), intermittent, e.g., in cycles (i.e., including days, weeks, or months of rest when no drug is administered). In one embodiment, azacitidine is administered daily, for example, once or more than once each day for a period of time. In one embodiment, azacitidine is administered daily for an uninterrupted period of at least 7 days. In some embodiments, azacitidine is administered up to 52 weeks. In one embodiment, azacitidine is administered intermittently, i.e., stopping and starting at either regular or irregular intervals. In one embodiment, azacitidine is administered for one to six days per week. In one embodiment, azacitidine is administered on alternate days. In one embodiment, azacitidine is administered in cycles (e.g., administered daily or continuously for a certain period interrupted with a rest period). In one embodiment, azacitidine is administered daily for two to eight consecutive weeks, then a rest period with no administration for up to one week; or e.g., daily administration for one week, then a rest period with no administration for up to three weeks).

In one embodiment, the frequency of administration ranges from about daily to about monthly In one embodiment, azacitidine is administered once a day. In another embodiment, azacitidine is administered twice a day. In yet another embodiment, azacitidine is administered three times a day. In still another embodiment, azacitidine is administered four times a day. In one embodiment, azacitidine is administered once every other day. In one embodiment, azacitidine is administered twice a week. In one embodiment, azacitidine is administered once every week. In one embodiment, azacitidine is administered once every two weeks. In one embodiment, azacitidine is administered once every three weeks. In one embodiment, azacitidine is administered once every four weeks.

In one embodiment, azacitidine is administered once per day from one day to six months. In one embodiment, azacitidine is administered from one week to three months. In one embodiment, azacitidine is administered from one week to four weeks. In one embodiment, azacitidine is administered from one week to three weeks. In one embodiment, azacitidine is administered from one week to two weeks. In one embodiment, azacitidine is administered once per day for about one week. In one embodiment, azacitidine is administered once per day for about two weeks. In one embodiment, azacitidine is administered once per day for about three weeks. In one embodiment, azacitidine is administered once per day for about four weeks. In one embodiment, azacitidine is administered once per day for about 6 weeks. In one embodiment, azacitidine is administered once per day for about 9 weeks. In one embodiment, azacitidine is administered once per day for about 12 weeks. In one embodiment, azacitidine is administered once per day for about 15 weeks. In one embodiment, azacitidine is administered once per day for about 18 weeks. In one embodiment, azacitidine is administered once per day for about 21 weeks. In one embodiment, azacitidine is administered once per day for about 26 weeks. In certain embodiments, azacitidine is administered intermittently. In certain embodiments, azacitidine is administered intermittently in the amount of between about 50 mg/m$^2$/day and about 2,000 mg/m$^2$/day. In certain embodiments, azacitidine is administered continuously. In certain embodiments, azacitidine is administered continuously in the amount of between about 50 mg/m$^2$/day and about 1,000 mg/m$^2$/day.

In certain embodiments, azacitidine is administered to a patient in cycles (e.g., daily administration for one week, then a rest period with no administration for up to three weeks). Cycling therapy involves the administration of an active agent for a period of time, followed by a rest for a period of time, and repeating this sequential administration. Cycling therapy can reduce the development of resistance, avoid or reduce the side effects, and/or improves the efficacy of the treatment.

In one embodiment, a method provided herein comprises administering azacitidine in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or greater than 40 cycles. In one embodiment, the median number of cycles administered in a group of patients is about 1. In one embodiment, the median number of cycles is about 2. In one embodiment, the median number of cycles is about 3. In one embodiment, the median number of cycles is about 4. In one embodiment, the median number of cycles is about 5. In one embodiment, the median number of cycles is about 6. In one embodiment, the median number of cycles is about 7. In one embodiment, the median number of cycles is about 8. In one embodiment, the median number of cycles is about 9. In one embodiment, the median number of cycles is about 10. In one embodiment, the median number of cycles is about 11. In one embodiment, the median number of cycles is about 12. In one embodiment, the median number of cycles is about 13. In one embodiment, the median number of cycles is about 14. In one embodiment, the median number of cycles is about 15. In one embodiment, the median number of cycles is about 16. In one embodiment, the median number of cycles is about 17. In one embodiment, the median number of cycles is about 18. In one embodiment, the median number of cycles is about 19. In one embodiment, the median number of cycles is about 20. In one embodiment, the median number of cycles is about 21. In one embodiment, the median number of cycles is about 22. In one embodiment, the median number of cycles is about 23. In one embodiment, the median number of cycles is about 24. In one embodiment, the median number of cycles is about 25. In one embodiment, the median number of cycles is about 26. In one embodiment, the median number of cycles is about 27. In one embodiment, the median number of cycles is about 28. In one embodiment, the median number of cycles is about 29. In one embodiment, the median number of cycles is about 30. In one embodiment, the median number of cycles is greater than about 30 cycles.

In one embodiment, azacitidine is administered to a patient at a dose provided herein over a cycle of 28 days which consists of a 7-day treatment period and a 21-day resting period. In one embodiment, azacitidine is administered to a patient at a dose provided herein each day from day 1 to day 7, followed with a resting period from day 8 to day 28 with no administration of azacitidine. In one embodiment, azacitidine is administered to a patient in cycles, each cycle consisting of a 7-day treatment period followed with a 21-day resting period. In particular embodiments, azacitidine is administered to a patient at a dose of about 50, about 60, about 70, about 75, about 80, about 90, or about 100 mg/m$^2$/day, for 7 days, followed with a resting period of 21 days. In one embodiment, azacitidine is administered intravenously. In one embodiment, azacitidine is administered subcutaneously.

In other embodiments, azacitidine is administered orally in cycles. In one embodiment, azacitidine is administered daily in single or divided doses for about one week. In one embodiment, azacitidine is administered daily for about two weeks. In one embodiment, azacitidine is administered daily for about three weeks. In one embodiment, azacitidine is administered daily for about four weeks. In one embodiment, azacitidine is administered daily for about five weeks. In one embodiment, azacitidine is administered daily for about six weeks. In one embodiment, azacitidine is administered daily for about eight weeks. In one embodiment, azacitidine is administered daily for about ten weeks. In one embodiment, azacitidine is administered daily for about fifteen weeks. In one embodiment, azacitidine is administered daily for or about twenty weeks. The administration is followed by a rest period of about 1 day to about ten weeks. In one embodiment, the methods provided herein contemplate cycling treatments of about one week. In one embodiment, the methods provided herein contemplate cycling treatments of about two weeks. In one embodiment, the methods provided herein contemplate cycling treatments of about three weeks. In one embodiment, the methods provided herein contemplate cycling treatments of about four weeks. In one embodiment, the methods provided herein contemplate cycling treatments of about five weeks. In one embodiment, the methods provided herein contemplate cycling treatments of about six weeks. In one embodiment, the methods provided herein contemplate cycling treatments of about eight weeks. In one embodiment, the methods provided herein contemplate cycling treatments of about ten weeks. In one embodiment, the methods provided herein contemplate cycling treatments of about fifteen weeks. In one embodiment, the methods provided herein contemplate cycling treatments of about twenty weeks. In some embodiments, azacitidine is administered daily in single or divided doses for about one week. In one embodiment, azacitidine is administered daily for about two weeks. In one embodiment, azacitidine is administered daily for about three weeks. In one embodiment, azacitidine is administered daily for about four weeks. In one embodiment, azacitidine is administered daily for about five weeks. In one embodiment, azacitidine is administered daily for about six weeks. In one embodiment, the resting period of about 1, 3, 5, 7, 9, 12, 14, 16, 18, 20, 22, 24, 26, 28, 29, or 30 days. In some embodiments, the rest period is 1 day. In some embodiments, the rest period is 3 days. In some embodiments, the rest period is 7 days. In some embodiments, the rest period is 14 days. In some embodiments, the rest period is 28 days. The frequency, number and length of dosing cycles can be increased or decreased.

In one embodiment, COMPOUND 1 is administered orally once a day. In one embodiment, COMPOUND 1 is administered on days 1-28 of each 28-day cycle. In one embodiment, 50 mg of COMPOUND 1 is administered orally once a day. In another embodiment, 100 mg of COMPOUND 1 is administered orally once a day. In yet another embodiment, 200 mg of COMPOUND 1 is administered orally once a day. In one embodiment, azacitidine is administered subcutaneously for 7 days. In one embodiment, azacitidine is administered on days 1-7 of each 28-day cycle. In one embodiment, 75 mg/m$^2$/day of azacitidine is administered on days 1-7 of each 28-day cycle.

EXAMPLES

Example 1. Effect of Combination of COMPOUND 1 and Azacitidine on EPO-Differentiation in AML Cells Cell Lines Measures of cell differentiation, growth and death were evaluated in an engineered TF-1 erythroleukemia cells overexpressing the IDH2/R140Q allele or the empty vector control TF-1/pLVX (Wang et al., *Science* 340:622-626, 2013). The cells were grown in RPMI containing HEPES and L-glutamine (Lonza 12-115F), 10% FBS (HyClone SH30088.03), Pen/Strep (Life Technologies 15070-063), G418: final concentration 500 µg/ml (Life Technologies 10131-027); GM-CSF: final concentration 5 ng/ml (R&D 215-GM-050). Only newly grown cells were used. G418 and GM-CSF were added fresh to media each time cells were passaged. Media was changed every 2-3 days by pelleting cells and resuspending in fresh media or by adding 2 ml of cells to 10 ml of fresh media. When cells were treated with a compound, the media was changed by pelleting cells to ensure proper concentration of the compound.

Preparation of Compound Solutions

COMPOUND 1 was obtained as 10 mM stock solution in DMSO. The stock was aliquoted as 20 µl batches and stored at −20° C. The running stock was thawed and kept at room temperature in dark for use in ongoing experiments.

Azacitidine was kept in dessicator at 4° C. The required quantity was weighed in a Mettler covered weighing balance and reconstituted in RNase and DNase free water to obtain a 10 mM running stock. The solution was aliquoted as 30 µl batches and stored at −20° C. Fresh stock was prepared every six months. A 10 mM azacitidine vial was thawed for each experiment and discarded after use.

A 100 µl stock for each compound was prepared by adding 10 µl of 10 mM stock in 990 µl of media. From this 100× stock, the required volume was added to cells for a given desired final concentration.

Assays

Erythropoietin (EPO) Differentiation Assay

F1/pLVX and TF1 IDH2/R140Q cells (100,000 cells/ml) were pretreated for 7 days with COMPOUND 1, azacitidine or combination thereof (medium was changed every 2 days) and washed with PBS to remove residual GM-CSF. Cells were induced to differentiate using EPO (2 unit/ml) in the presence or absence of COMPOUND 1. Induction continued for 7 days and the cell pellets were collected and imaged for hemoglobinization content (as a surrogate for differentiation into blood lineage).

HBG and KLF1 qPCR

The RNA was isolated from cells by RNA easy kit (obtained from Qiagen). 500 ng of RNA was used to make cDNA that was subjected to real-time qPCR to detect fetal hemoglobin (HBG) and KLF-1 gene expression. The RNA easy kit was obtained from Qiagen. cDNA was made from Superscript VILO kit (Life technologies). Taqman probes were obtained from Applied Biosciences.

Hematopoietic Stem Cell and Blast Content Determination (CD34, CD38, FACS)

Cells were blocked in 10×BSA and diluted with MACS rinsing solution to 1× concentration for 15 min (staining buffer, BD Biosciences). Supernatant was removed by spinning. 10 µl of anti-CD34 FITC and anti-CD38 APC antibodies (each in staining buffer) were added. Mouse IgG2a FITC and IgG2a APC were used as isotype controls. Cells were stained for 10 min in dark, the solution was spinned to remove supernatant, the cells were resuspended in 300 µl of staining buffer and proceed to fluorescence-activated cell sorting (FACS).

Results

Enhanced EPO-Induced Differentiation

Measures of cell differentiation, growth and death were evaluated in TF1-R140Q cells, using an in vitro EPO differentiation assay and dose-schedule paradigms represented in FIG. 1. Cells were treated with vehicle, azacitidine alone, COMPOUND 1 alone, or the combination of azacitidine and COMPOUND 1. In the sequential schedule, cells were pre-treated with azacitidine for three days before adding COMPOUND 1. In the concurrent schedule, cells were co-treated with azacitidine and COMPOUND 1 throughout the assay.

Both schedules demonstrated similar trends on differentiation endpoints of hemoglobinization, KLF1 (Kruppel-like factor 1) and HBG (hemoglobin gene A/B) RNA levels (FIG. 2). With the sequential schedule, COMPOUND 1 alone increased hemoglobin production in a dose-dependent manner, as evidenced by increased red color of cell pellets with 0.2 M and 1.0 M concentrations. Azacitidine alone had little or no effect on cell pellet color; however, with the combination of azacitidine and COMPOUND 1, the coloration/hemoglobinization was noticeably greater than with COMPOUND 1 alone (FIG. 2Ai).

Figure 2A:
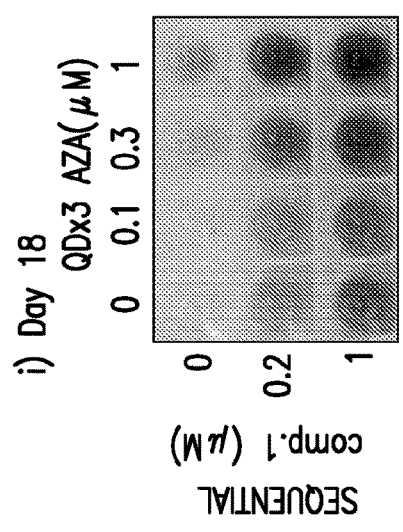
FIG. 2A depicts the effect of the combination of azacitidine and COMPOUND 1 used sequentially on differentiation markers. The pellets were observed for hemoglobinization on day 18 (i). Treated cells were subjected to qRT-PCR (ii) and to HBG qRT-PCR (iii).
Figure 2A:
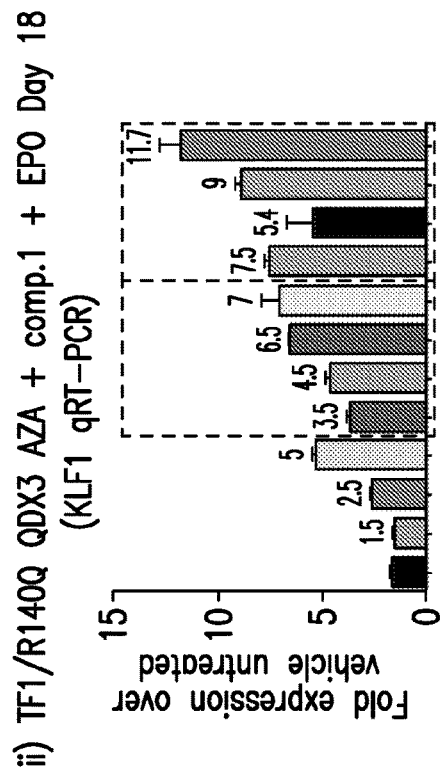
Figure 2A:
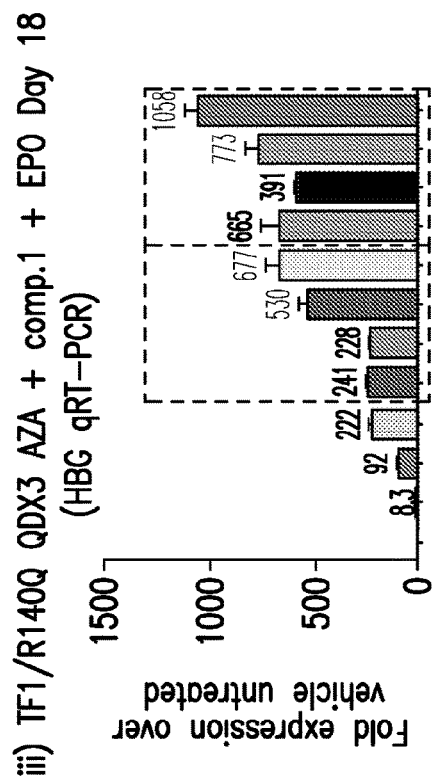
Figure 7:
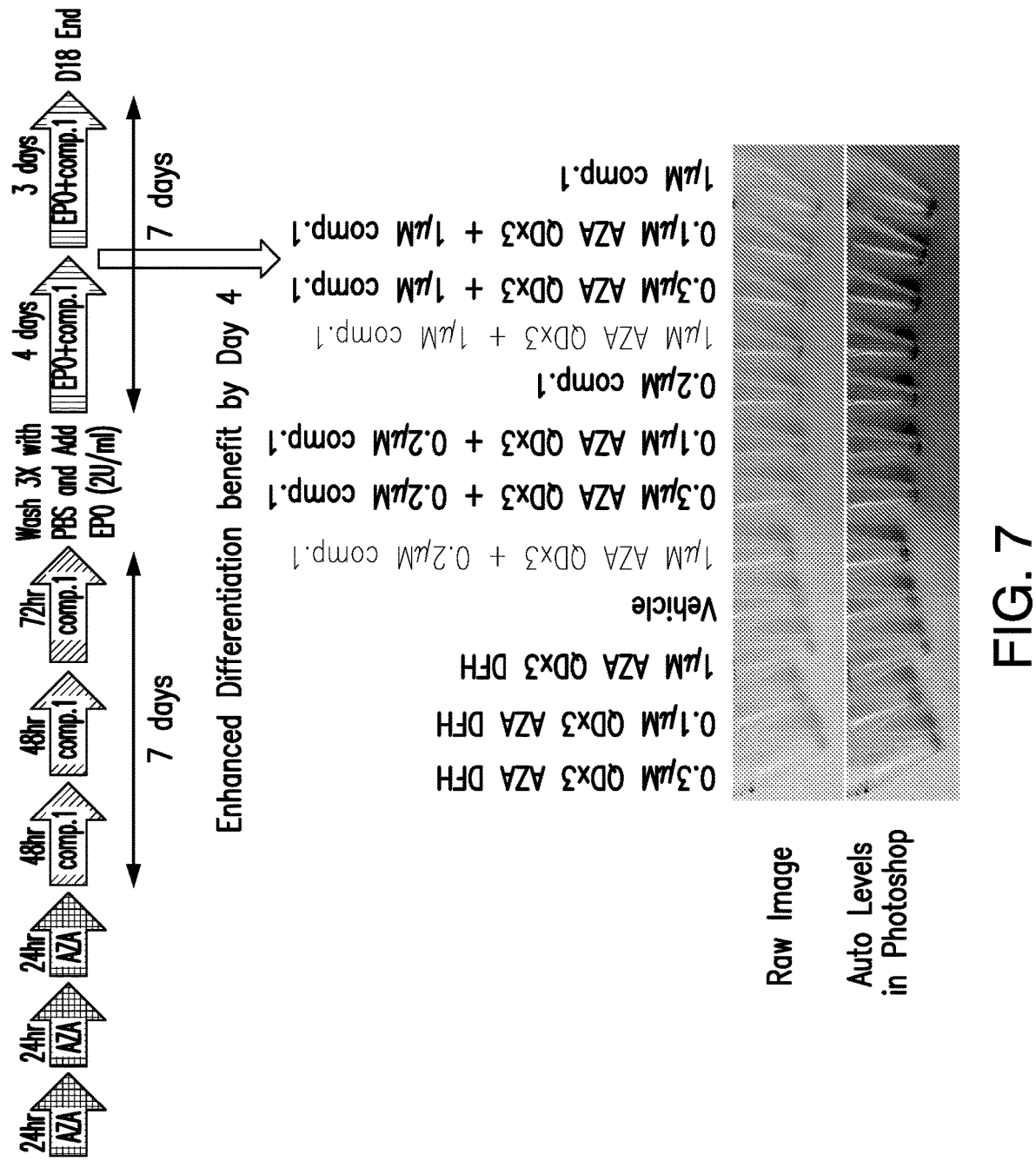
FIG. 7 depicts the effect of the combination of azacitidine and COMPOUND 1 used sequentially on early (day 4) enhanced differentiation.
Figure 8A:
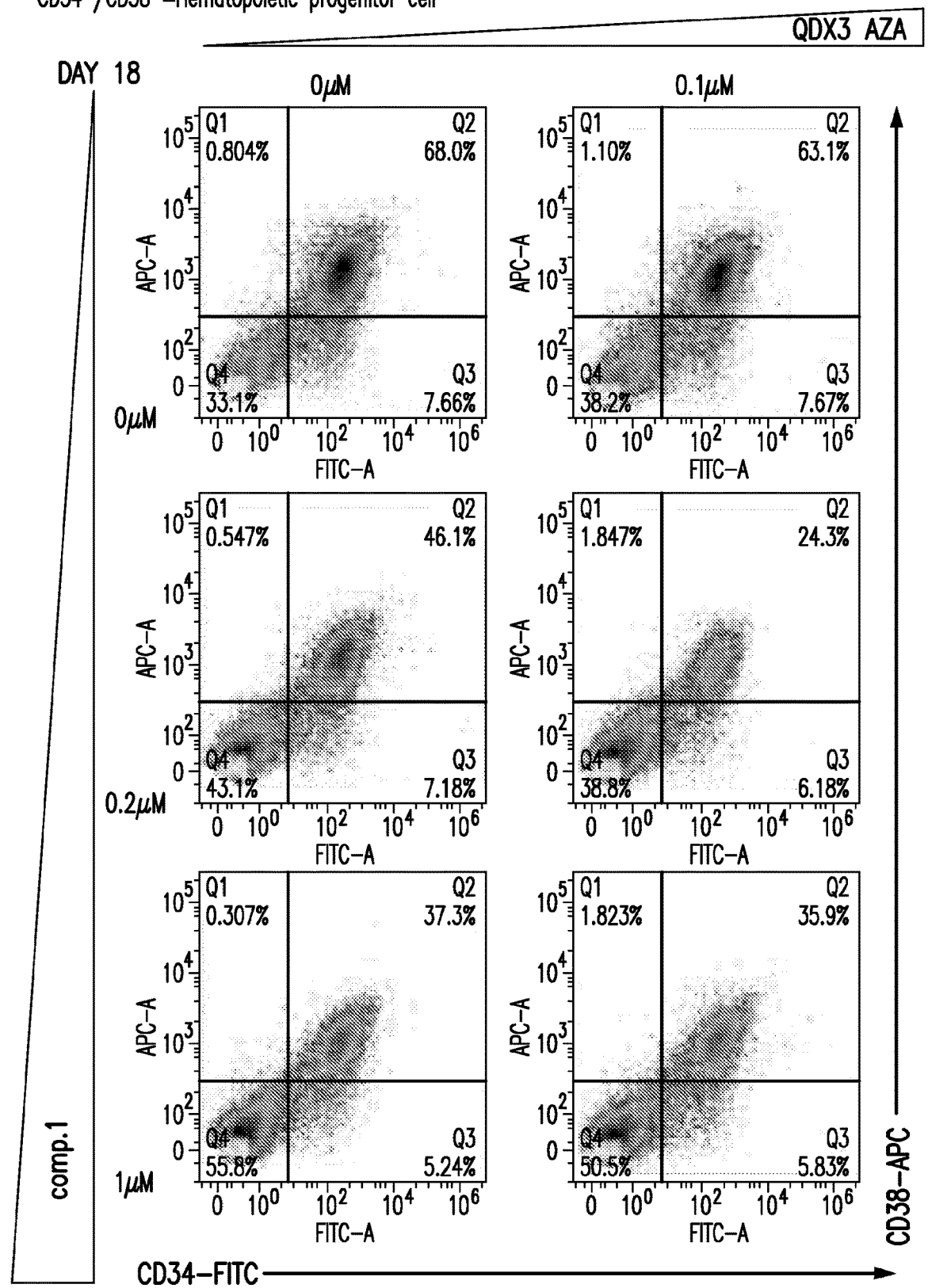
FIG. 8 depicts the effect of the combination of azacitidine and COMPOUND 1 on profiling of CD34 and CD38 markers. CD34 and CD 38 flow cytometry was performed for sequential (i) (FIG. 8A) and concurrent (ii) (FIG. 8B) schedules.
Figure 8A:
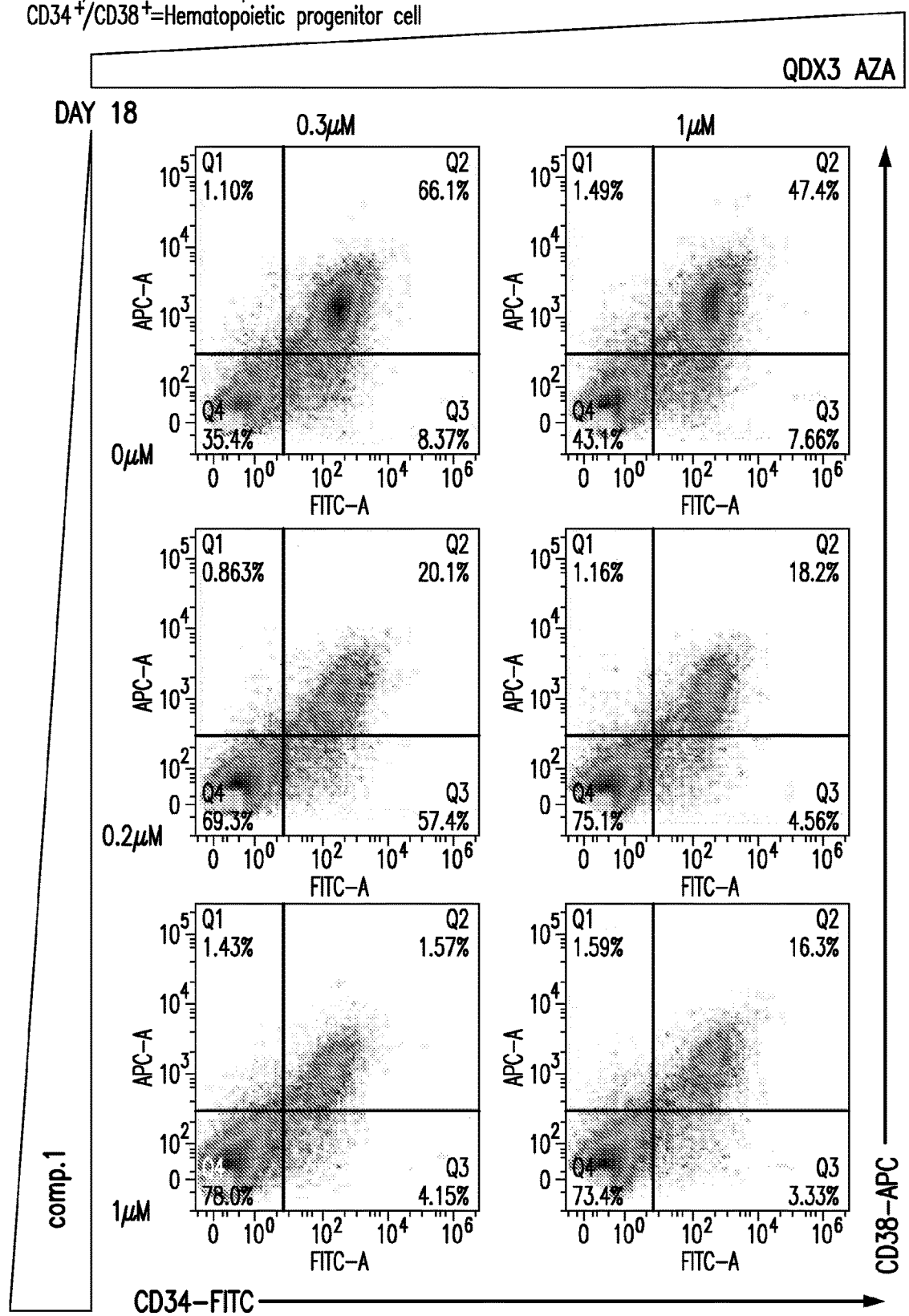
Figure 8B:
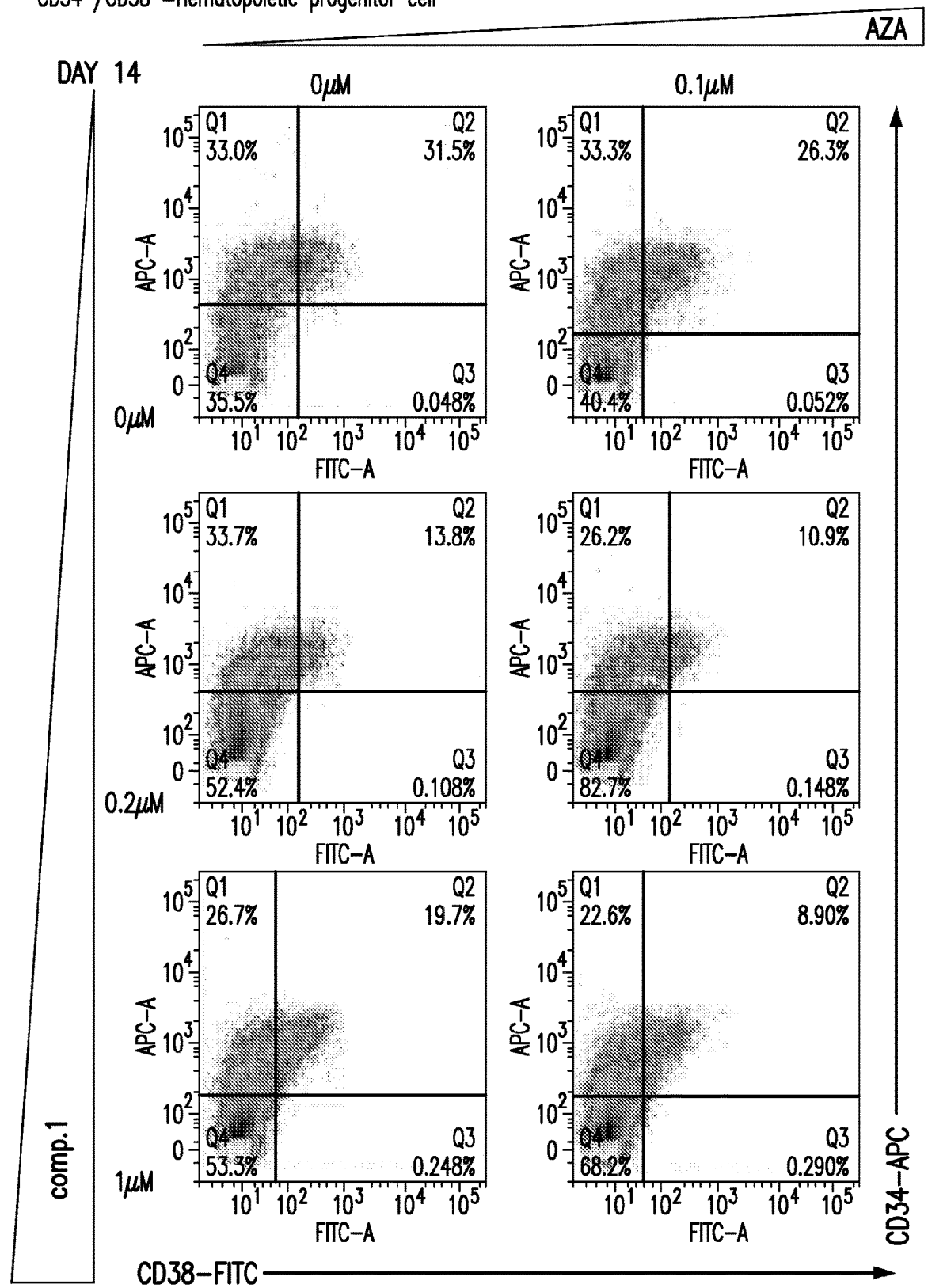
Figure 8B:
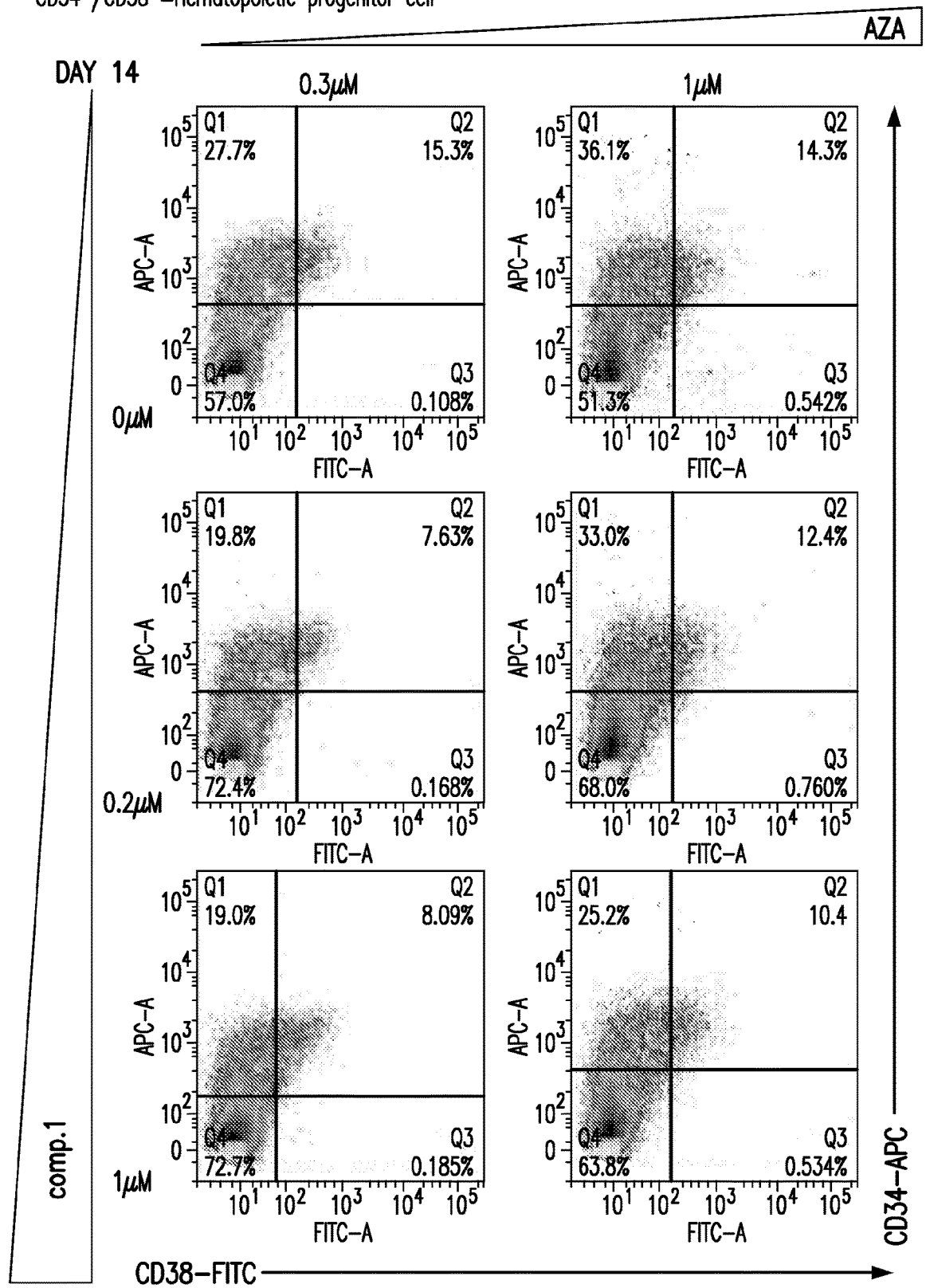
Figure 9A:
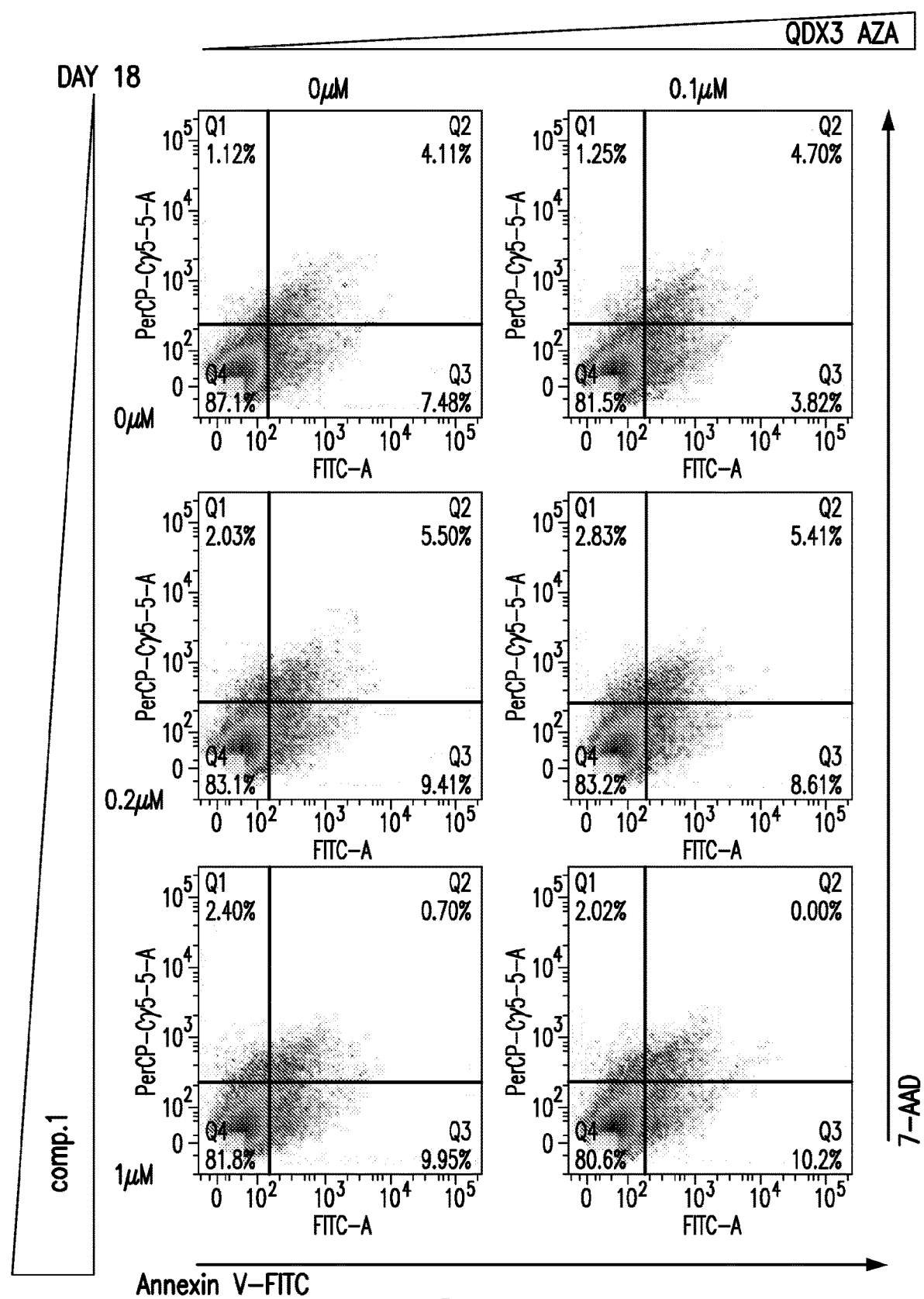
FIG. 9 depicts the effect of the combination of azacitidine and COMPOUND 1 on AnnexinV/7-ADD profiling. The cells were subjected to AnnexinV/7-ADD flow cytometry performed for sequential (i) (FIG. 9A) and concurrent (ii) (FIG. 9B) schedules.
Figure 9A:
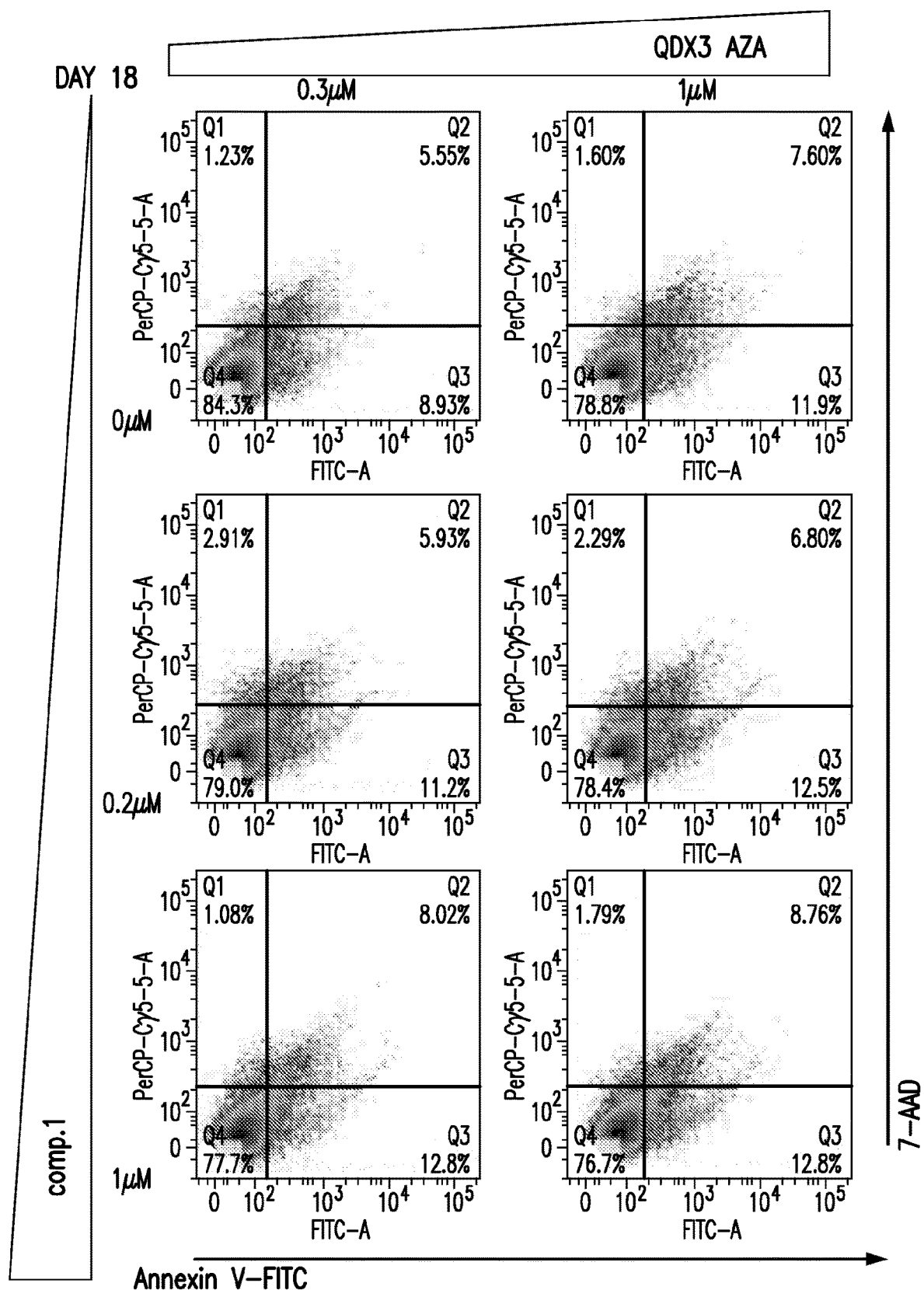
Figure 9B:
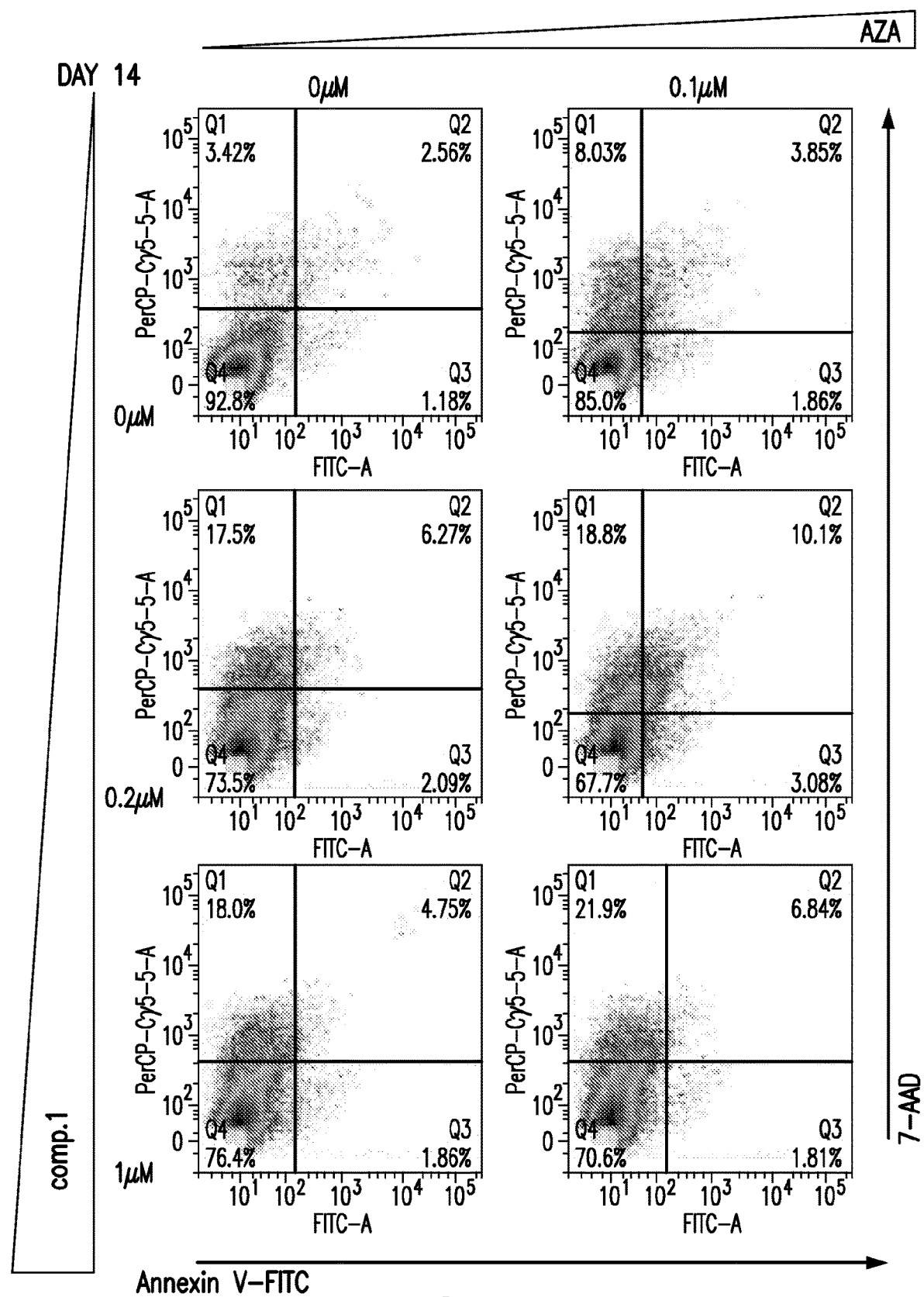
Figure 9B:
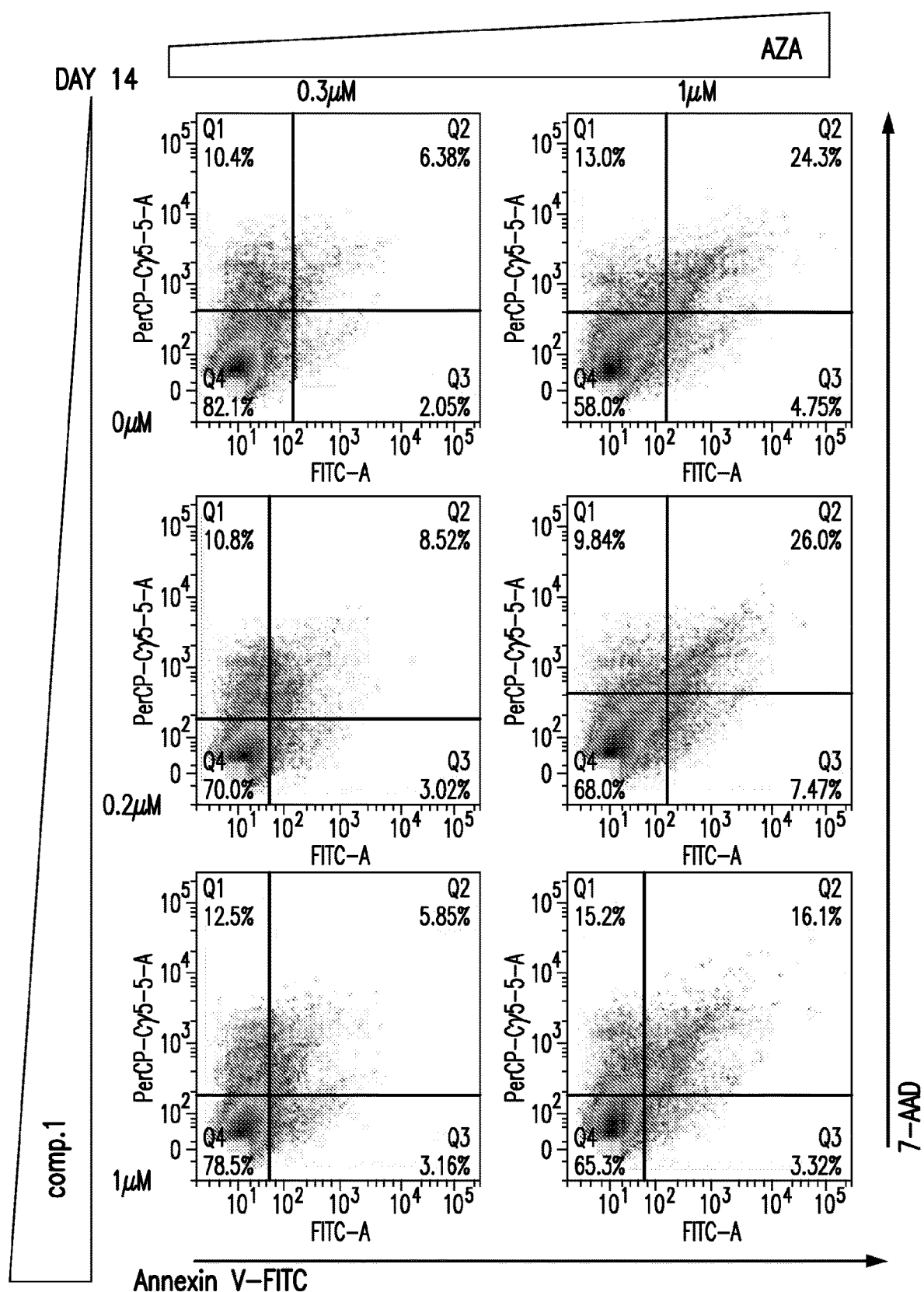

Dose-dependent increases in RNA expression of differentiation markers KLF1 and HBG were observed with both single agents. Sequential combination of azacitidine and COMPOUND 1 resulted in additive or greater than additive increases of those parameters (FIG. 2Aii, iii). For example, COMPOUND 1 (0.2 µM) and azacitidine (0.3 µM) as single agents showed 241-fold and 92-fold increases in HBG gene expression, respectively (FIG. 2A,iii), while the combination of azacitidine (0.3 µM) and COMPOUND 1 (0.2 µM) resulted in a 530-fold increase, which is 59% higher than the combined fold increases of single agents (FIG. 2A,iii). The sequential combination of azacitidine and COMPOUND 1 also reduced the overall time to EPO-induced differentiation, as evidenced by more rapid haemoglobinization. While 7 days was required to observe increased red color of cells with COMPOUND 1 as a single agent, this increase in haem production was visually evident by day 4 post-EPO with the combination of agents (FIG. 7).

Similar results on haemoglobinization (FIG. 2Bi), KLF1 expression (FIG. 2Bii) and HBG expression (FIG. 2Biii) were observed with the concurrent dosing regimen. COMPOUND 1 alone (0.2 and 1 µM) increased hemoglobin production upon EPO differentiation in a dose-dependent manner. Azacitidine alone also increased hemoglobin production at 0.1 and 0.3 µM concentrations, although cell death occurred at 1 M, as evidenced by decreased cell pellet sizes. The combined effect of azacitidine and COMPOUND 1 resulted in noticeably greater coloration/hemoglobinization than with single agents (FIG. 2Bi).

Figure 2B:
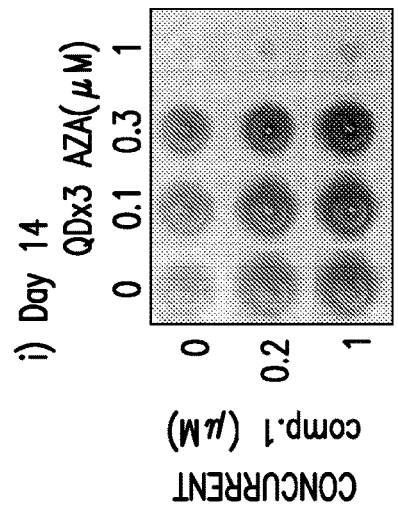
FIG. 2B depicts the effect of the combination of azacitidine and COMPOUND 1 used concurrently on differentiation markers. The pellets were observed for hemoglobinization on day 14 (i). Treated cells were subjected to qRT-PCR (ii) and to HBG qRT-PCR (iii).
Figure 2B:
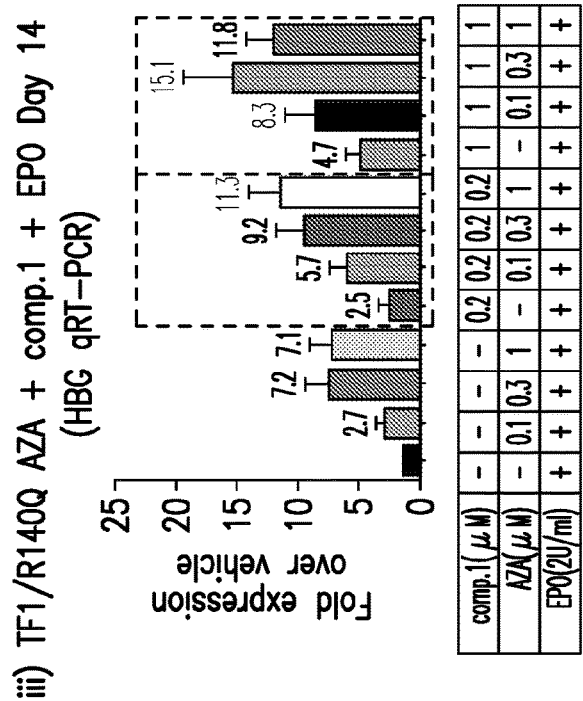
Figure 2B:
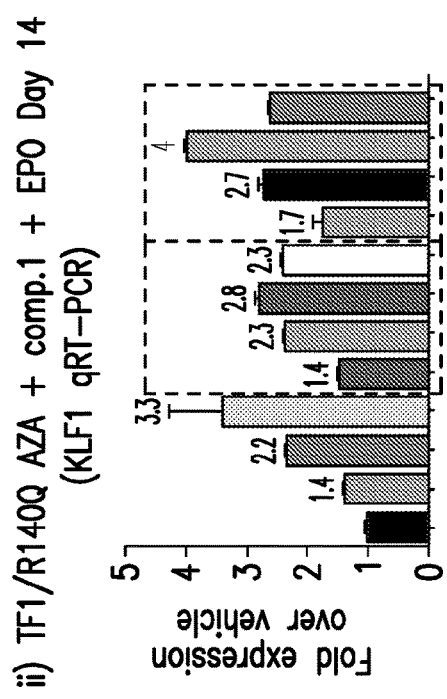

Dose-dependent increases in RNA expression of differentiation markers KLF1 and HBG were observed with azacitidine and COMPOUND 1 as single agents, and concurrent combination of azacitidine and COMPOUND 1 resulted in additive or greater than additive increases in RNA expression (FIG. 2Bii,iii). For example, COMPOUND 1 (0.2 µM) and azacitidine (1 µM) as single agents showed 2.5-fold and 7.1-fold increases in HBG gene expression, respectively (FIG. 2 Biii), while the combination of azacitidine (1 µM) and COMPOUND 1 (0.2 µM) resulted in a 11.3-fold increase, which is 18% higher than the combined fold increases of single agents (FIG. 2 Biii).

Enhanced Depletion of Hematopoietic Progenitor and Stem Cells

Figure 3:
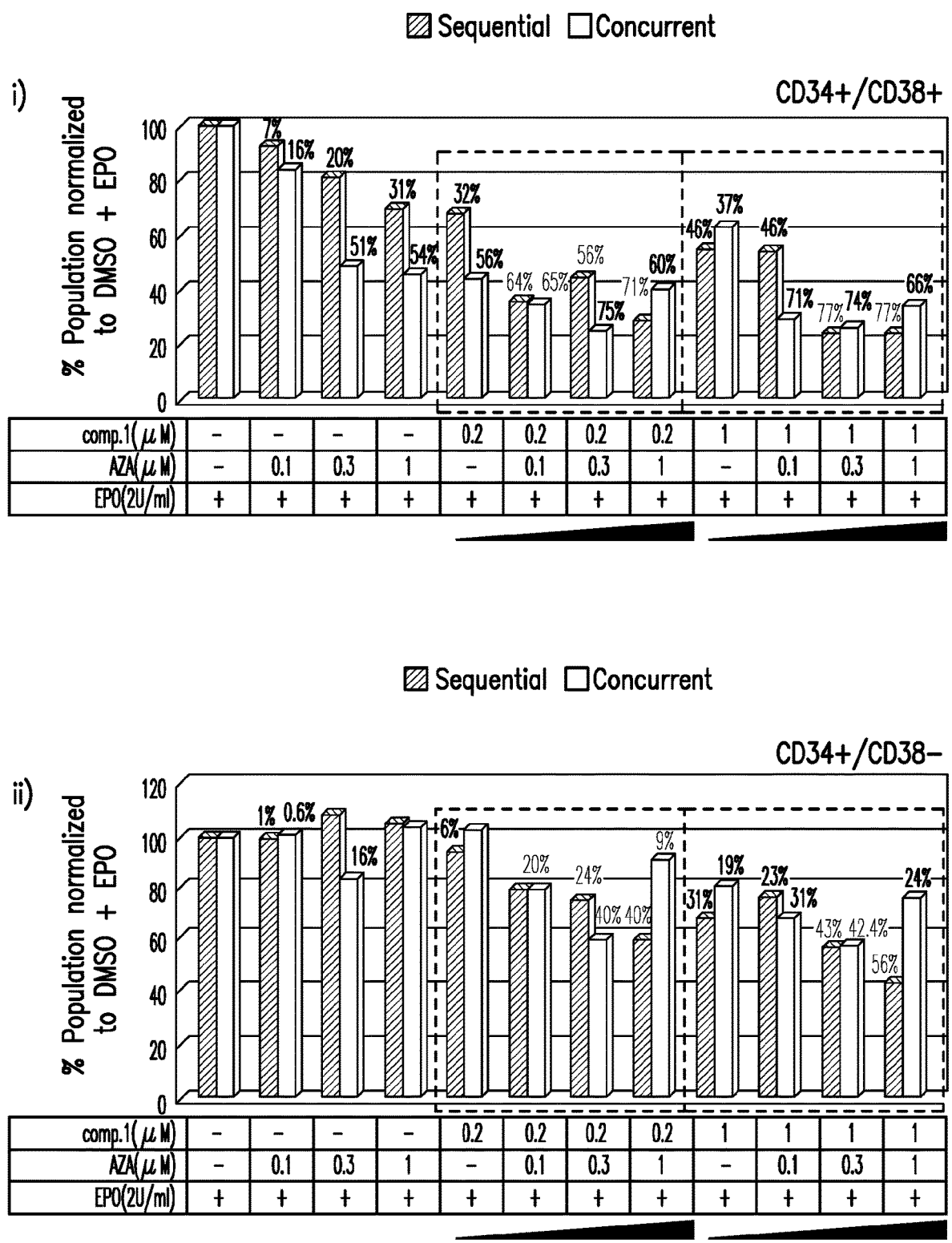
FIG. 3 depicts the effect of the combination of azacitidine and COMPOUND 1 on stem cell markers. Flow cytometry analysis was performed for sequential and concurrent schedules. Hematopoietic progenitor cells (CD34+/CD38+) (i) and stem cells (CD34+/CD38−) (ii) populations were normalized to DMSO+EPO and plotted. Values for population percentage decreases are shown, with those in red font depicting greater than additive effect with the combination as compared to AZA or COMPOUND 1 as single agents.

The hematopoietic stem (CD34+/CD38−) and progenitor (CD34+/CD38+) cell populations were quantified at the end of the EPO-differentiation assay (FIGS. 3 and 8). As single agents, both azacitidine and COMPOUND 1 reduced CD34+/CD38+(FIG. 3i) and CD34+/CD38− (FIG. 3ii) cell populations. The combination of azacitidine and COMPOUND 1 resulted in additive or greater than additive decreases. For example, COMPOUND 1 (0.2 µM) and azacitidine (0.1 µM) as single agents decreased hematopoietic progenitor cells (CD34+/CD38+) by 32% and 7%, respectively, with sequential treatment, while the combination of azacitidine (0.1 µM) and COMPOUND 1 (0.2 µM) decreased the hematopoietic progenitor cell population by 64% (FIG. 3i).

COMPOUND 1(0.2 µM) and azacitidine (0.1 µM) as single agents had no effect (<10% decrease) on the hematopoietic stem cell population with sequential or concurrent treatment regimens (FIG. 3ii), however, their combination in the same concentrations decreased the hematopoietic stem population by 20% in both the sequential and concurrent regimens (FIG. 3ii).

These data demonstrate a greater than additive effect of the combination of COMPOUND 1 and azacitidine on depleting leukemic stem and progenitor populations of TF1-R140Q cells.

Enhanced Cell Death

Figure 4:
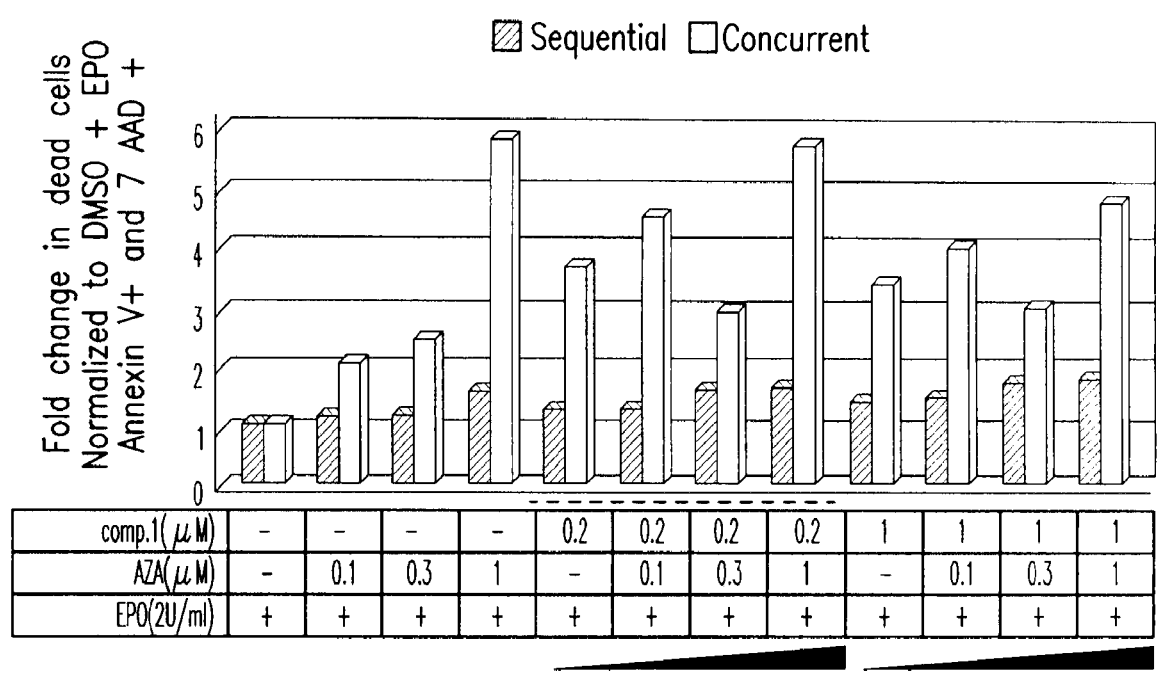
FIG. 4 depicts the effect of the combination of azacitidine and COMPOUND 1 on cell death markers. Annexin V and 7-AAD flow cytometry analysis was performed for sequential (day 18) and concurrent (day 14) dosing schedules. Populations were normalized to DMSO+EPO and fold change of percent Annexin V+ and/or 7-AAD+ was plotted.

Cell death was analyzed via Annexin V/7-AAD flow cytometry at the end of the EPO-differentiation assay (FIGS. 4 and 9). In the sequential dose-schedule regimen, there was no induction (<2-fold) of death (AnnexinV+ and/or 7AAD+) with a single agent. In the concurrent dose-schedule regimen, azacitidine and COMPOUND 1 as single agents increased the percentage of AnnexinV+ and/or 7AAD+ cells by 3.4-fold and 3.5-fold (average values across dose concentrations), respectively. There was no enhancement of cell death with the combination of agents using either sequential or concurrent treatment regimens.

Figure 5:
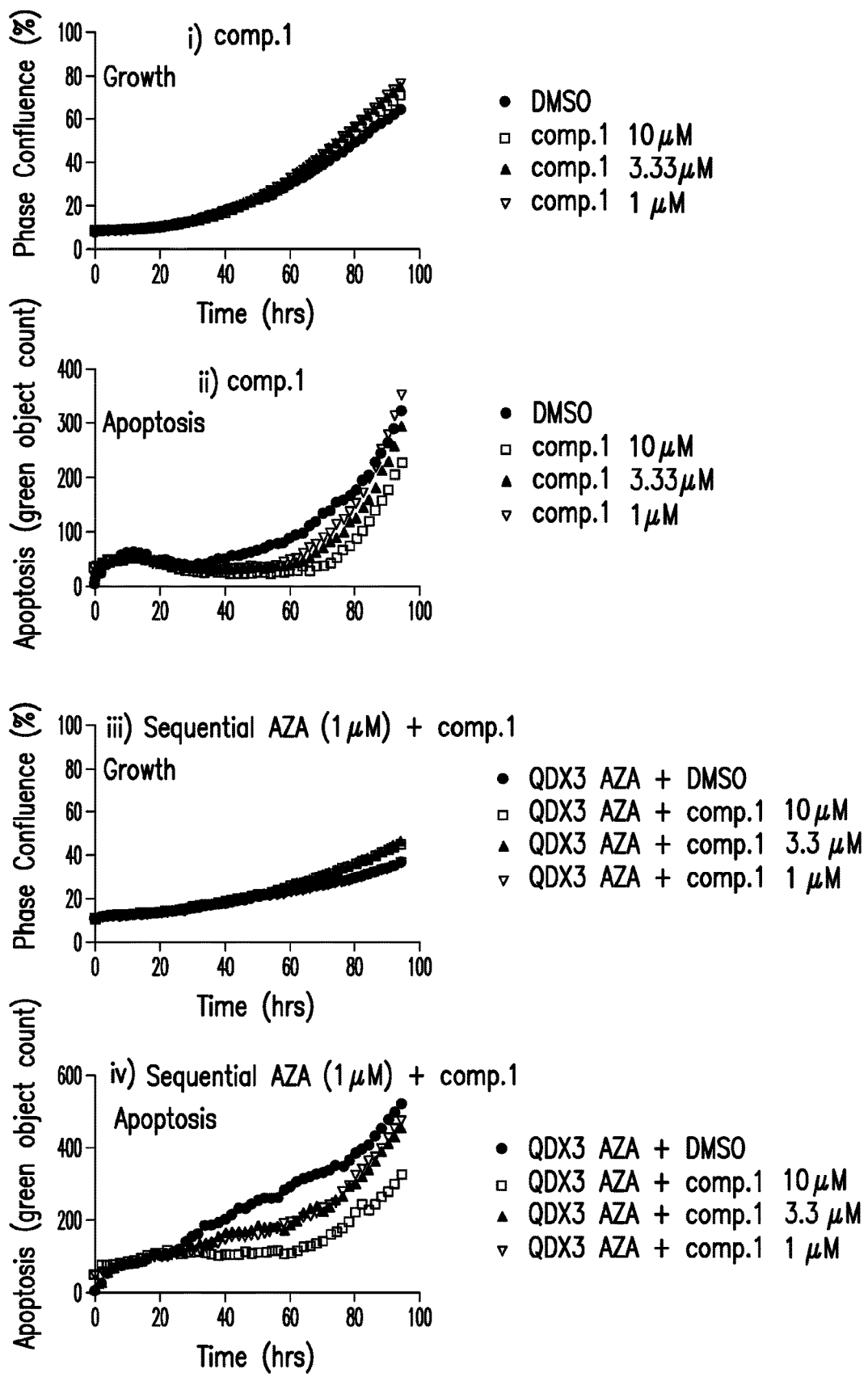
FIG. 5 depicts the effect of the combination of azacitidine and COMPOUND 1 used sequentially on real time growth (i) and (iii) and apoptosis (ii) and (iv) (IncuCyte Zoom). The TF-1 R140Q cells were pre-treated in bulk in flasks with 1 μM of QDx3 azacitidine and then plated with COMPOUND 1 concentrations of 10, 3 and 0.3 μM and Caspase 3/7 dye (obtained from Essen Biosciences) to monitor real-time growth and apoptosis on IncuCyte Zoom up to 104 hrs.
Figure 6:
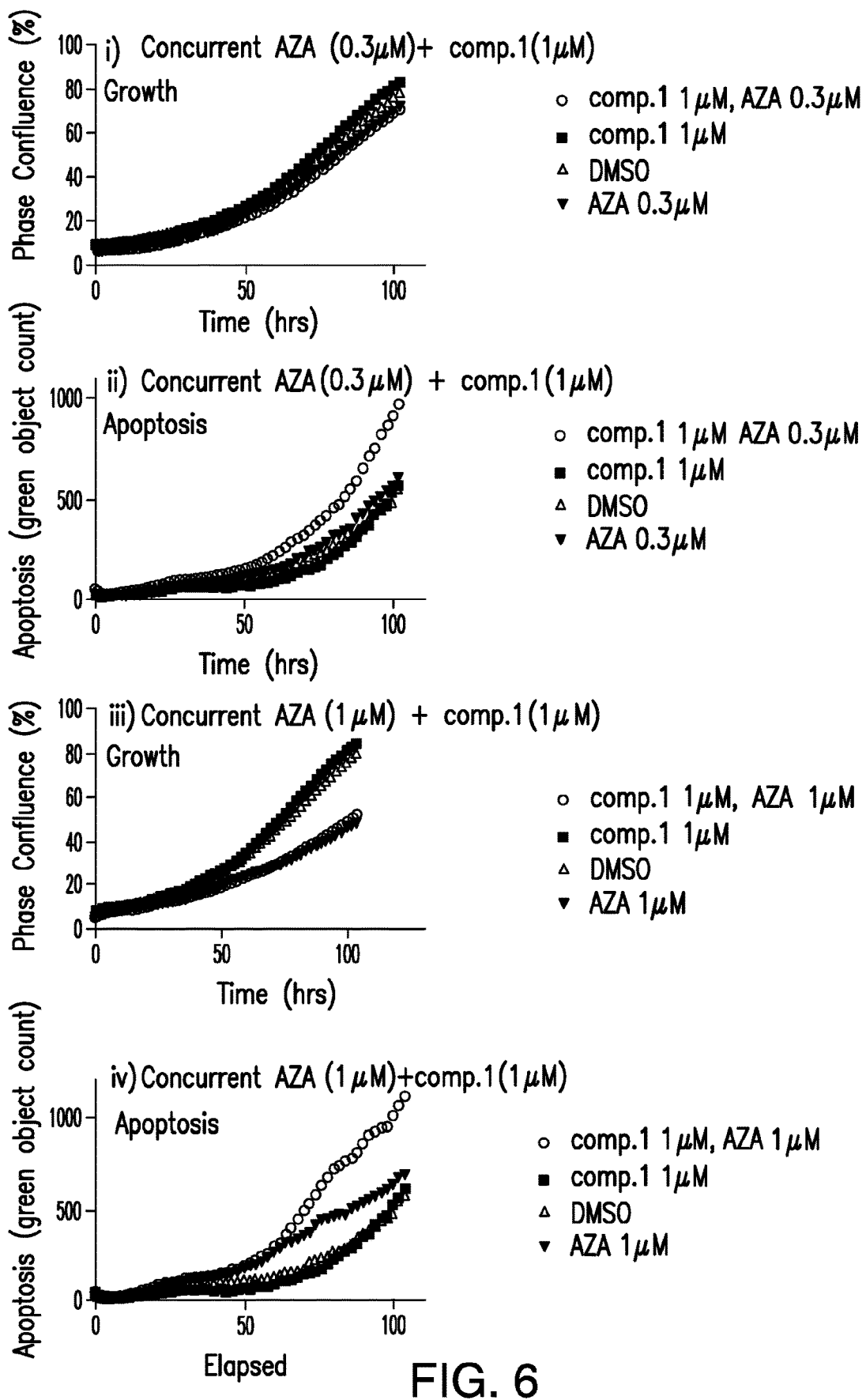
FIG. 6 depicts the effect of the combination of azacitidine and COMPOUND 1 used concurrently on real time growth (i) and (iii) and apoptosis (ii) and (iv) (IncuCyte Zoom). The TF-1 R140Q cells were plated with the combination of azacitidine (1 and 0.3 μM) and COMPOUND 1 (1 μM) and imaged for real-time growth and apoptosis on IncuCyte Zoom up to 104 hrs.

A real-time death analysis was performed using IncuCyte Zoom (FIGS. 5 and 6). At concentrations 1-10 µM COMPOUND 1 had no effect on cell growth, while azacitidine (1 µM) reduced growth and increased apoptosis (FIG. 5$i$ vs FIG. 5$iii$; FIG. 5$ii$ vs FIG. 5$iv$). Sequential treatment with both agents did not further reduce growth or increase apoptosis beyond that observed with azacitidine alone (FIG. 5$iii$, 5$iv$).

The concurrent combination of azacitidine (0.3 µM) and COMPOUND 1 (1 µM) did not affect cell growth (FIG. 6$i$), but increased cell kill (77% increase at 104 hrs) beyond that of single agents (FIG. 6$ii$). The increased death with the combination of agents is notable, considering the lack of death induction with either single agent at these concentrations. The combination of azacitidine (1 M) and COMPOUND 1(1 µM) decreased growth (32% decrease at 104 hrs) (FIG. 6$iii$) and increased apoptosis (95% increase at 104 hrs) in comparison to single agents (FIG. 6$iii$, 6$iv$). In summary, COMPOUND 1 as single agent had no effect on a caspase 3/7 death measure, however a concurrent dose-schedule regimen of the combination potentiated the single agent effect of azacitidine.

Together these results indicate a novel combination paradigm for combining AZA and COMPOUND 1 to benefit IDH2-mutant AML patients, and more particularly IDH2$^{R140Q}$-mutant AML patients. Based on this mechanism, the combination can be translated to other IDH2$^{R140Q}$-mutant cancers.

Example 2. Phase 1b/2 Open-Label, Randomized Study of 2 Combinations of Isocitrate Dehydrogenase (IDH) Mutant Targeted Therapies Plus Azacitidine: Oral COMPOUND 2 Plus Subcutaneous Azacitidine and Oral COMPOUND 1Plus SC Azacitidine in Subjects with Newly Diagnosed Acute Myeloid Leukemia Harboring an IDH1 or an IDH2 Mutation, Respectively, Who are not Candidates to Receive Intensive Induction Chemotherapy Indication:

Treatment of patients 18 years and older with newly diagnosed acute myeloid leukemia (AML) harboring an IDH1 or an IDH2 mutation who are not candidates to receive intensive induction chemotherapy (IC).

Key Objectives—Phase 1b (Dose-Escalation Stage)

Primary Objectives

To assess the safety and tolerability of the combination treatments of oral (S)—N—((S)-1-(2-chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide) (hereafter COMPOUND 2) plus subcutaneous (SC) azacitidine and oral COMPOUND 1 plus SC azacitidine in subjects with newly diagnosed AML harboring an IDH1 or an IDH2 mutation, respectively, who are not candidates to receive intensive IC.

To establish the recommended Phase 2 dose (RP2D) of oral COMPOUND 2 and oral Compound 1 when administered with SC azacitidine.

Secondary Objective

To assess the preliminary efficacy of the combination treatments of oral COMPOUND 2 plus SC azacitidine and oral COMPOUND 1 plus SC azacitidine in subjects with newly diagnosed AML harboring an IDH1 or an IDH2 mutation, respectively, who are not candidates to receive intensive IC.

Phase 2 (Randomized Stage)

Primary Objective

To assess the efficacy of the combination treatments of oral COMPOUND 2 plus SC azacitidine and oral COMPOUND 1+SC azacitidine versus SC azacitidine in subjects with newly diagnosed AML harboring an IDH1 or an IDH2 mutation, respectively, who are not candidates to receive intensive IC.

Secondary Objectives

To evaluate the safety of oral COMPOUND 2 and oral COMPOUND 1 when administered with SC azacitidine.

To characterize the pharmacokinetics (PK) of oral COMPOUND 2, COMPOUND 1, and SC azacitidine when administered in combination.

To evaluate the PK and PD relationships of oral COMPOUND 2 and oral COMPOUND 1 when administered with SC azacitidine with the suppression of 2-hydroxyglutarate (2-HG) levels in bone marrow and plasma samples.

To evaluate the effect of oral COMPOUND 2 and oral COMPOUND 1 when administered with SC azacitidine versus SC azacitidine alone on health-related quality-of-life (HRQoL) outcomes.

Study Design

This Phase 1b/2 study is an open-label, randomized, multicenter trial to evaluate the safety and efficacy of oral COMPOUND 2+SC azacitidine and oral COMPOUND 1+SC azacitidine in subjects with newly diagnosed AML harboring an IDH1 or an IDH2 mutation, respectively. The study population consists of subjects who are not candidates to receive intensive IC. The study comprises a Phase 1b dose-escalation stage and a Phase 2 randomized stage.

Phase 1b Dose-Finding Stage

The Phase 1b stage is an open-label dose-finding study to evaluate the safety and tolerability of the combinations of oral COMPOUND 2 and oral COMPOUND 1 with SC azacitidine to define the RP2Ds of these 2 agents when administered in combination with SC azacitidine. The preliminary clinical activities of the oral COMPOUND 2+SC azacitidine and the oral COMPOUND 1+SC azacitidine regimens will also be assessed.

The Phase 1b stage consists of 3 periods: 1) screening; 2) treatment; and 3) follow-up.

Subject screening procedures will occur during the screening period within 28 days prior to the start of study treatment. The diagnosis of AML with an IDH mutation will be based on local review of both hematopathology and IDH gene mutation testing of bone marrow aspirate and/or peripheral blood samples. Subjects eligible for enrollment must not be candidates to receive intensive IC, based on the investigator's judgment, due to the presence of co-morbidities, declining performance status, or other factors. Subjects with newly diagnosed AML harboring an IDH1 mutation will be assigned to the oral COMPOUND 2+SC azacitidine arm, and subjects with newly diagnosed AML harboring an IDH2 mutation will be assigned to the oral COMPOUND 1+SC azacitidine arm. In the rare case in which a subject is diagnosed with an AML associated with dual IDH1 and IDH2 mutations, assignment to the oral COMPOUND 2 or COMPOUND 1 treatment arm will be based on a joint investigator and medical monitor decision and documented in the source.

During the treatment period a standard 3+3 design will be used. A Dose Review Team (DRT), consisting of a medical monitor, lead safety physician, biostatistician, other functional area representatives or designees, as appropriate, and all active site investigators and/or designees (at sites with a subject who has received study drug), will review all adverse events (AEs) experienced by subjects during Cycle 1 of each dose level to determine whether the maximum tolerated dose (MTD) of oral COMPOUND 2 or COMPOUND 1 when administered in combination with SC azacitidine has been exceeded. One dose level of oral COMPOUND 2 (500 mg daily) and 2 dose levels of oral COMPOUND 1 (100 mg daily and 200 mg daily) are planned to be evaluated. Dose levels lower than 500 mg daily for oral COMPOUND 2 and lower than 100 mg daily for oral COMPOUND 1 will be evaluated if these doses in combination with SC azacitidine are found to exceed the MTD during Cycle 1. Dose interruptions/delays and dose reductions may be used to manage toxicities. Subjects may receive study treatment until disease progression/relapse, study treatment becomes intolerable, or the subject wishes to discontinue study treatment for any reason. Response to treatment will be assessed by the investigators according to the modified International Working Group (IWG) AML Response Criteria (Cheson, et al. J Clin Oncol 2003; 21(24):4642-9). Hematologic improvement (HI) will be assessed according to the IWG myelodysplastic syndromes HI criteria (Cheson et al, Blood 2006; 108(2):419-25). Subjects are to undergo end-of-treatment evaluations when study treatment is discontinued. The reason for treatment discontinuation will be recorded in the electronic case report form (eCRF) pages and in the source document.

All subjects discontinued from study treatment for any reason other than withdrawal of consent for follow-up will continue to be assessed for AEs, concomitant medications, concomitant procedures, transfusions, healthcare resource utilization, response, hematologic improvement, subsequent AML therapies, and survival.

All subjects discontinued from study treatment for any reason except withdrawal of consent for follow-up or disease progression will continue to be assessed during the Follow-up period of the study for response until disease progression.

All subjects discontinued from study treatment for any reason except withdrawal of consent for follow-up will continue to be assessed for subsequent AML therapies, and survival.

The study will be conducted in compliance with the International Conference on Harmonization (ICH) Good Clinical Practices (GCPs) guidelines.

Phase 2 Randomized Stage

The Phase 2 stage is an open-label randomized study to evaluate the efficacy of the combinations of oral COMPOUND 2 and oral COMPOUND 1 with SC azacitidine versus SC azacitidine alone in order to assess the overall response rate (ORR), event-free survival (EFS), and morphologic complete remission (CR).

The Phase 2 stage will also consist of 3 periods: 1) screening; 2) treatment; and 3) follow-up.

As with Phase 1b, subject screening procedures will occur during the screening period within 28 days prior to the start of study treatment, but the diagnosis of AML will be performed locally for enrollment and confirmed based on a subsequent central review. The IDH mutation will be assessed centrally using samples of both bone marrow aspirate and/or peripheral blood. Subjects eligible for enrollment are those who are not candidates to receive intensive IC, based on the investigator's judgment, due to the presence of co-morbidities, declining performance status, or other factors.

Following review of eligibility, subjects with newly diagnosed AML harboring an IDH1 or IDH2 mutation will be randomized in a 2:1 ratio to 1 of 3 arms. Subjects with IDH1 mutation will be randomized to receive oral COMPOUND 2+SC azacitidine (Arm 1) versus SC azacitidine (Arm 3) in a 2:1 ratio; and subject with IDH2 mutation will be randomized to receive oral COMPOUND 1+SC azacitidine (Arm 2) versus SC azacitidine (Arm 3) in a 2:1 ratio. Arms 1 and 2 will randomize a minimum of 50 subjects, and Arm 3 will randomize a minimum of 25 IDH1 and 25 IDH2 (50 subjects total in Arm 3) (150 subjects total in all arms). In the rare case in which a subject is diagnosed with an AML associated with dual IDH1 and IDH2 mutations, randomization to the oral COMPOUND 2 or COMPOUND 1 treatment arm will be based on an investigator and medical monitor decision.

Subjects will be stratified by cytogenetics (better or intermediate versus poor cytogenetic risk.

Study treatment will start the same day as randomization. Assessments during study treatment include efficacy, safety, HRQoL, healthcare resource utilization, pharmacokinetics, pharmacodynamics, and correlative studies.

A retrospective central review of all bone marrow aspirates and/or biopsies, peripheral blood smears, and cytogenetics collected during the study will be conducted by personnel blinded to subject treatment. The central assessments will be used in the statistical analyses. Disagreement between central and local assessments will be adjudicated by a third party reviewer and the adjudicated assessment will be used in the statistical analyses.

Response to treatment and HI will be assessed by the investigators and retrospectively by a blinded Independent Response Assessment Committee (IRAC) according to modified IWG AML Response Criteria (Cheson, J Clin Oncol 2003; 21(24):4642-9) and IWG myelodysplastic syndromes HI criteria (Cheson, et al, Blood 2006; 108(2):419-25), respectively.

Dosing interruptions, dosing delays or dose modifications may occur for managing toxicities and/or augmenting treatment response during study treatment and.

The discontinuation of COMPOUND 2, COMPOUND 1, or azacitidine for subjects in the combination arms of the study is allowed. Subjects may continue treatment with single agent COMPOUND 2, COMPOUND 1, or azacitidine if in the investigator's assessment the subject continues to show clinical benefit and all protocol-specified criteria for continuing study treatment are met. Study treatment will be discontinued if the subject has progressive disease or receives alternative therapies.

The decision to discontinue a subject, which will not be delayed or refused by the sponsor, remains the responsibility of the treating physician. However, prior to discontinuing a subject, it is recommended that the investigator contact the medical monitor and forward appropriate supporting documents for review and discussion.

All subjects who have received at least one dose of study treatment should undergo End of Treatment (EOT) evaluations when study treatment is discontinued. The reason for discontinuation will be recorded in the electronic case report form (eCRF) pages and in the source document.

All subjects discontinued from study treatment for any reason other than withdrawal of consent for follow-up will continue to be assessed for AEs, concomitant medications, concomitant procedures, transfusions, healthcare resource utilization, response, hematologic improvement, subsequent AML therapies, and survival.

All subjects discontinued from study treatment for any reason except withdrawal of consent for follow-up or disease progression will continue to be assessed during the Follow-up period of the study for response until disease progression.

All subjects discontinued from study treatment for any reason except withdrawal of consent for follow-up will continue to be assessed for subsequent AML therapies, and survival.

The study will be conducted in compliance with International Conference on Harmonization (ICH) Good Clinical Practices (GCPs).

Length of Study

The full length of the study is expected to be approximately 60 months including recruitment, screening, treatment, and follow up for Phase 1b and Phase 2. Recruitment is expected to take 7 months for Phase 1b, and 17 months for Phase 2. For a single subject, the expected duration of the Phase 1b segment of the study is approximately 13 months, including a screening period for up to 28 days, and the expected duration of the Phase 2 segment of the study is approximately 25 months, including a screening period for up to 28 days.

The End of Trial is defined as either the date of the last visit of the last subject to complete the post-treatment follow-up, or the date of receipt of the last data point from the last subject that is required for primary, secondary, and/or exploratory analysis, as pre-specified in the protocol, whichever is the later date.

The trial will continue until the required amount of EFS events for full statistical power occur.

Study Treatments

COMPOUND 2 and COMPOUND 1 are administered orally once a day (QD) on Days 1-28 of each 28-day cycle. Subjects should be instructed to take their daily dose at approximately the same time each day±4 hours. Each dose should be taken with a glass of water and consumed over as short a time as possible. Subjects should be instructed to swallow tablets whole and to not chew the tablets. Fasting is required for 2 hours prior to and 1 hour following COMPOUND 2 or COMPOUND 1 administration. Water is allowed during fasting.

Azacitidine will be administered SC for 7 days of each 28-day treatment cycle starting on Day 1 during both Phase 1b and Phase 2. During the Phase 2 stage, subjects randomized to the azacitidine alone arms will receive azacitidine 75 mg/m$^2$/day SC for 7 days of each 28-day cycle. All randomized subjects will receive azacitidine 75 mg/m$^2$/day SC for 7 days every 28 days until the end of the study, unless they are discontinued from the treatment. In addition, subjects may receive best supportive care as needed, including antibiotics and transfusions, per investigator discretion. In the event that 2 or fewer doses are missed during the 7-day dosing period, dosing should continue so the subject receives the full 7 days of therapy. If 3 or more days are missed during the 7-day dosing period, the investigator should contact the sponsor and a decision on dosing will be made on a case-by-case basis.

Phase 1b:

Phase 1b will use a 3+3 design. For COMPOUND 2 one dose level will be explored enrolling 3 subjects. Cohort 1 will be initiated with oral COMPOUND 2 500 mg once a day and azacitidine 75 mg/m$^2$/day SC for 7 days of each 28-day cycle starting on Day 1 of each cycle. A Cohort −1 will be explored at 250 mg once a day and azacitidine 75 mg/m$^2$/day SC for 7 days of each 28-day cycle if 2 or more subjects in Cohort 1 have a dose-limiting toxicity (DLT) in Cohort 1.

For COMPOUND 1 two dose levels will be explored. Cohort 1 will be initiated with oral COMPOUND 1 100 mg once a day and azacitidine 75 mg/m$^2$/day SC for 7 days of each 28-day cycle starting on Day 1 of each cycle. If no DLTs are observed, the RP2D will be confirmed by the DRT and the 100 mg dose will be used as the starting dose for the Phase 2 segment of the study. Dose escalation to Cohort 2 will also be initiated with oral COMPOUND 1 200 mg once a day and azacitidine 75 mg/m$^2$/day SC for 7 days of each 28-day cycle starting on Day 1 of each cycle to explore the tolerability of the combination at this dose level. A Cohort −1 with oral COMPOUND 1 50 mg daily and azacitidine 75 mg/m$^2$/day SC for 7 days of each 28-day cycle starting on Day 1 of each cycle will be explored if 2 or more subjects have a DLT in Cohort 1.

The DRT will evaluate all toxicities of each subject after 1 cycle and determine whether further dose modifications are needed for individual subjects.

Phase 2:

COMPOUND 2 Combination Arm:

Subjects with an IDH1 mutation will receive COMPOUND 2 at the RP2D orally QD on Days 1-28 of each 28-day cycle+azacitidine 75 mg/m$^2$/day SC for 7 days of each 28-day cycle.

COMPOUND 1 Combination Arm:

Subjects with an IDH2 mutation will receive COMPOUND 1 at the RP2D orally QD on Days 1-28 of each 28-day cycle+azacitidine 75 mg/m$^2$/day SC for 7 days of each 28-day cycle.

Azacitidine Alone Arm:

Subjects with either an IDH1 or IDH2 mutation will receive azacitidine 75 mg/m$^2$/day SC for 7 days of each 28-day cycle.

Overview of Key Efficacy Assessments

Efficacy

Serial blood and bone marrow sampling will be used to determine response to therapy starting at Cycle 2. Response will be assessed locally during Phase 1b. During Phase 2, response will be assessed locally and confirmed centrally according to the modified IWG criteria based on the reported hematology laboratory parameters, peripheral blood smear, bone marrow aspirates and/or biopsies, and cytogenetics.

Subjects who discontinue study treatment prior to relapse or progression will complete monthly site visits until confirmation of relapse or progression. For subjects who have discontinued study treatment due to relapse or progression, monthly follow up can be performed by site visits or phone calls. Subjects will be followed until they have died, are lost to follow up, withdraw consent for further data collection, or until study closure.

Overview of Other Key Assessments

Safety

Safety assessments include adverse events, physical examination, Eastern Cooperative Oncology Group (ECOG) performance status, vital signs, echocardiogram (ECHO) or multi-gated acquisition (MUGA) scan, electrocardiogram (ECG), cardiac markers, urinalysis, coagulation, hematology, serum chemistry, transfusions, pregnancy testing (for females of child bearing potential (FCBP) only), and concomitant medications or procedures.

Plasma PK/PD of COMPOUND 2 and COMPOUND 1

The PK profile of COMPOUND 2/COMPOUND 1 and azacitidine combinations will be evaluated by plasma concentrations and PK parameters of COMPOUND 2/COMPOUND 1 and azacitidine combinations in the Phase 2 segment. Plasma concentrations of 2-HG will be evaluated in relation to plasma concentrations of COMPOUND 2 or COMPOUND 1 over time.

Investigational Product Accountability

Oral COMPOUND 2 and COMPOUND 1 are dispensed on Day 1 of each treatment cycle and accounted for after completion of each treatment cycle.

Azacitidine will be administered SC by study site personnel. Accurate recording of all IP, including preparation and dosing, will be made in the appropriate section of the subject's CRF and source documents.

Statistical Methods

Phase 1b:

Statistical analyses in Phase 1b will be primarily descriptive in nature. Tabulations will be produced for disposition, demographic and baseline disease characteristics, safety, PK, PD, and clinical activity parameters. Categorical data will be summarized by frequency distributions (numbers and percentages of subjects) and continuous data will be summarized by descriptive statistics (mean, standard deviation, median, minimum, and maximum). Data will be summarized by dose level and overall when appropriate.

Phase 2:

The primary efficacy endpoint of Overall Response Rate (ORR) in Phase 2 includes responses of CR, CRp, morphologic leukemia-free state [MLFS], CRi, and PR, according to modified IWG AML response criteria. The treatment difference in ORR will be tested using the Fisher's exact test in the ITT population. This test will provide the pivotal p-value for the comparison of the ORRs of oral COMPOUND 2+SC azacitidine versus pooled azacitidine mono therapy group which includes subjects with IHD1 or IDH2 mutations and who are randomized to the azacitidine mono therapy, and ORRs of oral COMPOUND 1+SC azacitidine versus pooled azacitidine mono therapy group separately.

A maximum of 150 subjects will be randomized in this study with 50 IDH1 subjects in the oral COMPOUND 2+SC azacitidine arm, 50 IDH2 subjects in the oral COMPOUND 1+SC azacitidine arm, and a combined 50 IDH1 or IDH2 subjects in the azacitidine mono therapy arm (pooled azacitidine mono therapy). The comparisons will be conducted separately for oral COMPOUND 2+SC azacitidine versus pooled azacitidine mono therapy and COMPOUND 1+azacitidine versus pooled azacitidine mono therapy.

Inclusion Criteria

Subjects must satisfy the following criteria to be enrolled in the study:

Subject is ≥18 years of age at the time of signing the informed consent form (ICF).

Subject must understand and voluntarily sign an ICF prior to any study-related assessments/procedures being conducted.

Subject is willing and able to adhere to the study visit schedule and other protocol requirements.

Subject has previously untreated AML primary (ie, de novo) or secondary (progression of MDS or myeloproliferative neoplasms ([MPN], or therapy-related) AML according to the WHO classification with ≥20% leukemic blasts in the bone marrow: Have an IDH1 or IDH2 gene mutation (R132, R140, or R172); Validated local testing may be used to confirm eligibility for Phase 1, but central testing must be performed to confirm eligibility for Phase 2; By the investigator's assessment who are not candidates to receive intensive IC.

Subject has an Eastern Cooperative Oncology Group (ECOG) performance status of 0, 1 or 2.

Subject has adequate organ function defined as: Serum aspartate aminotransferase/serum glutamic oxaloacetic transaminase (AST/SGOT) and alanine aminotransferase (ALT/SGPT)≤3×ULN, unless considered due to leukemic organ involvement; Serum total bilirubin <1.5×ULN. Higher levels are acceptable if these can be attributed to ineffective erythropoiesis, Gilbert's syndrome (eg, a gene mutation in UGT1A1), or leukemic organ involvement; Serum creatinine<2×ULN or creatinine clearance>30 mL/min based on the Cockroft-Gault glomerular filtration rate (GFR) estimation: (140−Age)×(weight in kg)×(0.85 if female)/72×serum creatinine.

Agree to serial bone marrow aspirate/biopsies.

Females of childbearing potential (FCBP) may participate, providing they meet the following conditions: Agree to abstain from sexual intercourse or to use at least two effective contraceptive methods (oral, injectable, patch, or implantable hormonal contraceptive; tubal ligation; intrauterine device; synthetic double-barrier contraceptive with spermicide; or vasectomized partner) at screening and throughout the study, and for 4 months following the last study treatment (6 months following the last dose of azacitidine in Canada); and have a negative serum β-subunit of human chorionic gonadotropin (β-hCG) pregnancy test (sensitivity of at least 25 mIU/mL) at screening; and have a negative serum or urine (investigator's discretion under local regulations) β-hCG pregnancy test (sensitivity of at least 25 mIU/mL) within 72 hours prior to the start of study treatment in the Treatment Period (note that the screening serum pregnancy test can be used as the test prior to the start of study treatment in the Treatment Period if it is performed within the 72-hour timeframe).

Male subjects with a female partner of childbearing potential must agree to abstain from sexual intercourse or to the use of at least 2 effective contraceptive methods (eg, synthetic condoms with spermicide, etc) at screening and throughout the course of the study and should avoid fathering a child during the course of the study and for 4 months following the last study treatment (6 months following the last dose of azacitidine in Canada).

Exclusion Criteria

The presence of any of the following will exclude a subject from enrollment:

Subject is suspected or proven to have acute promyelocytic leukemia based on morphology, immunophenotype, molecular assay, or karyotype.

Subject has AML secondary to chronic myelogenous leukemia (CML).

Subject has received a targeted agent against an IDH1 or IDH2 mutation.

Subject has received prior systemic anticancer therapy, HSCT, or radiotherapy for AML. Note that hydroxyurea is allowed prior to the start of study treatment for the control of leukocytosis in subjects with white blood cell (WBC) counts>30×10⁹/L (however, hydroxyurea should not be given within 72 hours prior to and after administration of azacitidine). For subjects with secondary AML (eg, MDS or MPN) treatment for prior cancer is not exclusionary; full treatment information will be collected within the CRF.

Subject has received prior treatment with azacitidine or decitabine for MDS.

Subject has or is suspected of having central nervous system (CNS) leukemia.

Evaluation of cerebrospinal fluid is only required if CNS involvement by leukemia is suspected during screening.

Subject has immediate life-threatening, severe complications of leukemia such as uncontrolled bleeding, pneumonia with hypoxia or shock, and/or disseminated intravascular coagulation.

Subject has significant active cardiac disease within 6 months prior to the start of study treatment, including New York Heart Association (NYHA) class III or IV congestive heart failure; acute coronary syndrome (ACS); and/or stroke; or left ventricular ejection fraction (LVEF)<40% by echocardiogram (ECHO) or multi-gated acquisition (MUGA) scan obtained within 28 days prior to the start of study treatment.

Subject has prior history of malignancy, other than MDS, MPN, or AML, unless the subject has been free of the disease for >1 year prior to the start of study treatment. However, subjects with the following history/concurrent conditions are allowed: basal or squamous cell carcinoma of the skin; carcinoma in situ of the cervix; carcinoma in situ of the breast; incidental histologic finding of prostate cancer (T1a or T1b using the tumor, node, metastasis clinical staging system).

Subject is known seropositive for or has active viral infection with human immunodeficiency virus (HIV), or active infection with hepatitis B virus (HBV) or hepatitis C virus (HCV)

Subject is known to have dysphagia, short-gut syndrome, gastroparesis, or other conditions that limit the ingestion or gastrointestinal absorption of drugs administered orally Subject has uncontrolled hypertension (systolic blood pressure [BP]>180 mmHg or diastolic BP>100 mmHg)

Subject is taking the following sensitive CYP substrate medications that have a narrow therapeutic range are excluded from the study unless the subject can be transferred to other medications at least 5 half-lives prior to the start of study treatment: phenytoin (CYP2C9), S-mephenytoin (CYP2C19), thioridazine (CYP2D6), theophylline, and tizanidine (CYP1A2).

Subject is taking the breast cancer resistance protein (BCRP) transporter-sensitive substrate rosuvastatin; subject should be excluded from the study unless he/she can be transferred to other medications at least 5 half-lives prior to the start of study treatment Subject has active uncontrolled systemic fungal, bacterial, or viral infection (defined as ongoing signs/symptoms related to the infection without improvement despite appropriate antibiotics, antiviral therapy, and/or other treatment).

Subject has known or suspected hypersensitivity to any of the components of study therapy.

Subject is taking medications that are known to prolong the QT interval unless he/she can be transferred to other medications within ≥5 half-lives prior to the start of study treatment. (If equivalent medication is not available, QTc will be closely monitored)

Subject has QTc interval (ie, Fridericia's correction [QTcF])≥450 ms or other factors that increase the risk of QT prolongation or arrhythmic events (eg, heart failure, hypokalemia, family history of long QT interval syndrome) at screening.

Female subject who is pregnant or lactating.

Subject has any significant medical condition, laboratory abnormality, or psychiatric illness that would prevent the subject from participating in the study.

Subject has any condition, including the presence of laboratory abnormalities, that places the subject at unacceptable risk if he/she were to participate in the study.

Subject has any condition that confounds the ability to interpret data from the study.

In certain embodiments, AML patients treated with COMPOUND 1 and azacitidine, for example undergoing the clinical protocol provided herein, will show a treatment response. In some embodiments, the treatment response is a Complete Response (CR), a Morphologic Leukemia-free State (MLFS), a Morphologic Complete Remission with Incomplete Neutrophil Recovery (CRi), Morphologic Complete Remission with Incomplete Platelet Recovery (CRp), or a Partial Remission (PR), according to modified IWG AML response criteria. In some embodiments, the treatment response is a hematologic improvement, for example, an improvement in Neutrophil Response (Hi-N), Platelet response (HI-P), and/or Erythroyd Response (HI-E), according to IWG MDS HI criteria. In certain embodiments, AML patients treated with COMPOUND 1 and azacitidine in the methods provide herein will show an improvement in event-free survival (EFS), duration of response, HRQoL and/or overall survival.

Example 3

A Phase 1b/2 Open-Label, Randomized Study of 2 Combinations of Isocitrate Dehydrogenase (IDH) Mutant Targeted Therapies Plus Azacitidine: Oral COMPOUND 2 Plus Subcutaneous Azacitidine and Oral COMPOUND 1 Plus SC Azacitidine in Subjects with Newly Diagnosed Acute Myeloid Leukemia Harboring an IDH1 or an IDH2 Mutation, Respectively, Who are not Candidates to Receive Intensive Induction Chemotherapy Indication:

Treatment of patients 18 years and older with newly diagnosed acute myeloid leukemia (AML) with an IDH1 or an IDH2 mutation who are not candidates to receive intensive induction chemotherapy (IC).

Key Objectives—Phase 1b Dose-finding Stage

Primary Objectives

To assess the safety and tolerability of the combination treatments of oral COMPOUND 2 when administered with subcutaneous (SC) azacitidine and oral COMPOUND 1 when administered with SC azacitidine in subjects with newly diagnosed AML with an IDH1 or an IDH2 mutation, respectively, who are not candidates to receive intensive IC.

To establish the recommended combination dose (RCD) of oral COMPOUND 2 and oral COMPOUND 1 when administered with SC azacitidine.

Secondary Objective

To assess the preliminary efficacy of the combination treatments of oral COMPOUND 2 when administered with SC azacitidine and oral COMPOUND 1 when administered with SC azacitidine in subjects with newly diagnosed AML with an IDH1 or an IDH2 mutation, respectively, who are not candidates to receive intensive IC.

Phase 1b COMPOUND 2 Expansion Stage

Primary Objective

To assess the safety and tolerability of the combination treatments of oral COMPOUND 2 when administered with SC azacitidine in subjects with newly diagnosed AML with an IDH1 mutation who are not candidates to receive intensive IC.

Secondary Objective

To assess the preliminary efficacy of the combination treatments of oral COMPOUND 2 when administered with SC azacitidine in subjects with newly diagnosed AML with an IDH1 mutation, who are not candidates to receive intensive IC.

To characterize the pharmacokinetics (PK) of oral COMPOUND 2 when administered with SC azacitidine.

Phase 2 (COMPOUND 1 Randomized Stage)

Primary Objective

To assess the efficacy of oral COMPOUND 1 when administered with SC azacitidine versus SC azacitidine alone in subjects with newly diagnosed AML with an IDH2 mutation, who are not candidates to receive intensive IC.

Secondary Objectives

To evaluate the safety of oral COMPOUND 1 when administered with SC azacitidine.

To characterize the PK of oral COMPOUND 1 when administered with SC azacitidine.

To evaluate the effect of oral COMPOUND 1 when administered with SC azacitidine versus SC azacitidine alone on health-related quality-of-life (HRQoL) outcomes.

Study Design

This Phase 1b/2 study is an open-label, randomized, multicenter trial to evaluate the safety and efficacy of oral COMPOUND 2+SC azacitidine and oral COMPOUND 1+SC azacitidine in subjects with newly diagnosed AML with an IDH1 or an IDH2 mutation, respectively. The study population consists of subjects who are not candidates to receive intensive IC. The study comprises a Phase 1b dose-finding and COMPOUND 2 expansion stage and a Phase 2 randomized stage.

Phase 1b Dose-Finding Stage

The Phase 1b stage is an open-label dose-finding study to evaluate the safety and tolerability of oral COMPOUND 2 and oral COMPOUND 1 administered with SC azacitidine to define the RCD of these 2 agents when administered with SC azacitidine. The preliminary clinical activities of the oral COMPOUND 2+SC azacitidine and the oral COMPOUND 1+SC azacitidine regimens will also be assessed.

The Phase 1b stage consists of 3 periods: 1) screening; 2) treatment; and 3) follow-up.

Subject screening procedures will occur during the screening period within 28 days prior to the start of study treatment. The diagnosis of AML with an IDH mutation will be based on local review of both hematopathology and IDH gene mutation testing of bone marrow aspirate and/or peripheral blood samples. Subjects eligible for enrollment must not be candidates to receive intensive IC, based on the investigator's judgment, due to the presence of co-morbidities, declining performance status, or other factors. Subjects with newly diagnosed AML with an IDH1 mutation will be assigned to the oral COMPOUND 2+SC azacitidine arm, and subjects with newly diagnosed AML with an IDH2 mutation will be assigned to the oral COMPOUND 1+SC azacitidine arm. In the rare case in which a subject is diagnosed with an AML associated with dual IDH1 and IDH2 mutations, assignment to the oral COMPOUND 2 or COMPOUND 1 treatment arm will be based on a joint investigator and medical monitor decision and documented in the source.

During the treatment period a standard 3+3 design will be used. A Dose Review Team (DRT), consisting of a Celgene medical monitor, Celgene lead safety physician, Celgene biostatistician, other Celgene functional area representatives or designees, as appropriate, and all active site investigators and/or designees (at sites with a subject who has received study drug), will review all adverse events (AEs) experienced by subjects during Cycle 1 of each dose level to determine whether the maximum tolerated dose (MTD) of oral COMPOUND 2 or COMPOUND 1 when administered with SC azacitidine has been exceeded. One dose level of oral COMPOUND 2 (500 mg daily) and 2 dose levels of oral COMPOUND 1 (100 mg daily and 200 mg daily) are planned to be evaluated. Dose levels lower than 500 mg daily for oral COMPOUND 2 and lower than 100 mg daily for oral COMPOUND 1 will be evaluated if these doses when administered with SC azacitidine are found to exceed the MTD during Cycle 1. Dose interruptions/delays and dose reductions may be used to manage toxicities. Subjects may receive study treatment until disease progression/relapse, study treatment becomes intolerable, or the subject wishes to discontinue study treatment for any reason. Response to treatment will be assessed by the investigators according to the modified International Working Group (IWG) AML Response Criteria (Cheson et al. Revised recommendations of the International Working Group for diagnosis, standardization of response criteria, treatment outcomes, and reporting standards for therapeutic trials in acute myeloid leukemia. *J Clin Oncol* 2003; 21(24):4642-9.

Hematologic improvement (HI) in subjects with newly diagnosed AML will also be assessed according to the IWG myelodysplastic syndromes HI criteria (Cheson et al. Clinical application and proposal for modification of the International Working Group (IWG) response criteria in myelodysplasia. *Blood* 2006; 108(2):419-25). Subjects are to undergo end-of-treatment evaluations when study treatment is discontinued. The reason for treatment discontinuation will be recorded in the electronic case report form (eCRF) pages and in the source document.

All subjects discontinued from study treatment for any reason other than withdrawal of consent for follow-up will continue to be assessed for AEs, concomitant medications, concomitant procedures, transfusions, healthcare resource utilization, response, hematologic improvement, subsequent AML therapies, and survival.

All subjects discontinued from study treatment for any reason except withdrawal of consent for follow-up or disease progression will continue to be assessed during the Follow-up period of the study for response until disease progression.

All subjects discontinued from study treatment for any reason except withdrawal of consent for follow-up will continue to be assessed for subsequent AML therapies, and survival.

The study will be conducted in compliance with the International Conference on Harmonization (ICH) Good Clinical Practices (GCPs) guidelines.

Phase 1b COMPOUND 1 Expansion Stage

A Phase 1b expansion cohort of approximately 15 subjects with newly diagnosed AML with IDH1 mutation will be enrolled to the COMPOUND 2 combination. Subjects enrolled in the COMPOUND 2 expansion will receive the COMPOUND 2+azacitidine at the RCD.

Phase 2 COMPOUND 2 Randomized Stage

The Phase 2 stage is an open-label randomized study to evaluate the efficacy of oral COMPOUND 1 with SC azacitidine versus SC azacitidine alone in order to assess the overall response rate (ORR) and event-free survival (EFS).

The Phase 2 stage will also consist of 3 periods: 1) screening; 2) treatment; and 3) follow-up.

As with Phase 1b, subject screening procedures will occur during the screening period within 28 days prior to the start of study treatment, but the diagnosis of AML will be performed locally for enrollment and retrospectively confirmed based on a subsequent central pathology review. IDH mutational status will be assessed locally, and for sites without local testing capabilities a referral lab will be identified. A bone marrow aspirate and peripheral blood sample must be sent along with the correlative samples to the central lab for potential retrospective confirmation of mutational status. Inclusion in the trial can be based on local IDH testing. Subjects eligible for enrollment are those who are not candidates to receive intensive IC, based on the investigator's judgment, due to the presence of co-morbidities, declining performance status, or other factors.

Following review of eligibility, subjects with newly diagnosed AML with an IDH2 mutation will be randomized to receive oral COMPOUND 1+SC azacitidine (Arm 1) versus SC azacitidine alone (Arm 2) in a 2:1 ratio. Arm 1 will include a minimum of 66 subjects and Arm 2 will include a minimum of 33 subjects, (99 subjects total in both arms).

Subjects will be stratified by primary (ie, de novo) or secondary (progression of myelodysplastic syndrome (MDS) or myeloproliferative neoplasms [MPN], or therapy-related) AML according to the WHO classification.

Study treatment will start within 3 days of randomization. Assessments during study treatment include efficacy, safety, HRQoL, healthcare resource utilization, pharmacokinetics, pharmacodynamics, and correlative studies.

During both Phase 1b and Phase 2 a retrospective central pathology review of all bone marrow aspirates and/or biopsies and peripheral blood smears collected during screening will be conducted by personnel blinded to subject treatment to confirm eligibility. Bone marrow aspirate (BMA) and/or biopsy and peripheral blood smear collected after the start of study treatment must be available for both local and central pathology review. The retrospective central pathology review, will require a set of duplicate slides for each bone marrow collection time point including BMA, peripheral blood smear, and bone marrow biopsy (BMB) if performed. The central pathology review will be conducted by personnel blinded to study treatment.

Response to treatment and HI will be assessed by the investigators according to modified IWG AML Response Criteria (Cheson, 2003) and IWG myelodysplastic syndromes HI criteria (Cheson, 2006), respectively.

Dosing interruptions, dosing delays or dose modifications may occur for managing toxicities and/or augmenting treatment response during study treatment.

The discontinuation of COMPOUND 2, COMPOUND 1, or azacitidine for subjects in the combination arms of the study is allowed. Subjects may continue treatment with single agent COMPOUND 2, COMPOUND 1, or azacitidine if in the investigator's assessment the subject continues to show clinical benefit and all protocol-specified criteria for continuing study treatment are met. Study treatment will be discontinued if the subject has progressive disease or receives alternative therapies.

The decision to discontinue a subject, which will not be delayed or refused by the sponsor, remains the responsibility of the treating physician. However, prior to discontinuing a subject, it is recommended that the investigator contact the medical monitor and forward appropriate supporting documents for review and discussion.

All subjects who have received at least one dose of study treatment should undergo End of Treatment (EOT) evaluations when study treatment is discontinued. The reason for discontinuation will be recorded in the electronic case report form (eCRF) pages and in the source document.

All subjects discontinued from study treatment for any reason other than withdrawal of consent for follow-up will continue to be assessed for AEs, concomitant medications, concomitant procedures, transfusions, healthcare resource utilization, response, hematologic improvement, subsequent AML therapies, and survival.

All subjects discontinued from study treatment for any reason except withdrawal of consent for follow-up or disease progression will continue to be assessed during the Follow-up period of the study for response until disease progression.

All subjects discontinued from study treatment for any reason except withdrawal of consent for follow-up will continue to be assessed for subsequent AML therapies, and survival.

The study will be conducted in compliance with International Conference on Harmonization (ICH) Good Clinical Practices (GCPs).

Length of Study

The full length of the study is expected to be approximately 60 months including recruitment, screening, treatment, and follow up for Phase 1b and Phase 2. For a single subject, the expected duration of the Phase 1b segment of the study is approximately 13 months, including a screening period for up to 28 days, and the expected duration of the Phase 2 segment of the study is approximately 30 months, including a screening period for up to 28 days.

The End of Trial is defined as either the date of the last visit of the last subject to complete the post-treatment follow-up, or the date of receipt of the last data point from the last subject that is required for primary, secondary, and/or exploratory analysis, as pre-specified in the protocol, whichever is the later date.

Study Treatments

COMPOUND 2 and COMPOUND 1 are administered orally once a day (QD) on Days 1-28 of each 28-day cycle. Subjects should be instructed to take their daily dose at approximately the same time each day±6 hours. Each dose should be taken with a glass of water and consumed over as short a time as possible. Subjects should be instructed to swallow tablets whole and to not chew the tablets. Fasting is required for 2 hours prior to and 1 hour following COMPOUND 1 administration. Water is allowed during fasting. Fasting is not required for COMPOUND 2 administration.

Azacitidine will be administered SC for 7 days of each 28-day treatment cycle starting on Day 1 during both Phase 1b and Phase 2. In the Phase 1b COMPOUND 2 expansion stage, subjects with AML and with an IDH1 mutation may receive no more than one cycle of azacitidine for the treatment of AML prior to study enrollment. Cycle 1 of COMPOUND 2 with azacitidine must be given within 28 days from the initiation of the pre-study cycle of azacitidine.

During the Phase 2 stage, subjects randomized to the azacitidine alone arms will receive azacitidine 75 mg/m2/day SC for 7 days of each 28-day cycle. All randomized subjects will receive azacitidine 75 mg/m2/day SC for 7 days every 28 days until the end of the study, unless they are discontinued from the treatment. In addition, subjects may receive best supportive care as needed (please refer to local prescribing information and local therapeutic guidelines for more details on available formulations, preparation, storage conditions [eg, refrigeration], the approved indications, known precautions, warnings, and adverse reactions of best supportive care; (see current version of Prescribing Information), including antibiotics and transfusions, per investigator discretion. In the event that 2 or fewer doses are missed during the 7-day dosing period, dosing should continue so the subject receives the full 7 days of therapy. If 3 or more days are missed during the 7-day dosing period, the investigator should contact the sponsor and a decision on dosing will be made on a case-by-case basis.

Phase 1b (Dose-finding and COMPOUND 2 Expansion) Stage:

Phase 1b dose finding will use a 3+3 design. For COMPOUND 2 one dose level will be explored enrolling a minimum of 3 subjects. Cohort 1 will be initiated with oral COMPOUND 2 500 mg once a day and azacitidine 75 mg/m2/day SC for 7 days of each 28-day cycle starting on Day 1 of each cycle. A Cohort −1 will be explored with COMPOUND 2 250 mg once a day and azacitidine 75 mg/m2/day SC for 7 days of each 28-day cycle if 2 or more subjects in Cohort 1 have a dose-limiting toxicity (DLT) in cycle 1. Upon declaration of the RCD by the DRT an expansion cohort of up to 15 patients will be enrolled at the RCD for further safety evaluation and PK sampling.

For COMPOUND 1 two dose levels will be explored. Cohort 1 will be initiated with oral COMPOUND 1 100 mg once a day and azacitidine 75 mg/m2/day SC for 7 days of each 28-day cycle starting on Day 1 of each cycle. If no DLTs are observed, the RCD will be confirmed by the DRT and the 100 mg dose will be used as the starting dose for Phase 2 of the study. Dose escalation to Cohort 2 will be initiated with oral COMPOUND 1 200 mg once a day and azacitidine 75 mg/m2/day SC for 7 days of each 28-day cycle starting on Day 1 of each cycle to explore the tolerability of COMPOUND 1+SC azacitidine at this dose level. A Cohort −1 with oral COMPOUND 1 50 mg daily and azacitidine 75 mg/m2/day SC for 7 days of each 28-day cycle starting on Day 1 of each cycle will be explored if 2 or more subjects have a DLT in Cohort 1.

The DRT will evaluate all toxicities of each subject after 1 cycle and determine whether further dose modifications are needed for individual subjects.

Phase 2 COMPOUND 1 Randomized Stage:

COMPOUND 1+Azacitidine Arm (Arm 1):

Subjects with an IDH2 mutation will receive COMPOUND 1 at the RCD orally QD on Days 1-28 of each 28-day cycle+azacitidine 75 mg/m2/day SC for 7 days of each 28-day cycle.

Azacitidine Arm (Arm 2):

Subjects with IDH2 mutation will receive azacitidine 75 mg/m2/day SC for 7 days of each 28-day cycle.

Overview of Key Efficacy Assessments

Efficacy

Serial blood and bone marrow sampling will be used to determine response to therapy starting at Cycle 2. Response will be assessed locally during both phases according to the modified IWG criteria based on the centrally reported hematology laboratory parameters, peripheral blood smear, bone marrow aspirates and/or biopsies. Exploratory evaluation of response, as measured by flow cytometric measurement of minimal residual disease, will also be performed in Phase 2 subjects. The site needs to ensure peripheral blood for central hematology is collected and sent at the time of every bone marrow collection.

A retrospective pathology review will be performed. The retrospective central pathology review, will require a set of duplicate slides for each bone marrow collection time point including BMA, peripheral blood smear, and BMB if performed. The central pathology review will be conducted by personnel blinded to study treatment.

Instructions for submitting slides of bone marrow aspirate (and/or biopsy) and peripheral blood smear for central pathology review are provided in the Study Reference and/or Study Central Laboratory Manual.

Subjects who discontinue study treatment prior to relapse or progression will complete monthly site visits until confirmation of relapse or progression. For subjects who have discontinued study treatment due to relapse or progression, monthly follow up can be performed by site visits or phone calls. Subjects will be followed until they have died, are lost to follow up, withdraw consent for further data collection, or until study closure.

Overview of Other Key Assessments

Safety

Safety assessments include adverse events, physical examination, Eastern Cooperative Oncology Group (ECOG) performance status, vital signs, echocardiogram (ECHO) or multi-gated acquisition (MUGA) scan, electrocardiogram (ECG), cardiac markers, urinalysis, coagulation, hematology, serum chemistry, transfusions, pregnancy testing (for females of child bearing potential (FCBP) only), and concomitant medications or procedures.

Plasma PK/PD of COMPOUND 2 and COMPOUND 1

The PK profile of COMPOUND 2 when administered with SC Azacitidine will be evaluated by plasma concentrations and PK parameters of COMPOUND 2 in the Phase 1b expansion segment. Plasma concentrations of 2-HG will be evaluated in relation to plasma concentrations of COMPOUND 2 over time.

The PK profile of COMPOUND 1 when administered with SC Azacitidine will be evaluated by plasma concentrations and PK parameters of COMPOUND 1 in the Phase 2 segment. Plasma concentrations of 2-HG will be evaluated in relation to plasma concentrations of COMPOUND 1 over time Investigational Product Accountability Oral COMPOUND 2 and COMPOUND 1 are dispensed on Day 1 of each treatment cycle and accounted for after completion of each treatment cycle.

Azacitidine will be administered SC by study site personnel. Accurate recording of all IP dosing, will be made in the appropriate section of the subject's eCRF and source documents.

Statistical Methods

Phase 1b (Dose-finding and COMPOUND 2 Expansion) Stage:

Statistical analyses in Phase 1b will be primarily descriptive in nature. Tabulations will be produced for disposition, demographic and baseline disease characteristics, safety, PK, PD, and clinical activity parameters. Categorical data will be summarized by frequency distributions (numbers and percentages of subjects) and continuous data will be summarized by descriptive statistics (mean, standard deviation, median, minimum, and maximum). Data will be summarized by dose level and overall when appropriate.

Phase 2 COMPOUND 1 Randomized Stage:

The primary efficacy endpoint of Overall Response Rate (ORR) in Phase 2 includes responses of CR, CRp, CRi, morphologic leukemia-free state (MLFS), and PR, according to modified IWG AML response criteria. The treatment difference in ORR will be tested using the Chi square test in the ITT population. This test will provide the pivotal p-value for the comparison of the ORRs of oral COMPOUND 1+SC azacitidine versus azacitidine mono therapy group.

Approximately 99 subjects will be randomized in this study with 66 IDH2 subjects in the oral COMPOUND 1+SC azacitidine arm, and 33 IDH2 subjects in the SC azacitidine mono therapy arm. Assuming an ORR of 30% in the azacitidine mono therapy arm and an ORR of 50% for oral COMPOUND 1+SC azacitidine arm this designed sample size (66 in the COMPOUND 1+SC azacitidine and 33 in the azacitidine mono therapy arm) will provide 75% power to detect an 20% difference in ORR at a Type I error rate of 0.2 (two-sided).

Inclusion Criteria

Subjects must satisfy the following criteria to be enrolled in the study:

Subject is ≥18 years of age at the time of signing the informed consent form (ICF).

Subject must understand and voluntarily sign an ICF prior to any study-related assessments/procedures being conducted.

Subject is willing and able to adhere to the study visit schedule and other protocol requirements.

Subject has newly diagnosed, primary (ie, de novo) or secondary (progression of MDS or myeloproliferative neoplasms [MPN], or therapy-related) AML according to the WHO classification with ≥20% leukemic blasts in the bone marrow:

Have an IDH1 or IDH2 gene mutation (R132, R140, or R172)

IDH mutational status will be assessed locally; for sites without local testing capabilities, a referral lab will be identified By the investigator's assessment who are not candidates to receive intensive IC Subject has an Eastern Cooperative Oncology Group (ECOG) performance status of 0, 1 or 2.

Subject has adequate organ function defined as:

Serum aspartate aminotransferase/serum glutamic oxaloacetic transaminase (AST/SGOT) and alanine aminotransferase (ALT/SGPT)≤3×ULN, unless considered due to leukemic organ involvement.

Serum total bilirubin<1.5×ULN. Higher levels are acceptable if these can be attributed to ineffective erythropoiesis, ≤3 times the upper limit of normal for Gilbert's syndrome (eg, a gene mutation in UGT1A1), or leukemic organ involvement.

Serum creatinine<2×ULN or creatinine clearance ☐ 30 mL/min based on the Modification of Diet in Renal Disease (MDRD) glomerular filtration rate (GFR):

$$\text{GFR (mL/min/1.73 m}^2\text{)}=175\times(S_{cr})^{-1.154}\times(\text{Age})^{-0.203}\times(0.742 \text{ if female})\times(1.212 \text{ if African American})$$

Agree to serial bone marrow aspirate/biopsies.

Females of childbearing potential (FCBP)* may participate, providing they meet the following conditions:

Agree to practice true abstinence ** from sexual intercourse or to use highly effective contraceptive methods (eg, combined [containing estrogen and progestogen] or progestogen only associated with inhibition of ovulation, oral, injectable, intravaginal, patch, or implantable hormonal contraceptive; bilateral tubal occlusion; intra-uterine device; intrauterine hormone-releasing system; or male partner sterilization [note that a vasectomized partner is a highly effective birth control method provided that partner is the sole sexual partner of the FCBP trial participant and that a vasectomized partner has received medical assessment of the surgical success]) at screening and throughout the study, and for at least 4 months following the last study treatment; and Have a negative serum β-subunit of human chorionic gonadotropin (β-hCG) pregnancy test (sensitivity of at least 25 mIU/mL) at screening; and Have a negative serum or urine (investigator's discretion under local regulations) β hCG pregnancy test (sensitivity of at least 25 mIU/mL) within 72 hours prior to the start of study treatment in the Treatment Period (note that the screening serum pregnancy test can be used as the test prior to the start of study treatment in the Treatment Period if it is performed within the 72 hour timeframe).

Male subjects must agree to practice true abstinence from sexual intercourse or agree to the use of highly effective contraceptive methods (as described above) with non-pregnant female partners of child bearing potential at screening and throughout the course of the study and should avoid conception with their partners during the course of the study and for at least 4 months following the last study treatment (6 months following last dose of azacitidine in Canada).

Furthermore, the male subject must agree to use a condom while treated with azacitidine and for at least 4 months following the last azacitidine dose.

Exclusion Criteria

The presence of any of the following will exclude a subject from enrollment:

Subject is suspected or proven to have acute promyelocytic leukemia based on morphology, immunophenotype, molecular assay, or karyotype.

Subject has AML secondary to chronic myelogenous leukemia (CML).

Subject has received a targeted agent against an IDH1 or IDH2 mutation.

Subject has received prior systemic anticancer therapy, HSCT, or radiotherapy for AML. Note: Hydroxyurea is allowed prior to enrollment for the control of peripheral leukemic blasts in subjects with leukocytosis. (however, hydroxyurea should not be given within 72 hours prior to and after administration of azacitidine). For subjects with secondary AML (eg, MDS or MPN) treatment for prior cancer is not exclusionary; full treatment information will be collected within the CRF. The use of all trans retinoic acid (ATRA) for suspected APL is not exclusionary provided it is discontinued prior to initiation of treatment in the protocol.

Subject has received more than 1 cycle of prior treatment with azacitidine, or subject has received any prior treatment with decitabine for MDS.

Clarification: Subjects with newly diagnosed AML who are currently receiving their 1st cycle of azacitidine (7 days) can be screened for the study. On study, Cycle 1 of COMPOUND 1 or COMPOUND 2 with azacitidine must be started at 28 days (+/−3 days) after initiation of the pre-study azacitidine.

Subject has or is suspected of having central nervous system (CNS) leukemia. Evaluation of cerebrospinal fluid is only required if CNS involvement by leukemia is suspected during screening.

Subject has immediate life-threatening, severe complications of leukemia such as uncontrolled bleeding, pneumonia with hypoxia or shock, and/or disseminated intravascular coagulation.

Subject has significant active cardiac disease within 6 months prior to the start of study treatment, including New York Heart Association (NYHA) class III or IV congestive heart failure; acute coronary syndrome (ACS); and/or stroke; or left ventricular ejection fraction (LVEF)<40% by echocardiogram (ECHO) or multi-gated acquisition (MUGA) scan obtained within 28 days prior to the start of study treatment.

Subject has prior history of malignancy, other than MDS, MPN, or AML, unless the subject has been free of the disease for ≥1 year prior to the start of study treatment. However, subjects with the following history/concurrent conditions are allowed:

Basal or squamous cell carcinoma of the skin
Carcinoma in situ of the cervix
Carcinoma in situ of the breast
Incidental histologic finding of prostate cancer (T1a or T1b using the tumor, node, metastasis clinical staging system)

Subject is known seropositive for or has active viral infection with human immunodeficiency virus (HIV), or active infection with hepatitis B virus (HBV) or hepatitis C virus (HCV)

Subject is known to have dysphagia, short-gut syndrome, gastroparesis, or other conditions that limit the ingestion or gastrointestinal absorption of drugs administered orally Subject has uncontrolled hypertension (systolic blood pressure [BP]>180 mmHg or diastolic BP>100 mmHg)

Subject is taking the following sensitive CYP substrate medications that have a narrow therapeutic range are excluded from the study unless the subject can be transferred to other medications at least 5 half-lives prior to the start of study treatment: phenytoin (CYP2C9), S-mephenytoin (CYP2C19), thioridazine (CYP2D6), theophylline, and tizanidine (CYP1A2).

Subject is taking the breast cancer resistance protein (BCRP) transporter-sensitive substrate rosuvastatin; subject should be excluded from the study unless he/she can be transferred to other medications at least 5 half-lives prior to the start of study treatment.

Subject has active uncontrolled systemic fungal, bacterial, or viral infection (defined as ongoing signs/symptoms related to the infection without improvement despite appropriate antibiotics, antiviral therapy, and/or other treatment).

Subject has known or suspected hypersensitivity to any of the components of study therapy.

Subject is taking medications that are known to prolong the QT interval unless he/she can be transferred to other medications within ≥5 half-lives prior to the start of study treatment. (If equivalent medication is not available, QTc will be closely monitored)

Subject has QTc interval (ie, Fridericia's correction [QTcF])≥450 ms or other factors that increase the risk of QT prolongation or arrhythmic events (eg, heart failure, hypokalemia, family history of long QT interval syndrome) at screening.

Female subject who is pregnant or lactating.

Subject has any significant medical condition, laboratory abnormality, or psychiatric illness that would prevent the subject from participating in the study.

Subject has any condition, including the presence of laboratory abnormalities, that places the subject at unacceptable risk if he/she were to participate in the study.

Subject has any condition that confounds the ability to interpret data from the study.

Example 4: Synthesis of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol Example 4, Step 1: Preparation of 6-trifluoromethyl-pyridine-2-carboxylic Acid Diethyl ether (4.32 L) and hexanes (5.40 L) were added to the reaction vessel under $N_2$ atmosphere, and cooled to −75° C. to −65° C. Dropwise addition of n-Butyl lithium (3.78 L in 1.6 M hexane) under $N_2$ atmosphere at below −65° C. was followed by dropwise addition of dimethyl amino ethanol (327.45 g, 3.67 mol) and after 10 min. dropwise addition of 2-trifluoromethyl pyridine (360 g, 2.45 mol). The reaction was stirred under $N_2$ while maintaining the temperature below −65° C. for about 2.0-2.5 hrs. The reaction mixture was poured over crushed dry ice under $N_2$, then brought to a temperature of 0 to 5° C. while stirring (approx. 1.0 to 1.5 h) followed by the addition of water (1.8 L). The reaction mixture was stirred for 5-10 mins and allowed to warm to 5-10° C. 6N HCl (900 mL) was added dropwise until the mixture reached pH 1.0 to 2.0, then the mixture was stirred for 10-20 min. at 5-10° C. The reaction mixture was diluted with ethyl acetate at 25-35° C., then washed with brine solution. The reaction was concentrated and rinsed with n-heptane and then dried to yield 6-trifluoromethyl-pyridine-2-carboxylic acid.

Example 4, Step 2: Preparation of 6-trifluoromethyl-pyridine-2-carboxylic Acid Methyl Ester Methanol was added to the reaction vessel under nitrogen atmosphere. 6-trifluoromethyl-pyridine-2-carboxylic acid (150 g, 0.785 mol) was added and dissolved at ambient temperature. Acetyl chloride (67.78 g, 0.863 mol) was added dropwise at a temperature below 45° C. The reaction mixture was maintained at 65-70° C. for about 2-2.5 h, and then concentrated at 35-45° C. under vacuum and cooled to 25-35° C. The mixture was diluted with ethyl acetate and rinsed with saturated $NaHCO_3$ solution then rinsed with brine solution. The mixture was concentrated at 35-45° C. under vacuum and cooled to 25-35° C., then rinsed with n-heptane and concentrated at 35-45° C. under vacuum, then degassed to obtain brown solid, which was rinsed with n-heptane and stirred for 10-15 minute at 25-35° C. The suspension was cooled to −40 to −30° C. while stirring, and filtered and dried to provide 6-trifluoromethyl-pyridine-2-carboxylic acid methyl ester.

Example 4, Step 3: Preparation of 6-(6-trifluoromethyl-pyridin-2-yl)-1H-1,3,5-triazine-2,4-dione 1 L absolute ethanol was charged to the reaction vessel under $N_2$ atmosphere and sodium metal (11.2 g, 0.488 mol) was added in portions under $N_2$ atmosphere at below 50° C. The reaction was stirred for 5-10 minutes, then heated to 50-55° C. Dried Biuret (12.5 g, 0.122 mol) was added to the reaction vessel under $N_2$ atmosphere at 50-55° C. temperature, and stirred for 10-15 minutes. While maintaining 50-55° C. 6-trifluoromethyl-pyridine-2-carboxylic acid methyl ester (50.0 g, 0.244 mol) was added. The reaction mixture was heated to reflux (75-80° C.) and maintained for 1.5-2 hours, then cooled to 35-40° C., and concentrated at 45-50° C. under vacuum. Water was added and the mixture was concentrated under vacuum then cooled to 35-40° C., more water was added and the mixture was cooled to 0-5° C. pH was adjusted to 7-8 by slow addition of 6N HCl, a solid precipitated which was centrifuged and rinsed with water and centrifuged again. The off white to light brown solid of 6-(6-trifluoromethyl-pyridin-2-yl)-1H-1,3,5-triazine-2,4-dione was dried under vacuum for 8 to 10 hrs at 50° C. to 60° C. under 600 mm/Hg pressure to provide 6-(6-trifluoromethyl-pyridin-2-yl)-1H-1,3,5-triazine-2,4-dione.

Example 4, Step 4: Preparation of 2, 4-dichloro-6-(6-trifluoromethyl-pyridin-2-yl)-1,3,5-triazine POCl$_3$ (175.0 mL) is charged into the reaction vessel at 20-35° C., and 6-(6-trifluoromethyl-pyridin-2-yl)-1H-1,3,5-triazine-2,4-dione (35.0 g, 0.1355 mol) was added in portions at below 50° C. The reaction mixture was de-gassed 5-20 minutes by purging with N$_2$ gas. Phosphorous pentachloride (112.86 g, 0.542 mol) was added while stirring at below 50° C., the resulting slurry was heated to reflux (105-110° C.) and maintained for 3-4 h. The reaction mixture was cooled to 50-55° C., concentrated at below 55° C. then cooled to 20-30° C. The reaction mixture was rinsed with ethyl acetate and the ethyl acetate layer was slowly added to cold water (temperature ~5° C.) while stirring and maintaining the temperature below 10° C. The mixture was stirred 3-5 minutes at a temperature between 10 to 20° C. and the ethyl acetate layer was collected. The reaction mixture was rinsed with sodium bicarbonate solution and dried over anhydrous sodium sulphate. The material was dried 2-3 h under vacuum at below 45° C. to provide 2,4-dichloro-6-(6-trifluoromethyl-pyridin-2-yl)-1,3,5-triazine.

Example 4, Step 5: Preparation of 4-chloro-6-(6-(trifluoromethyl)pyridin-2-yl)-N-(2-(trifluoromethyl)-pyridin-4-yl)-1,3,5-triazin-2-amine A mixture of THF (135 mL) and 2,4-dichloro-6-(6-trifluoromethyl-pyridin-2-yl)-1, 3, 5-triazine (27.0 g, 0.0915 mol) were added to the reaction vessel at 20-35° C., then 4-amino-2-(trifluoromethyl)pyridine (16.31 g, 0.1006 mol) and sodium bicarbonate (11.52 g, 0.1372 mol) were added. The resulting slurry was heated to reflux (75-80° C.) for 20-24 h. The reaction was cooled to 30-40° C. and THF was evaporated at below 45° C. under reduced pressure. The reaction mixture was cooled to 20-35° C., rinsed with ethyl acetate and water, and the ethyl acetate layer was collected and rinsed with 0.5 N HCl and brine solution. The organic layer was concentrated under vacuum at below 45° C., then rinsed with dichloromethane and hexanes, filtered and washed with hexanes and dried for 5-6 h at 45-50° C. under vacuum to provide 4-chloro-6-(6-(trifluoromethyl)pyridin-2-yl)-N-(2-(trifluoro-methyl)-pyridin-4-yl)-1,3,5-triazin-2-amine.

Example 4, Step 6: Preparation of 2-methyl-1-(4-(6-(trifluoromethyl)pyridin-2-yl)-6-(2-(trifluoromethyl)-pyridin-4-ylamino)-1,3,5-triazin-2-ylamino)propan-2-ol THF (290 mL), 4-chloro-6-(6-(trifluoromethyl)pyridin-2-yl)-N-(2-(trifluoro-methyl)-pyridin-4-yl)-1,3,5-triazin-2-amine (29.0 g, 0.06893 mol), sodium bicarbonate (8.68 g, 0.1033 mol), and 1,1-dimethylaminoethanol (7.37 g, 0.08271 mol) were added to the reaction vessel at 20-35° C. The resulting slurry was heated to reflux (75-80° C.) for 16-20 h. The reaction was cooled to 30-40° C. and THF was evaporated at below 45° C. under reduced pressure. The reaction mixture was cooled to 20-35° C., rinsed with ethyl acetate and water, and the ethyl acetate layer was collected. The organic layer was concentrated under vacuum at below 45° C. then rinsed with dichloromethane and hexanes, filtered and washed with hexanes and dried for 8-10 h at 45-50° C. under vacuum to provide 2-methyl-1-(4-(6-(trifluoromethyl)pyridin-2-yl)-6-(2-(trifluoromethyl)-pyridin-4-ylamino)-1,3,5-triazin-2-ylamino)propan-2-ol.

Example 5: Synthesis of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate Acetone (435.0 mL) and 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol (87.0 g, 0.184 mol) were added to the reaction vessel at 20-35° C. In a separate vessel, methanesulfonic acid was added over 10 minutes to cold (0-4° C.) acetone (191.4 mL) while stirring to prepare a methane sulfonic acid solution. While passing through a micron filter, the freshly prepared methanesulfonic acid solution was added dropwise to the reaction mixture. The resulting slurry was filtered using nutsche filter and washed with acetone. The filtered material was dried for 30-40 minutes using vacuum to provide 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate.

Example 6: Synthesis of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate Form 3

Crystallization to Form 3 was accomplished via the following salt formation: 1) acetone (500 ml, 4.17 vol) was charged to the crystallizer, then the mixture was agitated (550 rpm) for 10 min., 2) 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol (120.0 g, 253.5 mmol) was charged into crystallizer via solid charger over 45 min., 3) the solid charger was rinsed with acetone (100 ml, 0.83 vol), 4) the reaction was stirred (550 rpm) and heated to 35° C. to obtain a clear solution (in 10 min), 5) a first portion (2%) of MSA/acetone solution (0.3 mol/L, 18.1 ml, 3.8 ml/min) was added over 5 min via a piston pump, then the pump pipeline was washed with acetone (5 ml, 0.04 vol), 6) the mixture was aged at 35° C. for 10 to 15 min, while ensuring the solution remained clear, 7) 2-methyl-1-[(4-[6-(trifluoromethyl)pyridin-2-yl]-6-{[2-(trifluoromethyl)pyridin-4-yl]amino})-1,3,5-triazin-2-yl)amino]propan-2-ol methanesulfonate seed (2.4 g as generated in Example 2, 2 wt %) was added to the clear solution, 8) a second portion (49%) of MSA/acetone solution (0.3 mol/L, 444 ml, 3.7 ml/min) was added over 2 hrs, 9) the mixture was aged at 35° C. for 30 min, 10) a third portion (49%) of MSA/acetone solution (0.3 mol/L, 444 ml, 7.4 ml/min) was added over 1 hr, 11) the mixture was aged at 35° C. for 2 hr, 12) the mixture was cooled to 20° C. for 1 hr, 13) the mixture was filtered and the cake washed with acetone (240 ml twice), 17) and dried under vacuum at 30° C.; to provide Form 3 crystals.

Having thus described several aspects of several embodiments, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

The invention claimed is:

1. A method of treating acute myelogenous leukemia, comprising administering to a subject a mutant isocitrate dehydrogenase 2 (IDH2) inhibitor and azacitidine, wherein the mutant IDH2 inhibitor is 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol having the following formula:

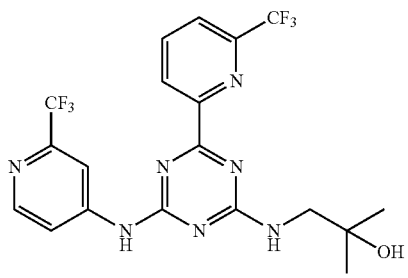 [SMILES: CC(C)(O)CNc1nc(Nc2ccnc(C(F)(F)F)c2)nc(-c2cccc(C(F)(F)F)n2)n1]

or a pharmaceutically acceptable salt, solvate, tautomer, stereoisomer, isotopologue, or a polymorph thereof (Compound 1), and wherein the acute myelogenous leukemia is characterized by the presence of a mutant allele of IDH2.

2. The method of claim 1, wherein the IDH2 mutation is an IDH2 R140Q or R172K mutation.

3. The method of claim 1, wherein the acute myelogenous leukemia is newly diagnosed.

4. The method of claim 1, wherein about 20 to 2000 mg/day of Compound 1 is administered to the subject.

5. The method of claim 1, wherein about 50 to 500 mg/day of Compound 1 is administered to the subject.

6. The method of claim 1, wherein about 50 mg/day of Compound 1 is administered to the subject.

7. The method of claim 1, wherein about 100 mg/day of Compound 1 is administered to the subject.

8. The method of claim 1, wherein about 200 mg/day of Compound 1 is administered to the subject.

9. The method of claim 1, wherein about 50 to about 500 mg/m$^2$ of azacitidine is administered to the subject.

10. The method of claim 1, wherein about 50 to about 200 mg/m$^2$ of azacitidine is administered to the subject.

11. The method of claim 1, wherein about 50 mg/m$^2$ of azacitidine is administered to the subject.

12. The method of claim 1, wherein about 60 mg/m$^2$ of azacitidine is administered to the subject.

13. The method of claim 1, wherein about 75 mg/m$^2$ of azacitidine is administered to the subject.

14. The method of claim 1, wherein Compound 1 and azacitidine are administered concurrently.

15. The method of claim 1, wherein Compound 1 and azacitidine are administered sequentially.

* * * * *